United States Patent
Liu et al.

(10) Patent No.: US 9,765,105 B2
(45) Date of Patent: Sep. 19, 2017

(54) MACROLIDE COMPOUND

(71) Applicant: Pulike Biological Engineering, Inc., Henan (CN)

(72) Inventors: Xingjin Liu, Henan (CN); Xuke Zhang, Henan (CN)

(73) Assignee: Pulike Biological Engineering, Inc., Henan (CN)

( * ) Notice: Subject to any disclaimer, the term of this patent is extended or adjusted under 35 U.S.C. 154(b) by 0 days.

(21) Appl. No.: 14/902,129

(22) PCT Filed: Nov. 1, 2013

(86) PCT No.: PCT/CN2013/086427
§ 371 (c)(1),
(2) Date: Dec. 30, 2015

(87) PCT Pub. No.: WO2015/024298
PCT Pub. Date: Feb. 26, 2015

(65) Prior Publication Data
US 2016/0304547 A1    Oct. 20, 2016

(30) Foreign Application Priority Data
Aug. 23, 2013 (CN) .......................... 2013 1 0373556

(51) Int. Cl.
| C07H 17/08 | (2006.01) |
| C07H 17/00 | (2006.01) |
| A61K 31/7052 | (2006.01) |
| A61K 31/706 | (2006.01) |

(52) U.S. Cl.
CPC ........... *C07H 17/00* (2013.01); *A61K 31/706* (2013.01); *A61K 31/7052* (2013.01); *C07H 17/08* (2013.01)

(58) Field of Classification Search
None
See application file for complete search history.

(56) References Cited

U.S. PATENT DOCUMENTS

| 4,474,768 A | 10/1984 | Bright |
| 4,517,367 A | 5/1985 | Skotsch et al. |
| 6,100,240 A | 8/2000 | Cheng et al. |
| 6,270,768 B1 | 8/2001 | O'Connell et al. |
| 6,407,074 B1 * | 6/2002 | Bronk ............... C07H 15/10 514/25 |
| 6,472,371 B1 | 10/2002 | Dirlam et al. |
| 7,015,203 B2 | 3/2006 | Dirlam et al. |
| 2003/0092640 A1 | 5/2003 | Boettner |
| 2004/0092459 A1 | 5/2004 | Dirlam et al. |
| 2004/0254126 A1 | 12/2004 | Qiu et al. |

FOREIGN PATENT DOCUMENTS

| CN | 1425022 A | 6/2003 |
| CN | 1530370 A | 9/2004 |
| CN | 102239174 A | 11/2011 |
| EP | 1262186 | * 12/1998 |
| EP | 0992509 A2 | 4/2000 |
| EP | 1024145 A2 | 8/2000 |
| EP | 1262186 A1 | 12/2002 |
| WO | WO-98/56801 A1 | 12/1998 |
| WO | WO-99/35156 A1 | 7/1999 |

OTHER PUBLICATIONS

International Search Report PCT/ISA/210 for International Application No. PCT/CN2013/086427 Dated Jul. 9, 2014.

* cited by examiner

*Primary Examiner* — Traviss C McIntosh, III
(74) *Attorney, Agent, or Firm* — Harness, Dickey & Pierce P.L.C.

(57) ABSTRACT

The present disclosure relates to a macrolide compound as shown by formula I and pharmaceutically acceptable salt thereof. The compound of the present disclosure is an antibacterial agent, and can be used to treat various bacterial and protozoal infections. The present disclosure further relates to the preparation method of the compound and a pharmaceutical composition thereof.

15 Claims, No Drawings

MACROLIDE COMPOUND

CROSS-REFERENCE TO RELATED APPLICATIONS

This application is a national phase under 35 U.S.C. §371 of PCT International Application No. PCT/CN2013/086427 which has an International filing date of Nov. 1, 2013, which claims priority to Chinese Patent Application No. 201310373556.0, filed Aug. 23, 2013, the entire contents of each of which are hereby incorporated by reference.

TECHNICAL FIELD

The present disclosure relates to the pharmaceutical field, and in particular to a novel 4"-substituted-9-deoxy-8A-aza-(8A-alkyl)-8A-homoerythromycin A derivative, an optical active isomer thereof, and a pharmaceutically acceptable salt thereof. The present disclosure also relates to a preparation method and a pharmaceutical composition comprising the derivative. The present disclosure further relates to use of the derivative in the treatment and/or prevention of diseases caused by various bacterial or protozoal infections.

TECHNICAL BACKGROUND

Macrolides, as an important category of anti-infection pharmaceuticals, have the advantages of excellent antibacterial activity, no anaphylactic reaction, minor side effect, and high safety. Through fifty years' development, the macrolides have become the second largest category of anti-infection pharmaceuticals, ranking only next to β-lactam antibiotics in clinical application, and occupies an important position in clinical treatment. Erythromycin, which had been widely used in the treatment of infections caused by *Staphylococcus aureus, Streptococcus pneumonia, Streptococcus hemolyticus, Mycoplasma pneumonia*, and the like, is one of the first generation macrolide antibiotics and is especially applicable to patients allergic to penicillin. However, the application of erythromycin is limited due to its instability in acid medium. The second generation macrolide antibiotics represented by azithromycin can solve the above problem, and are greatly improved in terms of potency and pharmacokinetics. Azithromycin (9-deoxo-9A-methyl-9A-aza-homoerythromycin A) is the first 15-membered ring marolide antibiotic discovered by Bright (U.S. Pat. No. 4,474,768) and Kobrehe (U.S. Pat. No. 4,517,367), et al. Azithromycin is a special macrolide antibiotic obtained from erythromycin through oximation, Beckmann rearrangement reaction, and introduction of a nitrogen atom into the lactone ring thereof, and subsequently reduction and methylation. Azithromycin has outstanding features including a high stability in acidic media, a good tissue penetration, a long plasma half life, a wide range of clinical applicability, a significant efficacy, and less adverse effect. In particular, azithromycin has a wider antibacterial spectrum, and has so good antibacterial activity that can inhibit gram negative bacilli, such as *Haemophilus influenza*, making up the insufficiency of macrolide antibiotics in the inhibition of gram negative bacilli.

Tulathromycin can be prepared by a process comprising firstly protecting the 2'-position of dihydro homoerythromycin, which is the starting material, then oxidizing and cyclizing the 4'-position thereof, removing the protecting group at the 2'-position, and subsequently aminating to form Tulathromycin in the form of salt. Tulathromycin is a newly launched macrolide semisynthetic antibiotic, which is specifically used on animals. Ministry of Agriculture of China issued a 957th announcement in 2008, first permitting the use of tulathromycin in animal production. Tulathromycin is mainly used in the treatment and prevention of swine and bovine respiratory diseases caused by *Actinobacillus, Mycoplasma, Pasteurella, Haemophilus parasuis*, and the like, and it has numerous advantages such as small dosage, single administration, low residue, and exclusive use on animals.

However, due to the wide use of antibiotics, in particular the continuous and improper use, drug resistance against macrolide antibiotics extensively used at present, such as azithromycin and tulathromycin, has been developed, which brings extreme difficulties to clinical treatment. In addition, acute toxicity tests have proven that tulathromycin has relatively high oral toxicity.

SUMMARY OF THE INVENTION

Given this, the present disclosure aims to provide a macrolide compound as shown by formula (I) and a pharmaceutically acceptable salt thereof.

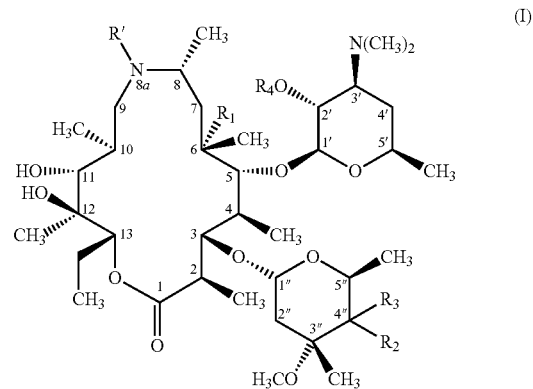

(I)

wherein R' is H or $C_1$-$C_6$ alkyl, $R_1$ is selected from a group consisting of H, hydroxyl, methoxyl, propargyl, aryl, and a nitrogen-containing heterocyclic group, $R_2$ is hydroxyl, $R_1$ is —$CH_2R$, wherein R is H or an organic group that contains or does not contain a heteroatom, the heteroatom being selected from a group consisting of O, N, S, and halogen, and $R_4$ is selected from a group consisting of H, acetyl, and carbobenzoxy.

In the compound according to the present disclosure, preferably, $R_3$ is —$CH_2NR_{20}R_{30}$ or —$CH_2SR_{40}$, wherein each $R_{20}$, $R_{30}$, and $R_{40}$ is independently H or an organic group that contains or does not contain a heteroatom, the heteroatom being selected from a group consisting of O, N, S, and halogen, and $R_{20}$ and $R_{30}$ being optionally bonded to each other to form a ring.

In the compound according to the present disclosure, preferably, $R_3$ is —$CH_2NHR_{50}$, and $R_{50}$ is an organic group that contains or does not contain a heteroatom, the heteroatom being selected from a group consisting of O, N, S, and halogen. More preferably, $R_{50}$ is selected from a group consisting of n-propyl, n-butyl, cyclopropyl, ethyl, isopropyl, isobutyl, tert-butyl, cyclopropylmethyl, 2-methoxyethyl, cyclopentyl, 2,4-difluorobenzyl, 3-methoxybenzyl, n-pentyl, 2-methyl-pyrazin-5-yl-methyl, 3-methoxypropyl, cyclohexylmethyl, and 4-methoxyphenethyl.

According to the present disclosure, preferably, $R_3$ is —$CH_2NR_{20}R_{30}$, and each $R_{20}$ and $R_{30}$ is independently selected from $C_1$-$C_6$ alkyl. More preferably, each $R_{20}$ and $R_{30}$ is independently methyl or ethyl.

In an embodiment according to the present disclosure, R in $R_3$ is a nitrogen-containing heterocyclic group, in which the nitrogen atom is directly attached to the carbon atom of methylene in $R_3$. Preferably, R in $R_3$ is morpholinyl, piperidinyl, or piperazinyl.

According to the present disclosure, preferably, $R_{20}$ and $R_{30}$ together form a 4 to 10-membered monocyclic ring, or a 5 to 10-membered heteroaryl ring optionally substituted by one or two alkyls.

According to the present disclosure, preferably, one of $R_{20}$ and $R_{30}$ is H, and the other thereof is an organic group containing phenyl or benzyl.

More preferably, the compound according to the present disclosure is a compound selected from a group consisting of:

1) (2R,3S,4R,5S,8R,10R,11R,12S,13S,14R)-13-[(2,6-dideoxy-3-C-methyl-3-O-methyl-4-C-[propylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

2) (2R,3S,4R,5S,8R,10R,11R,12S,13S,14R)-13-[(2,6-dideoxy-3-C-methyl-3-O-methyl-4-C-[butylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

3) (2R,3S,4R,5S,8R,10R,11R,12S,13S,14R)-13-[(2,6-dideoxy-3-C-methyl-3-O-methyl-4-C-[(diethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

4) (2R,3S,4R,5S,8R,10R,11R,12S,13S,14R)-13-[(2,6-dideoxy-3-C-methyl-3-O-methyl-4-C-[(phenylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

5) (2R,3S,4R,5S,8R,10R,11R,12S,13S,14R)-13-[(2,6-dideoxy-3-C-methyl-3-O-methyl-4-C-[(morpholinyl)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

6) (2R,3S,4R,5S,8R,10R,11R,12S,13S,14R)-13-[(2,6-dideoxy-3-C-methyl-3-O-methyl-4-C-[(cyclopropylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

7) (2R,3S,4R,5S,8R,10R,11R,12S,13S,14R)-13-[(2,6-dideoxy-3-C-methyl-3-O-methyl-4-C-[(pyrryl)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

8) (2R,3S,4R,5S,8R,10R,11R,12S,13S,14R)-13-[(2,6-dideoxy-3-C-methyl-3-O-methyl-4-C-[(4-fluorobenzylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

9) (2R,3S,4R,5S,8R,10R,11R,12S,13S,14R)-13-[(2,6-dideoxy-3-C-methyl-3-O-methyl-4-C-[(imidazolyl)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

10) (2R,3S,4R,5S,8R,10R,11R,12S,13S,14R)-13-[(2,6-dideoxy-3-C-methyl-3-O-methyl-4-C-[(ethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

11) (2R,3S,4R,5S,8R,10R,11R,12S,13S,14R)-13-[(2,6-dideoxy-3-C-methyl-3-O-methyl-4-C-[(isopropylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

12) (2R,3S,4R,5S,8R,10R,11R,12S,13S,14R)-13-[(2,6-dideoxy-3-C-methyl-3-O-methyl-4-C-[(isobutylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

13) (2R,3S,4R,5S,8R,10R,11R,12S,13S,14R)-13-[(2,6-dideoxy-3-C-methyl-3-O-methyl-4-C-[tert-butylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

14) (2R,3S,4R,5S,8R,10R,11R,12S,13S,14R)-13-[(2,6-dideoxy-3-C-methyl-3-O-methyl-4-C-[piperidinylmethyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

15) (2R,3S,4R,5S,8R,10R,11R,12S,13S,14R)-13-[(2,6-dideoxy-3-C-methyl-3-O-methyl-4-C-[(cyclopropylmethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

16) (2R,3S,4R,5S,8R,10R,11R,12S,13S,14R)-13-[(2,6-dideoxy-3-C-methyl-3-O-methyl-4-C-[(4-methoxybenzylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

17)
(2R,3S,4R,5S,8R,10R,11R,12S,13S,14R)-13-[(2,6-dideoxy-3-C-methyl-3-O-methyl-4-C-[(4-chlorolbenzylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

18)
(2R,3S,4R,5S,8R,10R,11R,12S,13S,14R)-13-[(2,6-dideoxy-3-C-methyl-3-O-methyl-4-C-[(3-pyridinylmethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

19)
(2R,3S,4R,5S,8R,10R,11R,12S,13S,14R)-13-[(2,6-dideoxy-3-C-methyl-3-O-methyl-4-C-[(3-ethoxypropyl)amino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

20)
(2R,3S,4R,5S,8R,10R,11R,12S,13S,14R)-13-[(2,6-dideoxy-3-C-methyl-3-O-methyl-4-C-[(2-methoxyethyl)aminomethyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

21)
(2R,3S,4R,5S,8R,10R,11R,12S,13S,14R)-13-[(2,6-dideoxy-3-C-methyl-3-O-methyl-4-C-[2-methoxybenzyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

22)
(2R,3S,4R,5S,8R,10R,11R,12S,13S,14R)-13-[(2,6-dideoxy-3-C-methyl-3-O-methyl-4-C-[2-[(N-methyl)amino]-ethyl)amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

23)
(2R,3S,4R,5S,8R,10R,11R,12S,13S,14R)-13-[(2,6-dideoxy-3-C-methyl-3-O-methyl-4-C-[(cyclopentylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

24)
(2R,3S,4R,5S,8R,10R,11R,12S,13S,14R)-13-[(2,6-dideoxy-3-C-methyl-3-O-methyl-4-C-[2,4-difluorobenzyl-amino]methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

25)
(2R,3S,4R,5S,8R,10R,11R,12S,13S,14R)-13-[(2,6-dideoxy-3-C-methyl-3-O-methyl-4-C-[(6-chloro-pyridazin-3-yl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

26)
(2R,3S,4R,5S,8R,10R,11R,12S,13S,14R)-13-[(2,6-dideoxy-3-C-methyl-3-O-methyl-4-C-[[(1-methyl-3-phenyl)propyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

27)
(2R,3S,4R,5S,8R,10R,11R,12S,13S,14R)-13-[(2,6-dideoxy-3-C-methyl-3-O-methyl-4-C-[[3-methoxybenzyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

28)
(2R,3S,4R,5S,8R,10R,11R,12S,13S,14R)-13-[(2,6-dideoxy-3-C-methyl-3-O-methyl-4-C-[[2,2,2-trifluoroacetyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

29)
(2R,3S,4R,5S,8R,10R,11R,12S,13S,14R)-13-[(2,6-dideoxy-3-C-methyl-3-O-methyl-4-C-[[[(2-chloro-pyridin-4-yl-amino)-methyl]-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

30)
(2R,3S,4R,5S,8R,10R,11R,12S,13S,14R)-13-[(2,6-dideoxy-3-C-methyl-3-O-methyl-4-C-[[[(4-formyl-benzyl-amino)-methyl]amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

31)
(2R,3S,4R,5S,8R,10R,11R,12S,13S,14R)-13-[(2,6-dideoxy-3-C-methyl-3-O-methyl-4-C-[[propargyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

32)
(2R,3S,4R,5S,8R,10R,11R,12S,13S,14R)-13-[(2,6-dideoxy-3-C-methyl-3-O-methyl-4-C-[[butyrate-2-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

33)
(2R,3S,4R,5S,8R,10R,11R,12S,13S,14R)-13-[(2,6-dideoxy-3-C-methyl-3-O-methyl-4-C-[[butyrate-4-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

34)
(2R,3S,4R,5S,8R,10R,11R,12S,13S,14R)-13-[(2,6-dideoxy-3-C-methyl-3-O-methyl-4-C-[(3-hydroxy-propylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

35)
(2R,3S,4R,5S,8R,10R,11R,12S,13S,14R)-13-[(2,6-dideoxy-3-C-methyl-3-O-methyl-4-C-[[n-pentyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

36)
(2R,3S,4R,5S,8R,10R,11R,12S,13S,14R)-13-[(2,6-dideoxy-3-C-methyl-3-O-methyl-4-C-[(morpholin-4-yl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

37)
3-({(2R,3S,4R,5S,8R,10R,11R,12S,13S,14R)-6-[-11-[[3,4,6-trideoxy-3-(dimethylamino)-β-D-xylo-hexopyranosyl]oxy]-2-ethyl-3,4,10-trihydroxy-3,5,8,10,12,14-hexamethyl-1-oxa-7-azacyclopentadecan-15-one-13-yl-oxy]-3-hydroxy-4-methoxy-2,4-dimethyl-tetrahydropyran-3-yl-methyl}-amino)-butyric acid;

38)
(2R,3S,4R,5S,8R,10R,11R,12S,13S,14R)-13-[(2,6-dideoxy-3-C-methyl-3-O-methyl-4-C-[(1-hydroxymethyl-propylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

39)
(2R,3S,4R,5S,8R,10R,11R,12S,13S,14R)-13-[(2,6-dideoxy-3-C-methyl-3-O-methyl-4-C-[(2-hydroxy-2-phenyl-ethylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

40)
(2R,3S,4R,5S,8R,10R,11R,12S,13S,14R)-13-[(2,6-dideoxy-3-C-methyl-3-O-methyl-4-C-[(4-dimethoxy-butylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

41)
(2R,3S,4R,5S,8R,10R,11R,12S,13S,14R)-13-[(2,6-dideoxy-3-C-methyl-3-O-methyl-4-C-[(3,4-dichloro-benzylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

42)
(2R,3S,4R,5S,8R,10R,11R,12S,13S,14R)-13-[(2,6-dideoxy-3-C-methyl-3-O-methyl-4-C-[(1-methyl-4-dimethyl-aminobutylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

43)
(2R,3S,4R,5S,8R,10R,11R,12S,13S,14R)-13-[(2,6-dideoxy-3-C-methyl-3-O-methyl-4-C-[[(3-cyclohexylamino)propylamino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

44)
(2R,3S,4R,5S,8R,10R,11R,12S,13S,14R)-13-[(2,6-dideoxy-3-C-methyl-3-O-methyl-4-C-[[(4-mesylphenylethylamino)propylamino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

45)
(2R,3S,4R,5S,8R,10R,11R,12S,13S,14R)-13-[(2,6-dideoxy-3-C-methyl-3-O-methyl-4-C-[[(1-methyl-but-1-en-3-yne-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

46)
(2R,3S,4R,5S,8R,10R,11R,12S,13S,14R)-13-[(2,6-dideoxy-3-C-methyl-3-O-methyl-4-C-[[(1-methyl-butyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

47)
(2R,3S,4R,5S,8R,10R,11R,12S,13R,14R)-13-[(2,6-dideoxy-3-C-methyl-3-O-methyl-4-C-[[(2-pyridin-4-yl-ethyl-amine)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

48)
(2R,3S,4R,5S,8R,10R,11R,12S,13S,14R)-13-[(2,6-dideoxy-3-C-methyl-3-O-methyl-4-C-{[(5-methyl-pyrazin-2-yl-methyl)-amino]-methyl}-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

49)
(2R,3S,4R,5S,8R,10R,11R,12S,13S,14R)-13-[(2,6-dideoxy-3-C-methyl-3-O-methyl-4-C-[[(3-methoxy-propyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxo-7-azacyclopentadecan-15-one;

50)
(2R,3S,4R,5S,8R,10R,11R,12S,13S,14R)-13-[(2,6-dideoxy-3-C-methyl-3-O-methyl-4-C-[[(cyclohexyl-methyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxo-7-azacyclopentadecan-15-one;

51)
(2R,3S,4R,5S,8R,10R,11R,12S,13S,14R)-13-[(2,6-dideoxy-3-C-methyl-3-O-methyl-4-C-[(2-fluoro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

52)
(2R,3S,4R,5S,8R,10R,11R,12S,13S,14R)-13-[(2,6-dideoxy-3-C-methyl-3-O-methyl-4-C-[(3-morpholinyl-propyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

53)
(2R,3S,4R,5S,8R,10R,11R,12S,13S,14R)-13-[(2,6-dideoxy-3-C-methyl-3-O-methyl-4-C-[(2-furfuryl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

54)
(2R,3S,4R,5S,8R,10R,11R,12S,13S,14R)-13-[(2,6-dideoxy-3-C-methyl-3-O-methyl-4-C-[(3-aminobenzyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

55)
(2R,3S,4R,5S,8R,10R,11R,12S,13S,14R)-13-[(2,6-dideoxy-3-C-methyl-3-O-methyl-4-C-[(phenylhydrazono)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

56)
(2R,3S,4R,5S,8R,10R,11R,12S,13S,14R)-13-[(2,6-dideoxy-3-C-methyl-3-O-methyl-4-C-{[2-(1H-indol-3-yl)-ethylamino]-methyl}-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

57)
(2R,3S,4R,5S,8R,10R,11R,12S,13S,14R)-13-[(2,6-dideoxy-3-C-methyl-3-O-methyl-4-C-[(3-chloropropyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

58)
(2R,3S,4R,5S,8R,10R,11R,12S,13S,14R)-13-[(2,6-dideoxy-3-C-methyl-3-O-methyl-4-C-[(3,5-dimethoxyphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

59)
(2R,3S,4R,5S,8R,10R,11R,12S,13S,14R)-13-[(2,6-dideoxy-3-C-methyl-3-O-methyl-4-C-[(thienylformyloxymethyl-2-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

60)
(2R,3S,4R,5S,8R,10R,11R,12S,13S,14R)-13-[(2,6-dideoxy-3-C-methyl-3-O-methyl-4-C-[(5-methylfurfurylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

61)
(2R,3S,4R,5S,8R,10R,11R,12S,13S,14R)-13-[(2,6-dideoxy-3-C-methyl-3-O-methyl-4-C-[(4-fluoro-phenylhydrazono)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

62)
(2R,3S,4R,5S,8R,10R,11R,12S,13S,14R)-13-[(2,6-dideoxy-3-C-methyl-3-O-methyl-4-C-[(benzyloxy-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

63)
(2R,3S,4R,5S,8R,10R,11R,12S,13S,14R)-13-[(2,6-dideoxy-3-C-methyl-3-O-methyl-4-C-[(p-methoxyphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

64)
(2R,3S,4R,5S,8R,10R,11R,12S,13S,14R)-13-[(2,6-dideoxy-3-C-methyl-3-O-methyl-4-C-[(3,4-dimethylphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

65)
(2R,3S,4R,5S,8R,10R,11R,12S,13S,14R)-13-[(2,6-dideoxy-3-C-methyl-3-O-methyl-4-C-[(5-fluoropyridin-2-yl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

66)
(2R,3S,4R,5S,8R,10R,11R,12S,13S,14R)-13-[(2,6-dideoxy-3-C-methyl-3-O-methyl-4-C-[(2-pyrrolyl-ethyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

67)
(2R,3S,4R,5S,8R,10R,11R,12S,13S,14R)-13-[(2,6-dideoxy-3-C-methyl-3-O-methyl-4-C-[(2-pyridin-4-yl-ethyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

68)
(2R,3S,4R,5S,8R,10R,11R,12S,13S,14R)-13-[(2,6-dideoxy-3-C-methyl-3-O-methyl-4-C-[(2-fluorobenzyl-amino)-methyl]-α-L-ribopyranosyl)oxy]-2-ethyl-3,4,10-trihydroxy-3,5,10,12,14-hexamethyl-11-[[3,4,6-trideoxy-3-(dimethylamino)-β-D-xylo-hexopyranosy]oxy]-1-oxa-7-azacyclopentadecan-15-one;

69)
(2R,3S,4R,5S,8R,10R,11R,12S,13S,14R)-13-[(2,6-dideoxy-3-C-methyl-3-O-methyl-4-C-[(2-piperidin-4-yl-methyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino-β-D-xylo-hexopyranosy]oxy]-1-oxa-7-azacyclopentadecan-15-one;

70)
(2R,3S,4R,5S,8R,10R,11R,12S,13S,14R)-13-[(2,6-dideoxy-3-C-methyl-3-O-methyl-4-C-[(5-chloro-o-methylphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one, 71)
(2R,3S,4R,5S,8R,10R,11R,12S,13S,14R)-13-[(2,6-dideoxy-3-C-methyl-3-O-methyl-4-C-[(2-fluoro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

72)
(2R,3S,4R,5S,8R,10R,11R,12S,13S,14R)-13-[(2,6-dideoxy-3-C-methyl-3-O-methyl-4-C-[(2-fluoro-5-methylphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

73)
(2R,3S,4R,5S,8R,10R,11R,12S,13S,14R)-13-[(2,6-dideoxy-3-C-methyl-3-O-methyl-4-C-[(2-methyl-4-chloro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

74) (2R,3S,4R,5S,8R,10R,11R,12S,13S,14R)-13-[(2,6-dideoxy-3-C-methyl-3-O-methyl-4-C-[(N-methyl-butyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

75) (2R,3S,4R,5S,8R,10R,11R,12S,13S,14R)-13-[(2,6-dideoxy-3-C-methyl-3-O-methyl-4-C-[(quinolin-6-yl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxo-7-azacyclopentadecan-15-one;

76) (2R,3S,4R,5S,8R,10R,11R,12S,13S,14R)-13-[(2,6-dideoxy-3-C-methyl-3-O-methyl-4-C-[(1,2,2-trimethyl-propylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

77) (2R,3S,4R,5S,8R,10R,11R,12S,13S,14R)-13-[(2,6-dideoxy-3-C-methyl-3-O-methyl-4-C-[(n-propyl-amino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

78) (2R,3S,4R,5S,8R,10R,11R,12S,13S,14R)-13-[(2,6-dideoxy-3-C-methyl-3-O-methyl-4-C-[(n-butyl-amino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

79) (2R,3S,4R,5S,8R,10R,11R,12S,13S,14R)-13-[(2,6-dideoxy-3-C-methyl-3-O-methyl-4-C-[(pentylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

80) (2R,3S,4R,5S,8R,10R,11R,12S,13S,14R)-13-[(2,6-dideoxy-3-C-methyl-3-O-methyl-4-C-[(diethylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

81) (2R,3S,4R,5S,8R,10R,11R,12S,13S,14R)-13-[(2,6-dideoxy-3-C-methyl-3-O-methyl-4-C-[(phenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

82) (2R,3S,4R,5S,8R,10R,11R,12S,13S,14R)-13-[(2,6-dideoxy-3-C-methyl-3-O-methyl-4-C-[(morpholinyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

83) (2R,3S,4R,5S,8R,10R,11R,12S,13S,14R)-13-[(2,6-dideoxy-3-C-methyl-3-O-methyl-4-C-{[(5-amino-1,3,3-trimethyl-cyclohexylmethyl)-amino]-methyl}-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

84) 13-[(2,6-dideoxy-3-C-methyl-3-O-methyl-4-C-[piperonylamino-methyl)]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

85) (2R,3S,4R,5S,8R,10R,11R,12S,13S,14R)-13-[(2,6-dideoxy-3-C-methyl-3-O-methyl-4-C-[(4-(fluorobenzylamino) methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

86) (2R,3S,4R,5S,8R,10R,11R,12S,13S,14R)-13-[(2,6-dideoxy-3-C-methyl-3-O-methyl-4-C-[(1,2,3-triazolyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

87) (2R,3S,4R,5S,8R,10R,11R, S,13S,14R)-13-[(2,6-dideoxy-3-C-methyl-3-O-methyl-4-C-[(ethylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

88) (2R,3S,4R,5S,8R,10R,11R,1S,13S,14R)-13-[(2,6-dideoxy-3-C-methyl-3-O-methyl-4-C-[(isopropylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

89) (2R,3S,4R,5S,8R,10R,11R,12S,13S,14R)-13-[(2,6-dideoxy-3-C-methyl-3-O-methyl-4-C-[(isobutylamino)methyl-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

90) (2R,3S,4R,5S,8R,10R,11R,12S,13S,14R)-13-[(2,6-dideoxy-3-C-methyl-3-O-methyl-4-C-[(3-chlorophenylamino) methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

91) (2R,3S,4R,5S,8R,10R,11R,12S,13S,14R)-13-[(2,6-dideoxy-3-C-methyl-3-O-methyl-4-C-[(tert-butylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

92) (2R,3S,4R,5S,8R,10R,11R,12S,13S,14R)-13-[(2,6-dideoxy-3-C-methyl-3-O-methyl-4-C-[(n-hexylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one;

93)
(2R,3S,4R,5S,8R,10R,11R,12S,13S,14R)-13-[(2,6-dideoxy-3-C-methyl-3-O-methyl-4-C-[(4-trifluoromethylbenzylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

94)
(2R,3S,4R,5S,8R,10R,11R,12S,13S,14R)-13-[(2,6-dideoxy-3-C-methyl-3-O-methyl-4-C-[(cyclopropyl-methylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

95)
(2R,3S,4R,5S,8R,10R,11R,12S,13S,14R)-13-[(2,6-dideoxy-3-C-methyl-3-O-methyl-4-C-[(4-methoxy-benzylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

96)
(2R,3S,4R,5S,8R,10R,11R,12S,13S,14R)-13-[(2,6-dideoxy-3-C-methyl-3-O-methyl-4-C-[[(4-nitro-benzyl)amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

97)
(2R,3S,4R,5S,8R,10R,11R,12S,13S,14R)-13-[(2,6-dideoxy-3-C-methyl-3-O-methyl-4-C-[4-chloro-benzyl-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

98)
(2R,3S,4R,5S,8R,10R,11R,12S,13S,14R)-13-[(2,6-dideoxy-3-C-methyl-3-O-methyl-4-C-[(3-pyridinyl-methylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

99)
(2R,3S,4R,5S,8R,10R,11R,12S,13S,14R)-13-[(2,6-dideoxy-3-C-methyl-3-O-methyl-4-C-[[(3-ethyoxyl-propyl)-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

100)
(2R,3S,4R,5S,8R,10R,11R,12S,13S,14R)-13-[(2,6-dideoxy-3-C-methyl-3-O-methyl-4-C-[(2-methoxyethyl)-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

101)
(2R,3S,4R,5S,8R,10R,11R,12S,13S,14R)-13-[(2,6-dideoxy-3-C-methyl-3-O-methyl-4-C-[(N-methyl-2-hydroxyethyl)amino-methyl]-α-L-ribopyranosyl)oxy]-2-ethyl-3,4,10-trihydroxy-3,5,7,8,10,12,14-hexamethyl-7-propyl-11-[[3,4,6-trideoxy-3-(dimethylamino)-β-D-xylohexopyranosyl]oxy]-1-oxa-7-azacyclopentadecan-15-one;

102)
(2R,3S,4R,5S,8R,10R,11R,12S,13S,14R)-13-[(2,6-dideoxy-3-C-methyl-3-O-methyl-4-C-[(3-methoxy-benzyl)-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

103)
(2R,3S,4R,5S,8R,10R,11R,12S,13S,14R)-13-[(2,6-dideoxy-3-C-methyl-3-O-methyl-4-C-[(cyclopentyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

104)
(2R,3S,4R,5S,8R,10R,11R, S,13S,14R)-13-[(2,6-dideoxy-3-C-methyl-3-O-methyl-4-C-[(2,4-difluorobenzyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-3-D-xylo-hexopyranosyl]oxy]-1-oxa-7-azacyclopentadecan-15-one;

105)
(2R,3S,4R,5S,8R,10R,11R,1S,13S,14R)-13-[(2,6-dideoxy-3-C-methyl-3-O-methyl-4-C-[(6-chloro-pyridazin-3-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino-β-D-xylo-hexopyranosyl]oxy]-1-oxa-7-azacyclopentadecan-15-one;

106)
(2R,3S,4R,5S,8R,10R,11R,12S,13S,14R)-13-[(2,6-dideoxy-3-C-methyl-3-O-methyl-4-C-[(4-hydroxy-butylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

107)
(2R,3S,4R,5S,8R,10R,11R,12S,13S,14R)-13-[(2,6-dideoxy-3-C-methyl-3-O-methyl-4-C-[(1-methyl-3-phenyl-propylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

108)
(2R,3S,4R,5S,8R,10R,11R,12S,13S,14R)-13-[(2,6-dideoxy-3-C-methyl-3-O-methyl-4-C-[(3-methoxy-benzylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

109)
(2R,3S,4R,5S,8R,10R,11R,12S,13S,14R)-13-[(2,6-dideoxy-3-C-methyl-3-O-methyl-4-C-[piperazinyl-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

110)
(2R,3S,4R,5S,8R,10R,11R,12S,13S,14R)-13-[(2,6-dideoxy-3-C-methyl-3-O-methyl-4-C-[[trifluoroacetylamino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

111)
(2R,3S,4R,5S,8R,10R,11R,12S,13S,14R)-13-[(2,6-dideoxy-3-C-methyl-3-O-methyl-4-C-[[[(2-chloro-pyridin-4-yl-amino)-methyl]-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

112)
(2R,3S,4R,5S,8R,10R,11R,12S,13S,14R)-13-[(2,6-dideoxy-3-C-methyl-3-O-methyl-4-C-[[4-formylbenzylamino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

113)
(2R,3S,4R,5S,8R,10R,11R,12S,13S,14R)-13-[(2,6-dideoxy-3-C-methyl-3-O-methyl-4-C-[[propargyl-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

114)
(2R,3S,4R,5S,8R,10R,11R,12S,13S,14R)-13-[(2,6-dideoxy-3-C-methyl-3-O-methyl-4-C-[[1-butyrate2-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

115)
(2R,3S,4R,5S,8R,10R,11R,12S,13S,14R)-13-[(2,6-dideoxy-3-C-methyl-3-O-methyl-4-C-[[1-butyrate4-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

116)
(2R,3S,4R,5S,8R,10R,11R,12S,13S,14R)-13-[(2,6-dideoxy-3-C-methyl-3-O-methyl-4-C-[[diglycol-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

117)
(2R,3S,4R,5S,8R,10R,11R,12S,13S,14R)-13-[(2,6-dideoxy-3-C-methyl-3-O-methyl-4-C-[(2-hydroxy-1-hydroxyethyl-ethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

118)
(2R,3S,4R,5S,8R,10R,11R,12S,13S,14R)-13-[(2,6-dideoxy-3-C-methyl-3-O-methyl-4-C-[(3-hydroxy-propylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

119)
(2R,3S,4R,5S,8R,10R,11R,12S,13S,14R)-13-[(2,6-dideoxy-3-C-methyl-3-O-methyl-4-C-[[n-pentyl-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

120)
(2R,3S,4R,5S,8R,10R,11R,12S,13S,14R)-13-[(2,6-dideoxy-3-C-methy)-3-O-methyl-4-C-[(morpholin-4-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

121)
(2R,3S,4R,5S,8R,10R,11S,13S,14R)-13-[(2,6-dideoxy-3-C-methyl-3-O-methyl-4-C-[(3-amino-butyrate)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

122)
(2R,3S,4R,5S,8R,10R,11S,13S,14R)-13-[(2,6-dideoxy-3-C-methyl-3-O-methyl-4-C-[(1-hydroxymethyl-propylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

123)
(2R,3S,4R,5S,8R,10R,11R,12S,13S,14R)-13-[(2,6-dideoxy-3-C-methyl-3-O-methyl-4-C-[(2-hydroxy-2-phenyl-ethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

124)
(2R,3S,4R,5S,8R,10R,11R,12S,13S,14R)-13-[(2,6-dideoxy-3-C-methyl-3-O-methyl-4-C-[(3,4-difluorophenylmethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

125)
(2R,3S,4R,5S,8R,10R,11R,12S,13S,14R)-13-[(2,6-dideoxy-3-C-methyl-3-O-methyl-4-C[(3,5-difluorophenylmethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

126)
(2R,3S,4R,5S,8R,10R,11R,12S,13S,14R)-13-[(2,6-dideoxy-3-C-methyl-3-O-methyl-4-C-[(2-methoxyethylamino)-methyl]α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

127)
(2R,3S,4R,5S,8R,10R,11R,12S,13S,14R)-13-[(2,6-dideoxy-3-C-methyl-3-O-methyl-4-C-[(1-methyl-4-diethylaminobutylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

128)
(2R,3S,4R,5S,8R,10R,11R,12S,13S,14R)-13-[(2,6-dideoxy-3-C-methyl-3-O-methyl-4-C-[[4-sulphonylamino-phenylethylamino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

129)
(2R,3S,4R,5S,8R,10R,11R,12S,13S,14R)-13-[(2,6-dideoxy-3-C-methyl-3-O-methyl-4-C-[[(1-methyl-but-1-ene-3-yne-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

130)
(2R,3S,4R,5S,8R,10R,11R,12S,13S,14R)-13-[(2,6-dideoxy-3-C-methyl-3-O-methyl-4-C-[[(1-methyl-butylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

131)
(2R,3S,4R,5S,8R,10R,11R,12S,13S,14R)-13-[(2,6-dideoxy-3-C-methyl-3-O-methyl-4-C-[[(2-pyridin-4-yl-ethyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

132)
(2R,3S,4R,5S,8R,10R,11R,12S,13S,14R)-13-[(2,6-dideoxy-3-C-methyl-3-O-methyl-4-C-{[(5-methyl-pyrazin-2-yl-methyl)-amino]-methyl}-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

133)
(2R,3S,4R,5S,8R,10R,11R,12S,13S,14R)-13-[(2,6-dideoxy-3-C-methyl-3-O-methyl-4-C-[[(cyclohexyl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

134)
(2R,3S,4R,5S,8R,10R,11R,12S,13S,14R)-13-[(2,6-dideoxy-3-C-methyl-3-O-methyl-4-C-[(2-fluoro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

135)
(2R,3S,4R,5S,8R,10R,11R,12S,13S,14R)-13-[(2,6-dideoxy-3-C-methyl-3-O-methyl-4-C-[(3-morpholinyl-propyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

136)
(2R,3S,4R,5S,8R,10R,11R,12S,13S,14R)-13-[(2,6-dideoxy-3-C-methyl-3-O-methyl-4-C-[(2-chloro-phenylmethyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

137)
(2R,3S,4R,5S,8R,10R,11R,12S,13S,14R)-13-[(2,6-dideoxy-3-C-methyl-3-O-methyl-4-C-[(2-furyl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

138)
(2R,3S,4R,5S,8R,10R,11R,1S,13S,14R)-13-[(2,6-dideoxy-3-C-methyl-3-O-methyl-4-C-[(3-aminobenzyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

139)
(2R,3S,4R,5S,8R,10R,11R,1S,13S,14R)-13-[(2,6-dideoxy-3-C-methyl-3-O-methyl-4-C-[(phenylhydrazono)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

140)
(2R,3S,4R,5S,8R,10R,11R,12S,13S,14R)-13-[(2,6-dideoxy-3-C-methyl-3-O-methyl-4-C-{[2-(1H-indol-3-yl)-ethylamino]-methyl}-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

141)
(2R,3S,4R,5S,8R,10R,11R,12S,13S,14R)-13-[(2,6-dideoxy-3-C-methyl-3-O-methyl-4-C-[(3-chloro-propyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

142)
(2R,3S,4R,5S,8R,10R,11R,12S,13S,14R)-13-[(2,6-dideoxy-3-C-methyl-3-O-methyl-4-C-[(3,5-dimethoxyphenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

143)
(2R,3S,4R,5S,8R,10R,11R,12S,13S,14R)-13-[(2,6-dideoxy-3-C-methyl-3-O-methyl-4-C-[(5-methyl-furan-2-O-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

144)
(2R,3S,4R,5S,8R,10R,11R,12S,13S,14R)-13-[(2,6-dideoxy-3-C-methyl-3-O-methyl-4-C-[(4-fluoro-phenylhydrazono)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

145)
(2R,3S,4R,5S,8R,10R,11R,12S,13S,14R)-13-[(2,6-dideoxy-3-C-methyl-3-O-methyl-4-C-[(benzyloxy-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

146)
(2R,3S,4R,5S,8R,10R,11R,12S,13S,14R)-13-[(2,6-dideoxy-3-C-methyl-3-O-methyl-4-C-[(p-methoxyphenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

147)
(2R,3S,4R,5S,8R,10R,11R,12S,13S,14R)-13-[(2,6-dideoxy-3-C-methyl-3-O-methyl-4-C-[(3,4-dimethylphenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

148)
(2R,3S,4R,5S,8R,10R,11R,12S,13S,14R)-13-[(2,6-dideoxy-3-C-methyl-3-O-methyl-4-C-[(4-fluorothiophenol)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

149)
(2R,3S,4R,5S,8R,10R,11R,12S,13S,14R)-13-[(2,6-dideoxy-3-C-methyl-3-O-methyl-4-C-[(5-fluoropyridinyl-2-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

150)
(2R,3S,4R,5S,8R,10R,11R,12S,13S,14R)-13-[(2,6-dideoxy-3-C-methyl-3-O-methyl-4-C-[(diethyl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

151)
(2R,3S,4R,5S,8R,10R,11R,12S,13S,14R)-13-[(2,6-dideoxy-3-C-methyl-3-O-methyl-4-C-[(3-morpholinyl-propyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

152)
(2R,3S,4R,5S,8R,10R,11R,12S,13S,14R)-13-[(2,6-dideoxy-3-C-methyl-3-O-methyl-4-C-[(2-pyrrolyl-ethyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

153)
(2R,3S,4R,5S,8R,10R,11R,12S,13S,14R)-13-[(2,6-dideoxy-3-C-methyl-3-O-methyl-4-C-[(2-pyridin-4-yl-ethyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

154)
(2R,3S,4R,5S,8R,10R,11R,12S,13S,14R)-13-[(2,6-dideoxy-3-C-methy)-3-O-methyl-4-C-[(2-fluorobenzyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

155)
(2R,3S,4R,5S,8R,10R,11R, S,13S,14R)-13-[(2,6-dideoxy-3-C-methyl-3-O-methyl-4-C-[(2-piperidin-4-yl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

156)
(2R,3S,4R,5S,8R,10R,11R, S,13S,14R)-13-[(2,6-dideoxy-3-C-methyl-3-O-methyl-4-C-[(2-methyl-4-chloro-phenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

157)
(2R,3S,4R,5S,8R,10R,11R$_2$12S,13S,14R)-13-[(2,6-dideoxy-3-C-methyl-3-O-methyl-4-C-[(N-methyl-butyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

158)
(2R,3S,4R,5S,8R,10R,11R$_2$12S,13S,14R)-13-[(2,6-dideoxy-3-C-methyl-3-O-methyl-4-C-[(4,6-dichloro-pyrimidin-2-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

159)
(2R,3S,4R,5S,8R,10R,11R$_2$12S,13S,14R)-13-[(2,6-dideoxy-3-C-methyl-3-O-methyl-4-C-[(cycloheptylamino)-methyl]α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

160)
(2R,3S,4R,5S,8R,10R,11R,12S,13S,14R)-13-[(2,6-dideoxy-3-C-methyl-3-O-methyl-4-C-(morpholinyl-methyl)-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

161)
(2R,3S,4R,5S,8R,10R,11R,12S,13S,14R)-13-[(2,6-dideoxy-3-C-methyl-3-O-methyl-4-C-[(4,4-dimethoxy-butylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

162)
(2R,3S,4R,5S,8R,10R,11R,12S,13S,14R)-13-[(2,6-dideoxy-3-C-methyl-3-O-methyl-4-C-(piperidin-4-yl-amino-methyl)-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

163)
(2R,3S,4R,5S,8R,10R,11R,12S,13S,14R)-13-[(2,6-dideoxy-3-C-methyl-3-O-methyl-4-C-[(6-chloro-pyridin-3-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

164)
(2R,3S,4R,5S,8R,10R,11R,12S,13S,14R)-13-[(2,6-dideoxy-3-C-methyl-3-O-methyl-4-C-(tetrahydropyrrolyl-methyl)-α-L- ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

165)
(2R,3S,4R,5S,8R,10R,11R,12S,13S,14R)-13-[(2,6-dideoxy-3-C-methyl-3-O-methyl-4-C-[(5-hydrosulphonyl-1H-[1,2,4]triazol-3-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

166)
13-[(2,6-dideoxy-3-C-methyl-3-O-methyl-4-C-[(2-amino-5-chloropyridinyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

167)
13-[(2,6-dideoxy-3-C-methyl-3-O-methyl-4-C-[N-ethyl-methylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

168)
13-[(2,6-dideoxy-3-C-methyl-3-O-methyl-4-C-[(diallylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

169) 13-[(2,6-dideoxy-3-C-methyl-3-O-methyl-4-C-[(2,2,2-trifluoroacetamido)methyl]α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

170) 13-[(2,6-dideoxy-3-C-methyl-3-O-methyl-4-C-[(3-amino-2chloropyridinyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

171) 13-[(2,6-dideoxy-3-C-methyl-3-O-methyl-4-C-[(benzamido)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

172) 13-[(2,6-dideoxy-3-C-methyl-3-O-methyl-4-C-[(3-trifluoromethylbenzylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino-β-D-xylo-hexopyranosy]oxy]-(2R,3S,4R,5S,8R,10R,11R,12S,13S,14R)-1-oxa-7-azacyclopentadecan-15-one;

173) 13-[(2,6-dideoxy-3-C-methyl-3-O-methyl-4-C-[(3-bromophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

174) 13-[(2,6-dideoxy-3-C-methyl-3-O-methyl-4-C-[(3-methoxyphenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

175) 13-[(2,6-di deoxy-3-C-methyl-3-O-methyl-4-C-[(p-iodophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

176) 13-[(2,6-dideoxy-3-C-methyl-3-O-methyl-4-C-[(2,4-dinitrophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

177) 13-[(2,6-dideoxy-3-C-methyl-3-O-methyl-4-C-[(2,4-dimethylphenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

178) 13-[(2,6-dideoxy-3-C-methyl-3-O-methyl-4-C-[(3,5-di(trifluoromethyl)phenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

179) 13-[(2,6-dideoxy-3-C-methyl-3-O-methyl-4-C-[(2,4-dichlorophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

180) 13-[(2,6-dideoxy-3-C-methyl-3-O-methyl-4-C-[(2-chlorophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

181) 13-[(2,6-dideoxy-3-C-methyl-3-O-methyl-4-C-[(allopurinol)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

182) 13-[(2,6-dideoxy-3-C-methyl-3-O-methyl-4-C-[(1,2,4-triazolyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one;

183) 13-[(2,6-dideoxy-3-C-methyl-3-O-methyl-4-C-[(2-methylimidazolyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one; or 184) 13-[(2,6-dideoxy-3-C-methyl-3-O-methyl-4-C-[(N-methyl-2-hydroxyethylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-(2R,3S,4R,5S,8R,10R,11R,12S,13S,14R)-1-oxa-7-azacyclopentadecan-15-one.

The present disclosure further provides a pharmaceutically acceptable salt of the compound described above. Preferably, the salt is prepared from the compound and an acid, and the acid is preferably selected from one or more of a group consisting of hydrochloric acid, oxalic acid, maleic acid, fumaric acid, citric acid, malic acid, isethionic acid, tartaric acid, methanesulfonic acid, ethanesulfonic acid, hydrobromic acid, sulfuric acid, phosphoric acid, acetic acid, propionic acid, lactic acid, trifluoroacetic acid, benzoic acid, and p-toluenesulfonic acid.

The present disclosure further provides a pharmaceutical composition for use in treatment of bacterial infections or protozoal infections in mammals, birds, or fish, comprising a therapeutically effective amount of the compound described above or a pharmaceutically acceptable salt thereof, and a pharmaceutically acceptable carrier thereof.

The present disclosure further provides use of the compound described above or a pharmaceutically acceptable salt thereof in preparation of medicaments for the treatment of bacterial infections or protozoal infections in mammals, birds, or fish.

The following synthetic routes describe the compounds as shown by formula (I) according to the present disclosure. All materials involved are prepared according to the process schematically shown by the synthetic routes, or process well known to one ordinary skilled in the organic chemistry field, or commercially available. All titled compounds according to the present disclosure are prepared according to the process schematically shown by the synthetic routes, which are well known to one ordinary skilled in the organic chemistry field.

The compound shown by formula (I) according to the present disclosure can be prepared through the following route.

The preparation process according to the present disclosure:

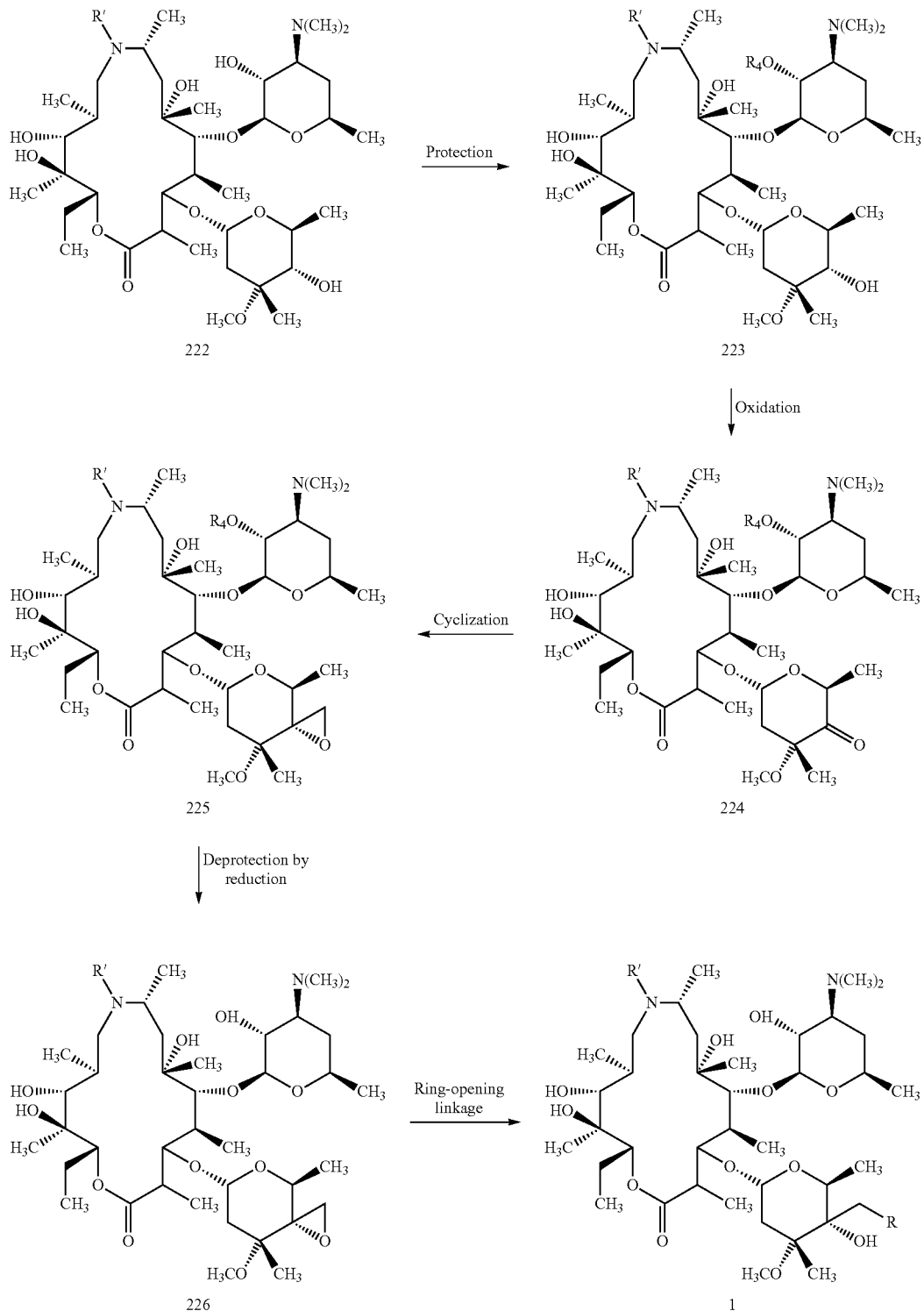

Starting compound 222 can be synthesized according to processes recited in literature (Synthesis of 9-Deoxo-8a-aza-8a-homoerythromycin A by One-step, Chinese Journal of Synthetic Chemistry, volume 18, 2011, pages 265-268) and Chinese Patent CN1425022A, which are well known to the person skilled in the art.

According to an embodiment of the present disclosure, C-2' hydroxyl in compound 222 can be selectively protected by treating compound 222 with equivalent acetic anhydride in dichloromethane without external alkali, thus obtaining a compound of general formula 223 in which $R_4$ is acetyl. The compound of general formula 223 can be treated with methanol for 10-48 h at a temperature in a range from 23 to 65° C., so that acetyl protecting group can be removed. C-2' hydroxyl can also be protected by other hydroxyl protecting group well known to the person skilled in the art, such as carboxybenzyl (Cbz). In the meantime, C-4" hydroxyl would also be protected, which, however, does not influence subsequent experiments. C-2' hydroxyl can be selectively protected using Cbz in one step by treating the compound of formula 222 with benzyl chloroformate in tetrahydrofuran and water. The Cbz group can be removed through conventional catalytic hydrogenation, or by reaction in a suitable organic solvent known in the art at a temperature in a range from room temperature to 100° C. for 2 h-5 days. In the following description, C-2' hydroxyl and C-4" hydroxyl are protected or deprotected in manners deemed suitable by the person skilled in the art.

C-4" hydroxyl of the compound of general formula 223 is oxidized. The oxidation of C-4" hydroxyl is the focus of the synthesis of parent nucleus. C-4" hydroxyl of the compound of general formula 223 is oxidized to a corresponding ketone through process well known to the person skilled in the art, including one or more processes described in Journal of Anti-biotics, 1988, pages 1029-1047. For example, the ketone of general formula 224 can be prepared from dimethylsulfoxide and suitable activating agent. Conventional reaction conditions for oxidation include: for example, a) Corey-kim oxidation (J. Med. Chem, 2001, 44 (24): 4137-4156), b) Jone's reagent (Bioorg. Med. Chem. Lett, 2006, 16 (3): 569-572), c) Dess-martin's reagent (US 2004/0254126), d) modified Pfitzner-maffat oxidation (J. Med. Chem, 1998, 41 (21): 4080-4100), e) Moffatt oxidation, in which N-ethyl-N'-(N,N-dimethylaminopropyl)carbodiimide and dimethylsulfoxide react under the presence of trifluoroacetic acid pyridine onium salt, or f) Swern oxidation, in which oxalic acid chloride or trifluoroacetic anhydride reacts with dimethylsulfoxide in dichloromethane, followed by the addition of triethylamine.

The oxidation of the compound of general formula 223 is preferably conducted by using dimethylsulfoxide, trifluoroacetic anhydride, and triethylamine. In the oxidation process, the protected compound is dissolved in a suitable solvent, such as dichloromethane, acetone, ethyl acetate, acetic acid isopropyl ester, and the like, preferably dichloromethane, at a temperature in a range from −78 to 50° C., preferably in a range from −78 to 60° C. Subsequently, trifluoroacetic anhydride is added, preferably dropwise, and reacted for 0-3 h. Afterwards, triethylamine is added dropwise and reacted for 0-3 h. After the reaction is completed, an oxide, i.e. compound of general formula 224, can be obtained.

Compound of general formula 225 can be obtained through either of the two following processes.

In a first process (process A), compound of general formula 224 is treated with $(CH_3)_3S(O)X_2$ wherein $X_2$, is halogen, preferably iodine, —$BF_4$ or —$PF_6$, at a temperature in a range from 0 to about 60° C., under the presence of an alkali, such as potassium tert-butoxide, sodium tert-butoxide, sodium ethoxide, sodium hydride, 1,1,3,3-tetramethyl guanidine, 1,8-diazabicyclo[5.4.0]undec-7-ene, 1,5-diazabicyclo[4.3.0]non-5-ene, potassium ethoxide, or sodium methoxide, preferably a sodium-containing alkali, such as sodium hydride, in a solvent, such as tetrahydrofuran, an ether solvent, N,N-dimethylformamide, or dimethylsulfoxide, or mixture of two or more of the above solvents, whereby compound of general formula 225 is obtained.

In a second process(process B), compound of general formula 224 is treated with $(CH_3)_3SX_2$ wherein X, is halogen, —$BF_4$ or —$PF_6$, preferably —$BF_4$, at a temperature in a range from −78 to about 60° C., under the presence of alkali, such as potassium tert-butoxide, sodium tert-butoxide, sodium ethoxide, sodium hydride, 1,1,3,3-tetramethyl guanidine, 1,8-diazabicyclo[5.4.0]undec-7-ene, 1,5-diazabicyclo[4.3.0]non-5-ene, potassium ethoxide, potassium hexamethyldisilazide (KHMDS), or sodium methoxide, preferably KHMDS, in a solvent, such as tetrahydrofuran, an ether solvent, N,N-dimethylformamide, or dimethylsulfoxide, or mixture of two or more of the above solvents, whereby compound of general formula 225 is obtained.

The term "halogen", as used herein, unless otherwise indicated, includes fluorine, chlorine, bromine, or iodine.

The term "alkyl", as used herein, unless otherwise indicated, includes saturated monovalent hydrocarbon residue having straight, cyclic or branched moieties, or mixtures thereof. It is to be understood that where a cyclic moiety is mentioned, there are at least three carbon atoms present in said alkyl. Such cyclic moieties include cyclopropyl, cyclobutyl, and cyclopentyl.

The term "alkoxy", as used herein, unless otherwise indicated, includes —O-alkyl where alkyl is as defined above.

The term "aryl", as used herein, unless otherwise indicated, includes an organic residue derived from an aromatic hydrocarbon by removal of one hydrogen from the aromatic hydrocarbon, such as phenyl or naphthyl.

The term "5-10 membered heteroaryl", as used herein, unless otherwise indicated, includes aromatic heterocyclic groups containing one or more heteroatoms independently selected from O, S and N, wherein each heterocyclic group has 5-10 atoms in its ring system. Examples of suitable 5-10 membered heteroaryl groups include pyridyl, furyl, thienyl, pyrazolyl, (1,2,3)- and (1,2,4)-triazolyl, pyrazinyl, tetrazolyl, furyl, thienyl, isoxazolyl, oxazolyl, pyrrolyl, and thiazolyl.

The compounds of the present disclosure may have asymmetrical carbon atoms and therefore exist in different enantiomeric and diastereomeric forms. Diastereomeric mixtures can be separated into individual diastereomers based on the physical and chemical differences by methods well known in the art, such as chromatography or fractional crystallization. An enantiomer can be separated by converting the enantiomeric mixture into a diastereomeric mixture by reaction with a suitable optically active compound (such as alcohol), separated the diastereomers and converting individual diastereomers to the corresponding pure enantiomers. The use of all such isomers, including diastereomeric mixtures and pure enantiomers, are considered to be part of the present disclosure.

Preferably, the bacterial and protozoal infections of the present disclosure, as well as human diseases related to such infections, include the following: pneumonia, trachitis, bronchitis, otitis media, sinusitis, amygdalitis, pharyngitis and nephritis related to infection by phthogenic *Streptococcus suis, Haemophilus influenza, Moraxella, Staphylococcus aureus, Legionella, Actinobacillus, Mycoplasma,* and *Chlamydia*; fever and skin and soft tissue infections, abscesses and osteomyelitis related to infection by pathogenic *Staphylococcus, Streptococcus,* and *Corynebacterium*; diseases of the genitourinary system, such as urethritis, cervicitis, gonorrhea infection, and sexually transmitted diseases, related to infection by pathogenic *Staphylococcus, Enterococcus, Chlamydia, Spirochaeta, Mycoplasma,* and *Neisseria*; Lyme disease related to infection by *borrelia burgdorferi*; conjunctivitis, keratitis and dacryocystitis related to infection by *Chlamydia trachomatis, Neisseria gonorrhoeae, Staphylococcus aureus, Streptococcus pneumonia, Streptococcus pyogenes, Hemophilus influenza,* or *Listeria* spp.; gastroenteritis related to infection by *Campylobacter jejuni* or anabrosis related to infection by *Helicobacter pylori*; intestinal protozoa related to infection by *Crytosporiduum* spp.; odontogenic infection related to infection by *Viridans streptococci*; persistent cough related to infection by *Bordetella pertussis*; gas gangrene related to infection by *Clostridium perfringens* or *Bacteroids* spp.; and arteriosclerosis related to infection by *Helicobacter pylori* or *Chlamydia pneumoniae*.

Preferably, the animal bacterial infections and protozoal infections that can be prevented and treated according to the present disclosure, as well as diseases related to such infections, include the following: bovine respiratory diseases related to infection by *Pasteurella hemolytica, Pasteurella multocida, Mycoplasma bovis,* or *Bordetella* spp.; bovine enteric diseases related to infection by *Escherichia coli* or protozoa (such as coccidia); dairy cow mastitis related to infection by *Staphylococcus aureus, Streptococcus uberis, Streptococcus agalactiae, Streptococcus dysgalactiae, Klebsiella* spp., *Corynebacterium* and *Enterococcus*; bovine or swine hysteritis related to infection by *Escherichia coli*; infectious conjunctivitis related to infection by *Moraxella bovis*; cow premature abortion related to infection by protozoa (i.e., nesporium); swine respiratory diseases related to infection by *Actinobacillus pleuropneumoniae, Pasteurella multocida, Haemophilus,* and *Mycoplasma*; blood protozoonoses related to infection by protozoa (such as toxoplasm, eperythrozoon); swine enteric diseases related to infection by *E. coli, Salmonella* and *spirochaeta*; swine septicemia, skin inflammation, and joint swell, necrosis and pyosis related to infection by *Bacillus etysipelatos-suis, Streptococcus suis* and *Bacillus anthracis*; urinary tract infections in dogs and cats related to infection by *E. coli*; skin and soft tissue infections in dogs and cats related to infection by *Staph. epidermidis, Staph. intermedius,* coagulase neg. *Staph* or *P. multocida*; dental or mouth infections in dogs and cats related to infection by *Alkaligenes. Bacteroides, Clostridium, Enterobacter* spp., *Eubacterium, Peptostreptococcus, Porphyromonas* and *Prevotella*; enteric diseases in birds related to infection by *E. coli, Salmonella* and *Clostridium welchii*; septicemia and parenchymatous organs and mucous membrane inflammations of skin, soft tissues and internal organs in birds related to infection by *E. coli, Pasteurella, Staphylococcus* and *Streptococcus*; protozoosis related to protozoa (such as *coccidium* and *Leucocytozoo-*

*sis*); and respiratory diseases related to infection by *Mycoplasma, Haemophilus* and *E. coli*.

A therapeutic dose of the effective amount according to the present disclosure is 2-50 mh/kg per single dose.

The term "pharmaceutically acceptable salt(s)" as used herein, unless otherwise indicated, includes salts of acidic or basic groups which may be present in the compounds of the present disclosure. The compounds of the present disclosure that are basic in nature are capable of forming a wide variety of salts with various inorganic or organic acids. Acids that may be used to prepare the pharmaceutically acceptable salts of such basic compounds are those that form acid addition salts, i.e., salts containing pharmaceutically acceptable anions, such as, formate, acetate, propionate, lactate, citrate, tartrate, oxalate, malate, hydrochloride, sulfate, nitrate, hydrosulfate, phosphate, acid phosphate, nicotinate, salicylate, pantothenate, ascorbate, succinate, maleate, gentisic acid, fumarate, gluconate, glucarate, saccharate, benzoate, glutamate; mesylate, esilate, benzene sulfonate, tosilate, and various amino acids according to the present disclosure. The compounds of the present disclosure that are acid in nature are capable of forming basic salts with various pharmaceutically acceptable positive ions. The salts include alkali metals and alkaline earth, such as calcium, magnesium, sodium and potassium, and the like, According to the present disclosure, the pharmaceutical composition for treatment of bacterial or protozoal infections in mammals, birds, or fish, comprises the compound of formula (I) or a pharmaceutically acceptable salt thereof as active ingredient, and a pharmaceutically acceptable carrier. The pharmaceutically acceptable carrier refers to any diluent or adjuvant that can be used in pharmaceutical field.

Dosage form of the pharmaceutical composition of the present disclosure can be oral preparations, injection, or external preparations.

Preferably, the oral preparations according to the present disclosure can be powder, tablets, capsules, granules, liquores, and suspensoid. The injection preparations can be powder injection, emulsion, suspensoid, and liquors. The external preparations can be ointment and drops.

The carrier in the pharmaceutical composition according to the present disclosure refers to adjuvant ingredients necessary in the preparations in the pharmaceutical field, including diluents, cosolvent, antioxidant, corrigent, preservative, excipient, and coagulant.

DETAILED DESCRIPTION OF THE EMBODIMENTS

Examples are provided to further illustrate the process and intermediates according to the present disclosure. Nevertheless, the following examples are not intended to limit the scope of the present disclosure.

A synthetic route involved in examples 1 to 80 of the present disclosure is shown as follows.

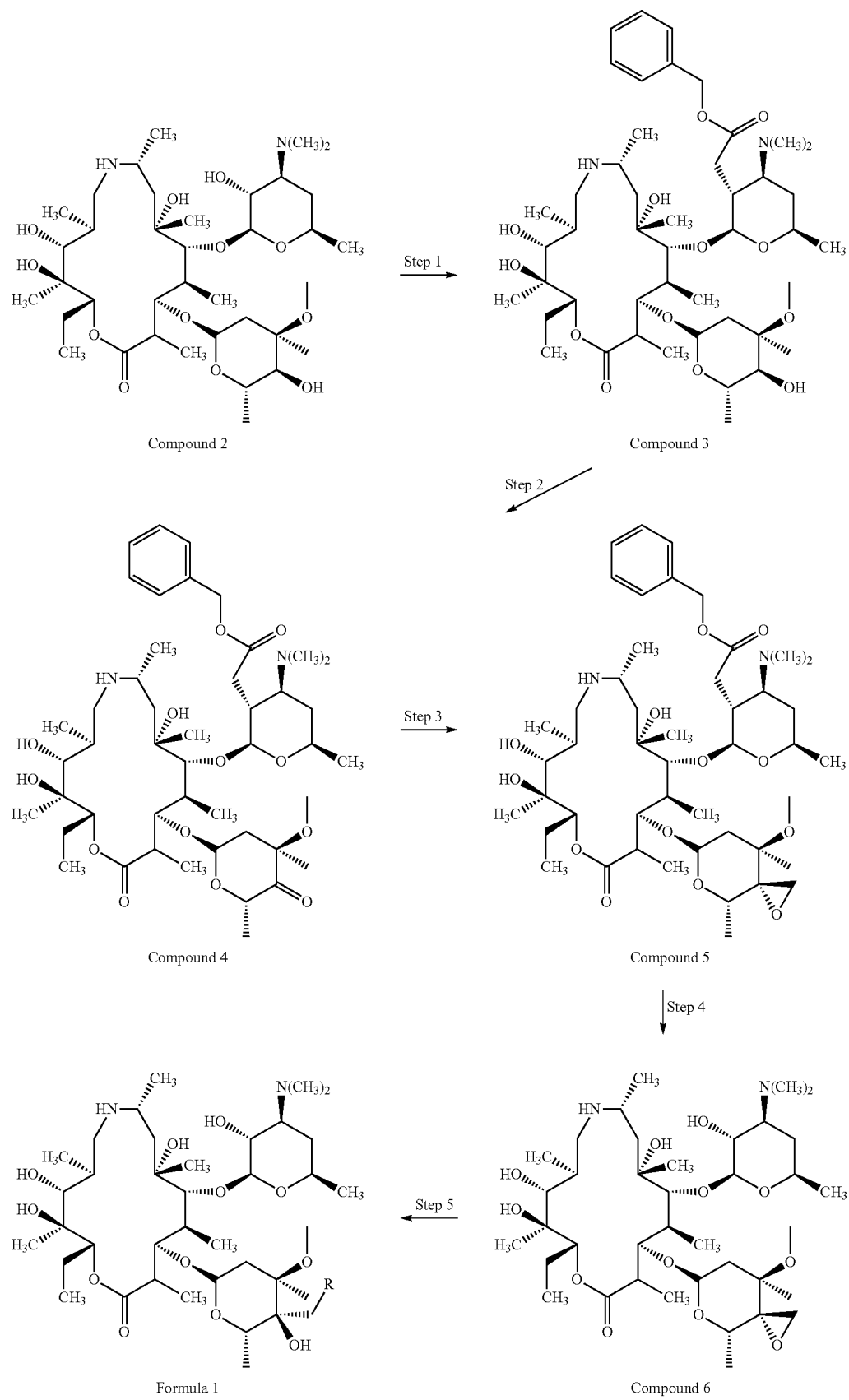

Example 1

A cryostat was turned on, and the temperature was set at −12° C. 500 ml dichloromethane was measured with a 1 L graduated cylinder and added into a 1.0 L three-necked bottle. The three-necked bottle was placed in the cryostat to be cooled under agitation. 50 g (0.068 mol) of compound 2 was weighed with a counter balance and added into the reaction flask, and 300 ml of dichloromethane was measured with the 1 L graduated cylinder and added therein. The mixture was stirred, dissolved and cooled. An inner temperature of the reaction flask was cooled to 0-5° C. To the reaction solution, the temperature of which is kept at 0-5° C., was slowly added dropwise a mixed solution of 11.98 ml of benzyl chloroformate and 60 ml of dichloromethane. After the addition of the mixed solution, the reaction was carried out under the same temperature for 1 h. The reaction progress was monitored through thin layer chromatography (developing solvent: dichloromethane/methanol=10:1, with addition of two drops of ammonia). After the reaction was completed, the resulting reaction solution was concentrated under vacuum (with a temperature being ≤50° C. and a vacuum degree being ≤−0.086 Mpa) to give about 300 ml of compound 3.

TLC Rf=0.42 (dichloromethane:methanol=7:1).
ESI/MS: m/z 869[M+H]$^+$.

Example 2

A low temperature cooling device was turned on, and the temperature was set at −75° C. Temperature was cooled to a range from −70 to −60° C. The 300 ml compound 3 liquid obtained from the concentration according to example 1 was transferred to a 1.0 L three-necked reaction flask. 106.46 ml (117.11 g or 1.498 mol) of dimethyl sulfoxide was added into the reaction flask under room temperature (25-30° C.). After dimethyl sulfoxide was added, the reaction flask was placed in the cryostat to be cooled under agitation to a temperature in a range from −70 to 60° C. 21.55 ml (0.152 mol or 31.865 g) of trifluoroacetic anhydride was slowly added dropwise, a dropping speed thereof being controlled, so that a temperature of the reaction solution can be maintained in a range from −65 to −60° C. The reaction was carried out under the same temperature for 0.5 h. Under the condition that the temperature of the reaction solution was maintained in the range from −65 to −60° C., 47.3 ml (0.339 mol, 34.35 g) of triethylamine was slowly added dropwise, and then stirred for 0.5 h under the same temperature. After the completion of the reaction, the reaction solution was warmed to the room temperature. The reaction liquid at room temperature (20-30° C.) was transferred to a 2.0 L separating funnel, into which 350 ml of purified water was added. After extraction, a water layer was discarded and an organic layer was obtained. The organic layer was extracted again with 250 ml of saturated sodium bicarbonate solution, from which an organic layer was obtained and a water layer was discarded. The organic layer obtained was extracted again with 350 ml of purified water, from which a water layer was discarded and an organic layer is obtained. The organic layer was transferred to a 1.0 L beaker, into which 20 g of anhydrous magnesium sulfate was added. After agitation for 20 minutes, the mixture in the beaker is dried and dehydrated. Then, magnesium sulfate was filtered out, and pale yellow filtrate was obtained. The pale yellow filtrate was concentrated to a volume of 125 ml under vacuum, with a temperature being ≤60° C. and a vacuum degree being ≤−0.086 Mpa. To the concentrate, was added 135 ml of isopropanol, and concentrated again to a volume of 135 ml. The liquid finally obtained from the concentration was transferred into the 1.0 L three-necked reaction flask. 700 ml of tert-butyl methyl ether was added into the reaction flask, and 11.2 ml (0.1497 mol, 17.07 g) of trifluoroacetic acid was slowly added therein dropwise at room temperature. The resulting mixture was crystallized under stirring at room temperature. After suction filtration, the filter cake was washed with n-heptane (200 ml×2) by stirring for 30 min. The filter cake was dried by forced air at 30° C., to afford 8.2 g of compound 4, with a yield of 82.2% and HPLC purity of 91% (applying HPLC-Waters Symmetry C8, 15 cm×3.9 mm column, Mobile Phase:methanol:ammonium acetate (25:75), Flow rate: 2.0 mL/min, Residence time: 5.07 min).

TLC Rf=0.39 (dichloromethane:methanol=7:0).
ESI/MS: m/z 867[M+H]$^+$.

Example 3

To a 3.0 L beaker were added 50 g (0.0456 mol) of compound 4 of example 2 and 80 ml of dichloromethane. After uniform mixing, the solution was dried with 15 g of anhydrous magnesium sulfate for 20 min and then filtered by suction filtration. The filtrate was dried for the second time with 7 g of anhydrous magnesium sulfate for 20 min and then filtered by suction filtration. The filter residue, which was washed with dichloromethane, and the filtrate, which was refilled with dichloromethane to a volume of 160 ml (the measured content of moisture in the filtrate should be less than 0.3%) were reserved for later use. A low temperature cooling device was turned on and set at −8° C. 170 ml of tetrahydrofuran (dried with anhydrous magnesium sulfate for 30 min and filtered by suction filtration) was added into a 1.0 L three-necked bottle. The three-necked bottle was placed in a cryostat to be cooled under agitation to a temperature in a range from −5 to 0° C. 20 g (0.1273 mol) of trimethylsulfonium bromide was added into the three-necked bottle, and 20 g (0.11.786 mol) of potassium tert-butoxide was added therein at −5-0° C. After being vacuumized by a circulating water pump, the three-necked bottle was filled with nitrogen. The reaction mixture was stirred for for 15 min under nitrogen atmosphere. The temperature of the low temperature cooling device was adjusted to −75° C., and an inner temperature thereof was reduced to a range from −65 to −60° C. The solution, which has been deoxidized and dried, was slowly added into the reaction flask dropwise, meanwhile timekeeping begun. In this course, the temperature of the reaction solution was kept in a range from −65 to −60° C. After the addition of the solution, the reaction was carried out at −65 to −60° C. till the timekeeping reached 3 h. Reaction progress was monitored by thin layer chromatography (developing solvent: dichloromethane/methanol=10:1, with addition of two drops of ammonia). After the reaction was completed, to the reaction mixture was added a solution of 21.5 g (0.405 mol) of ammonium chloride in 120 ml of water. The resulting mixture was stirred for 15 min at 5-10° C. After stratification, the water layer was extracted once with 200 ml of dichloromethane; and organic phases were combined, and washed with water for four times (4×100 ml). The organic layer was concentrated under vacuum until no more distillate was observed.Remaining solvent was vaporized by being substituted with 200 ml methanol. After two substitutions, the solution was concentrated, thereby obtaining compound 5.

TLC Rf=0.55(dichloromethane:methanol=8:1).
ESI/MS: m/z 881 [M+H]$^+$.

Example 4

Compound 5 prepared in example 3 was dissolved in 350 ml of methanol and transferred to a 1.0 L three-necked bottle. 16 g of palladium and 142 g (0.2246 mol) of ammonium formate were added into the three-necked bottle. The reaction was carried out at 50° C. for 2 h. Reaction progress was monitored by thin layer chromatography (developing solvent: dichloromethane/methanol=10:1, with addition of two drops of ammonia). After the reaction was completed, the reaction solution was cooled to lower than 30° C., and then filtered by suction. The filtrate was concentrated under vacuum until about 200 ml of mixture remained, and the filter cake was kept sealed with water. The concentrate was slowly added into 550 ml of water dropwise within 20 min, and crystallized under stirring for 1 h. After suction filtration, the filter cake was washed with methanol/water (1:3), and then dried, to afford compound 6 (applying WATERS ACQUITY UPLC BEH C18 chromatographic column (2.1×50 mm, 1.7 μm); Mobile phase: acetonitrile-0.01 moL/L ammonium acetate in water (55:45), Flow rate: 0.20 mL/min, Residence time: 2.77 min, Detecting wavelength: 210 nm, Column temperature: 40° C., and Inj. Vol: 2.5 μl).

TLC Rf=0.45(dichloromethane:methanol=7:1).
ESI/MS: m/z 747[M+H]$^+$.

Example 5

General Preparation Process 1
Preparation of (2R,3S,4R,5S,8R,10R,11R,12S,13S,14R)-13-[(2,6-dideoxy-3-C-methyl-3-O-methyl-4-C-[(cyclopropylamino)methyl]-α-L- ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one.

Compound 6 (0.5 g, 0.6698 mmol), potassium iodide (1.11 g, 0.698 mmol) and cyclopropylamine (2.43 mL, 2.00 g, 35 mmoL) were dissolved under vibration at 50° C. in 5 ml isopropanol in a 50 ml round-bottom flask, and the resulting mixture was stirred at 50° C. Reaction progress was monitored by TLC. After the reaction was completed, the resulting reaction mixture was concentrated, and the residue was dissolved in water (50 ml) and ethyl acetate (100 ml). After standing stratification, the water layer was washed with ethyl acetate (3×50 mL). The organic phases were combined, washed with saturated sodium bicarbonate solution (50 ml) and brine (40 ml), dried with anhydrous sodium sulfate, and filtered. The filtrate was concentrated under vacuum to afford crude product. The crude product was purified by silica gel chromatograph (gradient of eluents of methanol:dichloromethane:ammonia water from 4:95.6:0.4 to 6:93.5:04) to afford 0.38 g of the titled compound (2R,3S,4R,5S,8R,10R,11R,12S,13S,14R)-13-[(2,6-dideoxy-3-C-methyl-3-O-methyl-4-C-[(cyclopropylamino) methyl]-α-L- ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one.

TLC Rf=0.47(dichloromethane:methanol=5:1).
ESI/MS: m/z 805[M+H]$^+$.

General Preparation Process 2
Preparation of (2R,3S,4R,5S,8R,10R,11R,12S,13S,14R)-13-[(2,6-dideoxy-3-C-methyl-3-O-methyl-4-C-[(butylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one, Compound 6 (0.5 g, 0.6698 mmol), tetrabutylammonium iodide (0.74, 2.0 mmoL) and n-butylamine (0.395 mL, 0.2938, 4 mmoL) were dissolved under vibration in 5 ml methanol at 50° C., and the resulting mixture was stirred at the same temperature. Reaction progress was monitored by TLC. After the reaction was completed, the resulting reaction mixture was concentrated, and residue was dissolved in 20 ml of water and 20 ml of ethyl acetate. After standing stratification, the water layer was washed with ethyl acetate (3×20 ml). The organic extractants were combined and washed with 40 ml of brine, dried with anhydrous sodium sulfate, and filtered. The filtrate was concentrated under vacuum, thereby obtaining crude product. The crude product was purified by silica gel chromatograph (gradient of eluents of methanol:dichloromethane:ammonia water from 4:95.6: 0.4 to 6:93.5:0.4) to afford 0.0888 g of the titled compound (2R,3S,4R,5S,8R,10R,11R,12S,13S,14R)-13-[(2,6-dideoxy-3-C-methyl-3-O-methyl-4-C-[(butylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one.

TLC Rf=0.47(dichloromethane:methanol=5:1).
ESI/MS: m/z 819 [M+H]$^+$.

General Preparation Process 3
Preparation of (2R,3S,4R,5S,8R,10R,11R,12S,13S,14R)-13-[(2,6-dideoxy-3-C-methyl-3-O-methyl-4-C-[(propylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one.

Compound 6 (0.5 g, 06694 mmol) and n-propylamine (0.5 g) were dissolved under vibration in isopropanol (10 ml) at 50° C., and the resulting mixture was stirred at the same temperature for 48 h. Reaction progress is monitored by TLC. After the reaction was completed, the resulting reaction mixture was concentrated, and residue was added into saturated sodium bicarbonate solution (50 ml) and dichloromethane (80 ml). The mixture was vibrated uniformly, and stood to be stratified. The organic phase dichloromethane was washed with water (3×50 ml), dried with MgSO$_4$, and concentrated under vacuum to dryness. The resulting substance was dissolved in dichloromethane, and applied on GF254 silica gel. Thin layer chromatography separation was performed with an eluent of 4/1 cyclohexane/diethylamine or 4/1/0.01 dichloromethane/methanol/ammonia water. The chromatographic band corresponding to the desired product was scraped off and further purified by silica gel chromatography eluted with a mixture of dichloromethane/methanol/ammonia in a ratio of 4/1/0.01. The mobile phase was concentrated at 50° C. under vacuum and dried, thereby obtaining 0.16 g of (2R,3S,4R,5S,8R,10R,11R,12S,13S, 14R)-13-[(2,6-dideoxy-3-C-methyl-3-O-methyl-4-C-[(propylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one as pure amine.

TLC Rf=0.47(dichloromethane:methanol=5:1).
ESI/MS: m/z 807[M+H]$^+$.

Compounds according to examples 5 to 80 have structures shown by the following general formula 1.

General formula 1

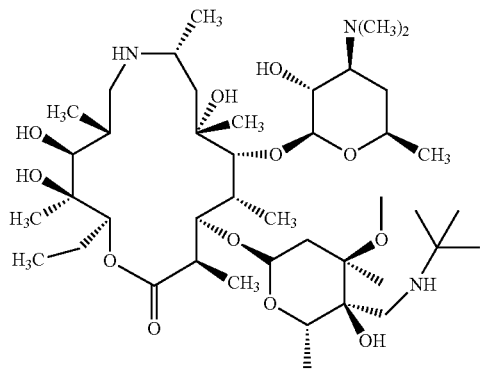

In examples 5 to 80, R is a group shown by Table 1, and nitrogen or sulfur in R is directly attached to methylene of R$_3$. R' in each of examples 5 to 80 is H. Specific reaction time for each of compounds of examples 6 to 80 prepared according to the above general preparation process 1, general preparation process 2 and general preparation process 3 of example 5 is shown in Table 1. In Table 1, data relating to structures, yields and mass spec are the data of the final compounds.

TABLE 1

| Example | Compound No. | R | Preparation process | Reaction time, h | Yield % | Mass spec M + H |
|---|---|---|---|---|---|---|
| 5 (general preparation process 3) | syzx-1 | n-propylamino | general preparation process 3 | 48 | 50 | 807 |
| 5 (general preparation process 2) | syzx-2 | n-butylamino | general preparation process 2 | 53 | 45 | 819 |
| 6 | syzx-3 | diethylamino | general preparation process 1 | 36 | 60 | 820 |
| 7 | syzx-4 | phenylamino | general preparation process 1 | 36 | 58 | 840 |
| 8 | syzx-5 | morpholinyl | general preparation process 1 | 36 | 42 | 834 |
| 5 (general preparation process 1) | syzx-6 | cyclopropylamino | general preparation process 1 | 36 | 46 | 805 |
| 9 | syzx-7 | pyrryl | general preparation process 1 | 36 | 59 | 814 |
| 10 | syzx-8 | 4-fluorobenzylamino | general preparation process 1 | 36 | 58 | 872 |
| 11 | syzx-9 | 1-imidazolyl | general preparation process 2 | 36 | 32 | 815 |
| 12 | syzx-10 | ethylamino | general preparation process 2 | 36 | 40 | 792 |
| 13 | syzx-11 | isopropylamino | general preparation process 2 | 48 | 33 | 806 |
| 14 | syzx-12 | isobutylamino | general preparation process 2 | 48 | 35 | 820 |
| 15 | syzx-14 | tert-butylamino | general preparation process 1 | 48 | 51 | 820 |
| 16 | syzx-15 | piperidinylamino | general preparation process 1 | 48 | 55 | 832 |
| 17 | syzx-17 | cyclopropylmethylamino | general preparation process 3 | 48 | 70 | 818 |
| 18 | syzx-18 | 4-methoxybenzylamino | general preparation process 2 | 48 | 55 | 884 |
| 19 | syzx-20 | 4-chlorobenzylamino | general preparation process 3 | 48 | 52 | 888 |
| 20 | syzx-21 | 3-pyridinylmethylamino | general preparation process 3 | 48 | 60 | 855 |
| 21 | syzx-22 | (3-ethoxypropyl)amino | general preparation process 3 | 48 | 33 | 850 |
| 22 | syzx-24 | dimethylamino | general preparation process 1 | 48 | 33 | 792 |
| 23 | syzx-25 | (2-methoxyethyl)amino | general preparation process 3 | 48 | 44 | 822 |
| 24 | syzx-27 | 2-methoxybenzyl-amino | general preparation process 3 | 72 | 50 | 884 |
| 25 | syzx-29 | 2-[(N-methyl)amino]-ethyl)amnino | general preparation process 3 | 72 | 33 | 821 |

TABLE 1-continued

| Example | Compound No. | R | Preparation process | Reaction time, h | Yield % | Mass spec M + H |
|---|---|---|---|---|---|---|
| 26 | syzx-30 | cyclopentylamino | general preparation process 1 | 72 | 35 | 832 |
| 27 | syzx-31 | 2,4-difluoro-benzyl-amino | general preparation process 3 | 72 | 36 | 890 |
| 28 | syzx-32 | 6-chloro-pyridazin-3-yl-amino | general preparation process 1 | 72 | 44 | 876 |
| 29 | syzx-34 | (1-methyl-3-phenyl)propyl-amino | general preparation process 1 | 72 | 23 | 896 |
| 30 | syzx-35 | 3-methoxybenzyl-amino | general preparation process 3 | 72 | 26 | 884 |
| 31 | syzx-37 | 2,2,2-trifluoroacetyl-amino | general preparation process 2 | 72 | 56 | 860 |
| 32 | syzx-38 | 2-chloro-pyridin-4-yl-amino | general preparation process 1 | 72 | 60 | 875 |
| 33 | syzx-39 | 4-formyl-benzyl-amino | general preparation process 1 | 72 | 23 | 898 |
| 34 | syzx-40 | propargyl-amino | general preparation process 1 | 72 | 45 | 802 |
| 35 | syzx-41 | butyrate-2-amino | general preparation process 1 | 72 | 56 | 850 |
| 36 | syzx-42 | butyrate-4-amino | general preparation process 1 | 72 | 60 | 850 |
| 37 | syzx-46 | 3-hydroxy-propylamino | general preparation process 3 | 72 | 56 | 822 |
| 38 | syzx-47 | n-pentyl-amino | general preparation process 3 | 72 | 57 | 834 |
| 39 | syzx-48 | morpholin-4-yl-amino | general preparation process 1 | 72 | 23 | 849 |
| 40 | syzx-50 | butyrate-3-amino | general preparation process 2 | 72 | 26 | 850 |
| 41 | syzx-51 | 1-hydroxymethyl-propylamino | general preparation process 1 | 72 | 66 | 836 |
| 42 | syzx-52 | 2-hydroxy-2-phenyl-ethylamino | general preparation process 1 | 72 | 77 | 884 |
| 43 | syzx-56 | 4-dimethoxy-butylamino | general preparation process 1 | 72 | 50 | 880 |
| 44 | syzx-57 | 3,4-dichloro-benzylamino | general preparation process 1 | 72 | 45 | 923 |
| 45 | syzx-58 | 2-methoxyethylamino | general preparation process 1 | 48 | 44 | 822 |
| 46 | syzx-59 | 1-methyl-4-dimethylamino-butylamino | general preparation process 1 | 72 | 36 | 905 |
| 47 | syzx-60 | (3-cyclohexylamino)propylamino | general preparation process 3 | 72 | 37 | 903 |
| 48 | Syzx-61 | 4-sulfamido-phenethylamino | general preparation process 3 | 72 | 38 | 947 |
| 49 | syzx-62 | 1-methyl-but-1-en-3-yne-amino | general preparation process 1 | 72 | 44 | 828 |
| 50 | syzx-63 | 1-methyl-butyl-amino | general preparation process 1 | 72 | 25 | 834 |

TABLE 1-continued

| Example | Compound No. | R | Preparation process | Reaction time, h | Yield % | Mass spec M + H |
|---|---|---|---|---|---|---|
| 51 | syzx-64 | 2-pyridin-4-yl-ethylamino | general preparation process 3 | 72 | 27 | 869 |
| 52 | syzx-65 | (2-methyl-pyrazin-5-yl-methyl)-amino | general preparation process 1 | 72 | 28 | 870 |
| 53 | syzx-66 | 3-methoxy-propyl-amino | general preparation process 1 | 72 | 29 | 836 |
| 54 | syzx-67 | cyclohexyl-methyl-amino | general preparation process 1 | 72 | 30 | 860 |
| 55 | syzx-68 | 2-fluoro-phenyl-amino | general preparation process 1 | 72 | 33 | 858 |
| 56 | syzx-69 | 3-morpholinyl-propyl-amino | general preparation process 2 | 72 | 63 | 891 |
| 57 | syzx-71 | 2-furfuryl-amino | general preparation process 1 | 72 | 38 | 844 |
| 58 | syzx-72 | 3-aminobenzyl-amino | general preparation process 1 | 72 | 39 | 869 |
| 59 | syzx-73 | phenylhydrazono | general preparation process 1 | 72 | 50 | 855 |
| 60 | syzx-74 | 2-(1H-indol-3-yl)-ethylamino | general preparation process 1 | 72 | 23 | 907 |
| 61 | syzx-75 | 3-chloropropyl-amino | general preparation process 3 | 72 | 46 | 840 |
| 62 | syzx-76 | 3,5-dimethoxyphenyl-amino | general preparation process 1 | 72 | 44 | 900 |
| 63 | syzx-77 | thienylformyloxymethyl-2-amino | general preparation process 1 | 72 | 43 | 904 |
| 64 | syzx-78 | 5-methylfurfurylamino | general preparation process 1 | 72 | 48 | 858 |
| 65 | syzx-81 | 4-fluoro-phenylhydrazono | general preparation process 1 | 72 | 25 | 873 |
| 66 | syzx-82 | benzyloxy-amino | general preparation process 1 | 72 | 30 | 870 |
| 67 | syzx-83 | p-methoxyphenyl-amino | general preparation process 1 | 72 | 21 | 870 |
| 68 | syzx-84 | 3,4-dimethylphenyl-amino | general preparation process 1 | 72 | 25 | 868 |
| 69 | syzx-86 | 5-fluoropyridin-2-yl-amino | general preparation process 1 | 72 | 16 | 859 |
| 70 | syzx-90 | 2-pyrrolyl-ethyl-amino | general preparation process 3 | 72 | 33 | 861 |
| 71 | syzx-91 | 2-pyridin-4-yl-ethylamino | general preparation process 1 | 72 | 32 | 869 |
| 72 | syzx-92 | 2-fluorobenzyl-amino | general preparation process 1 | 72 | 33 | 872 |
| 73 | syzx-93 | 2-piperidin-4-yl-methyl-amino | general preparation process 3 | 72 | 36 | 861 |
| 74 | syzx-94 | 5-chloro-o-methylphenyl-amino | general preparation process 1 | 72 | 11 | 888 |
| 75 | syzx-95 | 2-fluoro-phenyl-amino | general preparation process 1 | 72 | 10 | 858 |

TABLE 1-continued

| Example | Compound No. | R | Preparation process | Reaction time, h | Yield % | Mass spec M + H |
|---|---|---|---|---|---|---|
| 76 | syzx-96 | 2-fluoro-5-methylphenyl-amino | general preparation process 1 | 72 | 10 | 872 |
| 77 | syzx-97 | 2-methyl-4-chloro-phenyl-amino | general preparation process 1 | 72 | 13 | 888 |
| 78 | syzx-98 | N-methyl-butyl-amino | general preparation process 1 | 72 | 23 | 834 |
| 79 | syzx-99 | quiriolin-6-yl-amino | general preparation process 1 | 72 | 12 | 891 |
| 80 | syzx-100 | 1,2,2-trimethyl-propylamino | general preparation process 1 | 72 | 18 | 848 |

The following examples relate to compounds and preparation thereof when R' in formula (I) is n-propyl,

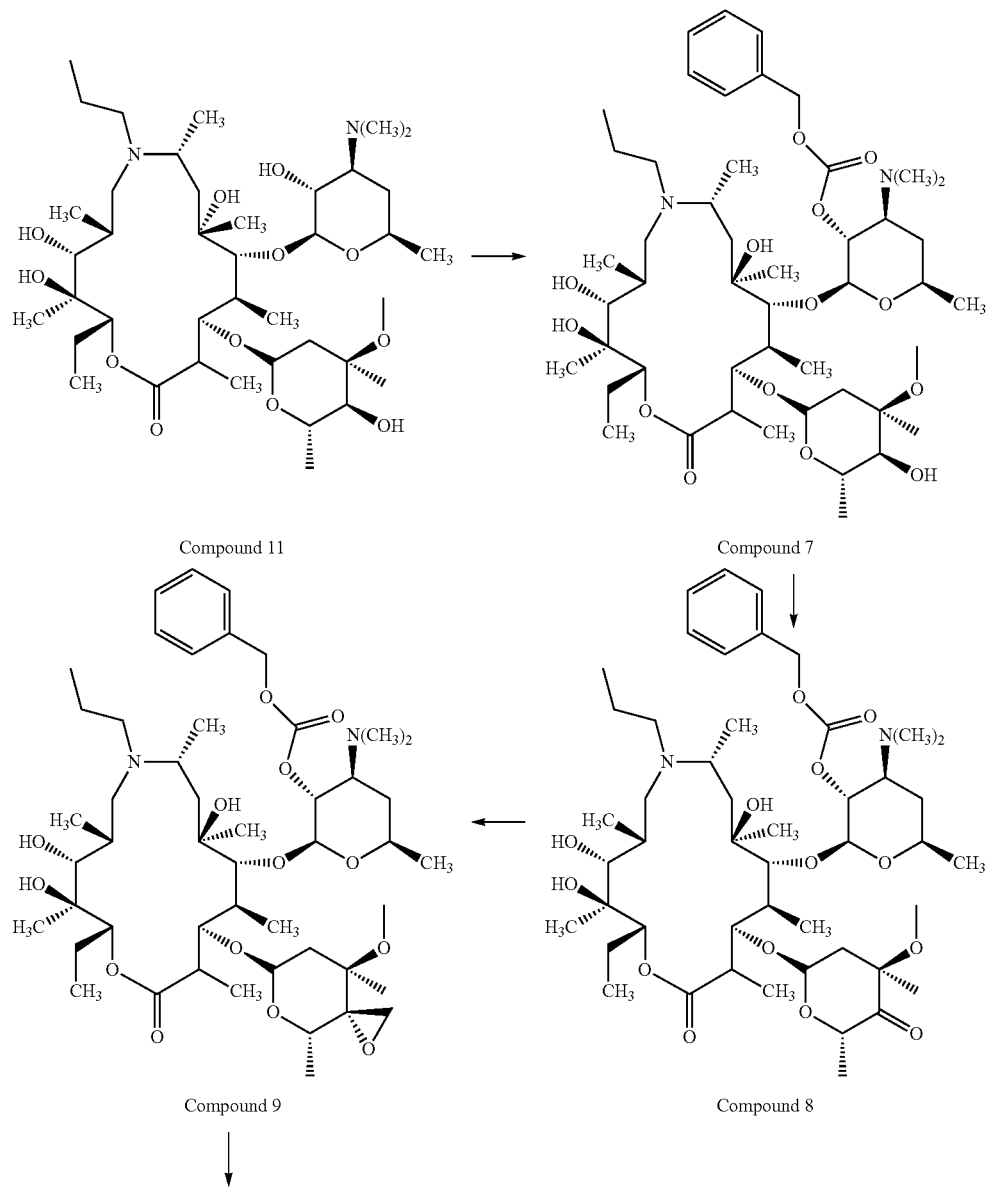

Compound 11 → Compound 7

Compound 9 ← Compound 8

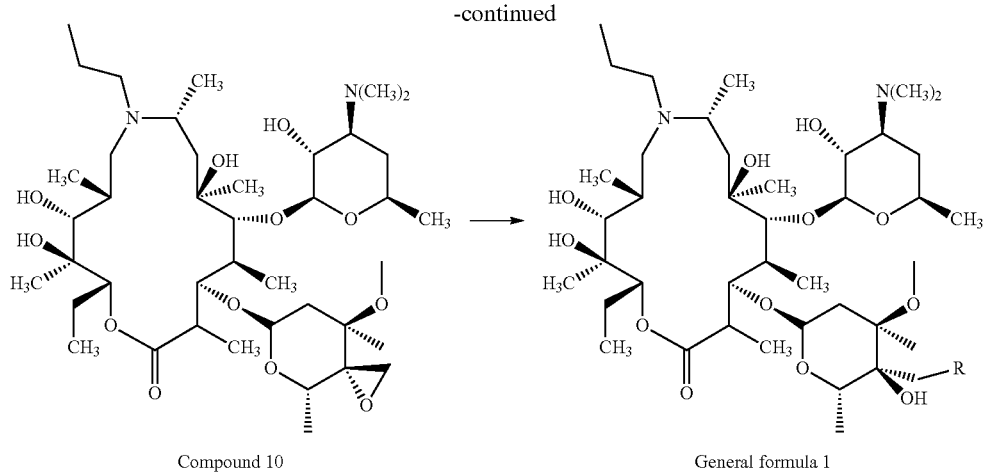

Compound 10   General formula 1

Example 81

600 ml of dichloromethane was added into a 2 L three-necked bottle. The three-necked bottle was placed in the cryostat to be cooled under agitation. 30 g (0.3861 mol) of compound 11, which was prepared according to the process as described in Chinese patent CN102239174A, was measured and added into the reaction flask to be dissolved under stirring, and then cooled to 0-5° C. To the reaction solution, the temperature of which is kept at 0-5° C., was slowly added dropwise a mixed solution of 6.8 ml (0.424 mol, 82.32 g) of benzyl chloroformate and 60 ml of dichloromethane. After the addition of the mixed solution, the reaction was carried out under 0-5° C. for 1 h. The reaction solution was concentrated under vacuum, with a temperature being ≤50° C. and a vacuum degree being ≤−0.086 Mpa, to give 180 ml of concentrate of compound 7. The concentrate of compound 7 was transferred to the 2 L three-necked reaction flask, into which 60.6 ml (66.6 g, 8.532 mol) of dimethyl sulfoxide was added at room temperature (20-30° C.). After dimethyl sulfoxide was added, the reaction flask was placed in the cryostat to be cooled under agitation to a temperature in a range from −70 to −60° C. 12.18 ml (0.864 mol, 181.32 g) of trifluoroacetic anhydride was slowly added dropwise, a dropping speed thereof being controlled, so that a temperature of the reaction solution can be maintained in a range from −65 to −60° C. The reaction was carried out at the same temperature for 0.5 h. Under the condition that the temperature of the reaction solution was maintained in the range from −65 to −60° C., 26.88 ml (1.932 mol, 195.3 g) of triethylamine was slowly added dropwise, and then stirred for 0.5 h at the same temperature.

After the reaction was completed, the reaction solution was warmed to the room temperature, and then transferred to a 2 L separating funnel, into which 210 ml of purified water was added. After extraction, an organic layer was obtained and a water layer was discarded. The organic layer was extracted again with 150 mL of saturated sodium bicarbonate solution, from which an organic layer was obtained and a water layer was discarded. Again, the organic layer obtained was extracted with 200 ml of purified water, from which a water layer was discarded and an organic layer was obtained.

The organic layer was transferred to a 1.0 L beaker, into which 120 g of anhydrous magnesium sulfate was added. After agitation for 20 minutes, the mixture in the beaker is dried and dehydrated. Then, magnesium sulfate was filtered out, and pale yellow filtrate was obtained. The pale yellow filtrate was concentrated under vacuum to dryness, with a temperature being ≤60° C. and a vacuum degree being ≤−0.086 Mpa, to afford compound 8.

TLC Rf=0.60 (dichloromethane:methanol=7:1).

ESI/MS: m/z 909[M+H]$^+$.

Example 82

170 ml of tetrahydrofuran was added into a 1.0 L three-necked bottle. The three-necked bottle was placed in a cryostat to be cooled under agitation to a temperature in a range of −5-0° C. Trimethylsulfonium bromide (0.12256 mol, 19.25 g) was added into the three-necked bottle, and potassium tert-butoxide (0.17156 mol, 19.25 g) was added therein at −5-0° C. The reaction mixture was stirred for 15 min under nitrogen atmosphere. An inner temperature was reduced to −70° C., and a dichloromethane solution of compound 8 prepared according to example 81 was slowly added dropwise into the three-necked bottle, meanwhile timekeeping begun. In this course, the temperature of the reaction solution was kept in a range from −65 to −60° C. After the addition of the solution, the reaction was carried out under nitrogen atmosphere till the timekeeping reached 3 h.

To the reaction solution was added a solution of 20.85 g (0.39 mol, 20.85 g) of ammonia chloride in 120 ml of water. The resulting mixture was stirred for 15 min at 5-10° C. After stratification, the water layer was extracted once with 200 ml of dichloromethane. The dichloromethane layer and the organic phase were combined, and washed with water (4×200 ml). The organic layer was concentrated under vacuum until no more distillate was observed. Remaining solvent was vaporized by being substituted with 200 ml methanol. After two substitutions, the solution was concentrated, thereby obtaining compound 9.

TLC Rf=0.58(dichloromethane:methanol=7:1).

ESI/MS m/z 923[M+H]$^+$.

Example 83

Compound 9 prepared in example 82 was dissolved in 170 ml of methanol. 16 g of palladium and 13.63 g (0.2164 mol, 13.63 g) of ammonium formate were added into the resulting solution. The reaction was carried out at 50° C. for 2 h. After the reaction was completed, the reaction solution was cooled and then filtered. The filter cake was kept sealed with water, and the filtrate was concentrated under vacuum until about 80 ml of mixture remained. The concentrate was slowly added dropwise into 250 ml of water within 20 min. The concentrate was regulated with 10% sodium hydroxide solution until the pH thereof reached 10.5±0.5, and crystallized under stirring for 1 h. After suction filtration, the filter cake was washed with methanol/water (1:3), and then dried under forced air at 40° C., thereby affording compound 10.

TLC Rf=0.33(dichloromethane:ethanol=7:1).

ESI/MS: m/z 789[M+H]$^+$.

Example 84

General Preparation Process (a)

Preparation of (2R,3S,4R,5S,8R,10R,11R,12S,13S,14R)-13-[(2,6-dideoxy-3-C-methyl-3-O-methyl-4-C-[(cyclopropylamino)-methyl]-α-L- ribopyranosyl)oxy]-2-ethyl-3,4,10-trihydroxy-8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one.

In a 50 ml round-bottom flask, compound 10 (0.5 g, 0.6698 mmol) prepared according to example 83, potassium iodide (1.11 g, 0.698 mmol) and cyclopropylamine (2.43 mL, 2.00 g, 35 mmoL) were dissolved under vibration at 50° C. in 5 ml of isopropanol, and the resulting mixture was stirred at 50° C. Reaction progress was monitored by TLC. After the reaction was completed, the resulting reaction mixture was concentrated, and the residue was dissolved in water (50 ml) and ethyl acetate (100 ml). After stratification, the water layer was washed with ethyl acetate (3×50 mL). The organic phases were combined, washed with saturated sodium bicarbonate solution (50 ml) and brine (40 ml), dried over anhydrous sodium sulfate, and filtered. The filtrate was concentrated under vacuum to afford a crude product. The crude product was purified by silica gel chromatograph (gradient of eluents of methanol:dichloromethane:ammonia water from 4:95.6:0.4 to 6:93.5:0.4) to afford 0.38 g of the titled corn pound.

TLC Rf=0.47(dichloromethane:methanol=5:1).

ESI/MS: m/z 846[M+H]$^+$.

General Preparation Process (b)

Preparation of (2R,3S,4R,5S,8R,10R,11R,12S,13S,14R)-13-[(2,6-dideoxy-3-C-methyl-3-O-methyl-4-C-[(n-butylamino)-methyl]-α-L- ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one.

Compound 10 (0.5 g, 0.6698 mmol) prepared according to example 83, tetrabutylammonium iodide (0.74, 2.0 mmoL) and n-butylamine (0.395 mL, 0.2938, 4 mmoL) were dissolved under vibration in 5 ml methanol at 50° C., and the resulting mixture was stirred at the same temperature. Reaction progress was monitored by TLC. After the reaction was completed, the resulting reaction mixture was concentrated, and the residue was dissolved in water (20 ml) and ethyl acetate (20 ml). After stratification, the water layer was washed with ethyl acetate (3×20 ml). The organic extractants were combined and washed with 40 ml of brine, dried over anhydrous sodium sulfate, and filtered. The filtrate was concentrated under vacuum, thereby obtaining a crude product. The crude product was purified by silica gel chromatography (gradient of eluents of methanol:dichloromethane: ammonia water being in a range from 4:95.6:0.4 to 6:93.5:0.4) to afford 0.0888 g of the titled compound.

TLC Rf=0.47(dichloromethane:methanol=5:1).

ESI/MS: m/z 862 [M+H]$^+$.

General Preparation Process c)

Preparation of (2R,3S,4R,5S,8R,10R,11R,12S,13S,14R)-13-[(2,6-dideoxy-3-C-methyl-3-O-methyl-4-C-[(n-propylamino)-methyl]-α-L- ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosy]oxy]-1-oxa-7-azacyclopentadecan-15-one.

Compound 10 (0.5 g, 0.6694 mmol) prepared according to example 83 and n-propylamine (0.5 g, 25 nlmmol) were dissolved under vibration in isopropanol (10 ml) at 50° C., and the resulting mixture was stirred at the same temperature for 72 h. Reaction progress was monitored by TLC. After the reaction was completed, the resulting reaction mixture was concentrated, and the residue was added into saturated sodium bicarbonate solution (50 ml) and dichloromethane (80 ml). The mixture was vibrated uniformly, and stood to be stratified. The organic phase dichloromethane was washed with water (3×50 ml). The organic phases were combined, dried over MgSO$_4$, and concentrated under vacuum to dryness. The resulting substance was dissolved in dichloromethane, and applied on GF254 silica gel. Thin layer chromatography separation was performed with an eluent of 4/1 cyclohexane/diethylamine or 4/1/0.01 dichloromethane/methanol/ammonia water. The chromatographic band corresponding to the desired product was scraped off and further purified by silica gel chromatography eluted with a mixture of dichloromethane/methanol/ammonia in a ratio of 4/1/0.01. The mobile phase was concentrated at 50° C. under vacuum and dried, thereby obtaining 0.16 g of the titled compound as a pure amine.

TLC Rf=0.47(dichloromethane:methanol=5:1).

ESI/MS: m/z 848[M+H]$^+$.

Compounds of examples 85-187 each have a structure shown by the following general formula 1, in which substituent group R is as shown by Table 2. Compounds of examples 85-187 are prepared according to the general preparation process (a), general preparation process (b) and general preparation process (c) of the above example 84. Specific reaction time for preparation of each of compounds of examples 85 to 187 is shown in Table 2. In Table 2, structures, yields and mass spec are data of the final compounds.

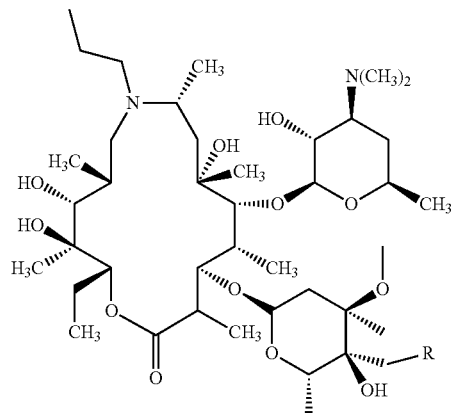

General formula 1

In examples 84 to 187, R is a group shown by Table 2, and nitrogen or sulfur in R is directly attached to methylene of R₃. R' in each of examples 84 to 187 is n-propyl.

TABLE 2

| Examples | Compound No. | R | Preparation process | Reaction time, h | Yield % | Mass spec M + H |
|---|---|---|---|---|---|---|
| 84 (general preparation process (a)) | syzx-217 | cyclopropylamino | general preparation process (a) | 72 | 76 | 846 |
| 84 (general preparation process (b)) | syzx-102 | n-butylamino | general preparation process (b) | 72 | 20 | 862 |
| 84 (general preparation process (c)) | syzx-101 | n-propylamino | general preparation process (c) | 72 | 32 | 848 |
| 85 | syzx-103 | diethylamino | general preparation process (a) | 72 | 60 | 862 |
| 86 | syzx-104 | phenylamino | general preparation process (a) | 72 | 58 | 882 |
| 87 | syzx-105 | morpholinyl | general preparation process (a) | 72 | 42 | 876 |
| 88 | syzx-106 | (5-amino-1,3,3-trimethyl-cyclohexylmethyl)-amino | general preparation process (a) | 72 | 59 | 959 |
| 89 | syzx-107 | piperonylamino | general preparation process (a) | 72 | 58 | 926 |
| 90 | syzx-108 | 4-fluorobenzylamino | general preparation process (c) | 72 | 32 | 914 |
| 91 | syzx-109 | 1,2,3-triazolyl | general preparation process (a) | 72 | 40 | 858 |
| 92 | syzx-110 | ethylamino | general preparation process (a) | 72 | 33 | 834 |
| 93 | syzx-111 | isopropylamino | general preparation process (a) | 72 | 35 | 848 |
| 94 | syzx-112 | isobutylamino | general preparation process (a) | 72 | 56 | 862 |
| 95 | syzx-113 | 3-chlorophenylamino | general preparation process a | 72 | 51 | 914 |
| 96 | syzx-114 | tert-butylamino | general preparation process (a) | 72 | 55 | 862 |
| 97 | syzx-115 | n-hexylamino | general preparation process (a) | 72 | 60 | 890 |
| 98 | syzx-116 | 4-trifluoromethylbenzylamino | general preparation process (a) | 72 | 70 | 964 |
| 99 | syzx-117 | cyclopropyl-methylamino | general preparation process (c) | 72 | 55 | 860 |
| 100 | syzx-118 | 4-methoxy-benzylamino | general preparation process (a) | 72 | 51 | 926 |
| 101 | syzx-119 | 4-nitro-benzyl-amino | general preparation process (a) | 72 | 52 | 941 |
| 102 | syzx-120 | 4-chloro-benzyl-amino | general preparation process (a) | 72 | 60 | 930 |
| 103 | syzx-121 | 3-pyridinylmethylamino | general preparation process (a) | 72 | 33 | 897 |
| 104 | syzx-122 | 3-ethoxyl-propyl-amino | general preparation process (c) | 72 | 36 | 892 |

TABLE 2-continued

| Examples | Compound No. | R | Preparation process | Reaction time, h | Yield % | Mass spec M + H |
|---|---|---|---|---|---|---|
| 105 | syzx-125 | 2-methoxyethyl-amino | general preparation process (c) | 72 | 45 | 864 |
| 106 | syzx-126 | (N-methyl-2-hydroxy-ethyl)-amino | general preparation process (a) | 72 | 50 | 864 |
| 107 | syzx-127 | 3-methoxy-benzyl-amino | general preparation process (c) | 72 | 24 | 926 |
| 108 | syzx-130 | cyclopentyl-amino | general preparation process (a) | 72 | 36 | 874 |
| 109 | syzx-131 | 2,4-difluorobenzyl-amino | general preparation process(c) | 72 | 44 | 932 |
| 110 | syzx-132 | 6-chloro-pyridazin-3-yl-amino | general preparation process (a) | 72 | 58 | 918 |
| 111 | syzx-133 | 4-hydroxy-butylamino | general preparation process (c) | 72 | 23 | 878 |
| 112 | syzx-134 | 1-methyl-3-phenyl-propylamino | general preparation process (c) | 72 | 26 | 938 |
| 113 | syzx-135 | 3-methoxy-benzylamino | general preparation process (c) | 72 | 55 | 926 |
| 114 | syzx-136 | piperazinyl | general preparation process (c) | 72 | 56 | 875 |
| 115 | syzx-137 | trifluoroacetylamino | general preparation process (a) | 72 | 20 | 902 |
| 116 | syzx-138 | 2-chloro-pyridin-4-yl-amino | general preparation process (a) | 72 | 23 | 917 |
| 117 | syzx-139 | 4-formylbenzylamino | general preparation process (a) | 72 | 45 | 940 |
| 118 | syzx-140 | propargyl-amino | general preparation process(a) | 72 | 56 | 844 |
| 119 | syzx-141 | 1-butyrate 2-amino | general preparation process (a) | 72 | 60 | 892 |
| 120 | syzx-142 | 1-butyrate 4-amino | general preparation process (a) | 72 | 50 | 892 |
| 121 | syzx-143 | diglycol-amino | general preparation process (a) | 72 | 45 | 894 |
| 122 | syzx-145 | 2-hydroxy-1-hydroxyethyl-ethylamino | general preparation process (a) | 72 | 56 | 880 |
| 123 | syzx-146 | 3-hydroxy-propylamino | general preparation process (a) | 72 | 57 | 864 |
| 124 | syzx-147 | n-pentyl-amino | general preparation process (c) | 72 | 23 | 876 |
| 125 | syzx-148 | morpholin-4-yl-amino | general preparation process (a) | 72 | 60 | 891 |
| 126 | syzx-150 | 3-amino-butyrate | general preparation process (a) | 72 | 66 | 892 |
| 127 | syzx-151 | 1-hydroxymethyl-propylamino | general preparation process (a) | 72 | 77 | 878 |
| 128 | syzx-153 | ethyl sulfate-amino | general preparation process 1 | 72 | 25 | 930 |
| 129 | syzx-154 | 3,4-difluorophenylmethylamino | general preparation process (a) | 72 | 28 | 932 |

TABLE 2-continued

| Examples | Compound No. | R | Preparation process | Reaction time, h | Yield % | Mass spec M + H |
|---|---|---|---|---|---|---|
| 130 | syzx-155 | 3,5-difluorophenylmethylamino | general preparation process (a) | 72 | 50 | 932 |
| 131 | syzx-158 | 2-methoxyethylamino | general preparation process a | 72 | 36 | 864 |
| 132 | syzx-159 | 1-methyl-4-diethylaminobutylamino | general preparation process (a) | 72 | 37 | 947 |
| 133 | Syzx-161 | 4-sulphonylamino-phenylethylamino | general preparation process (a) | 72 | 5 | 989 |
| 134 | syzx-162 | 1-methyl-but-1-ene-3-yne-amino | general preparation process (b) | 72 | 25 | 870 |
| 135 | syzx-163 | 1-methyl-butyl-amino | general preparation process (a) | 72 | 27 | 876 |
| 136 | syzx-164 | (2-pyridin-4-yl-ethylamino | general preparation process (a) | 72 | 28 | 911 |
| 137 | syzx-165 | (5-methyl-pyrazin-2-yl-methyl)-amino | general preparation process (a) | 72 | 29 | 912 |
| 138 | syzx-167 | cyclohexyl-methyl-amino | general preparation process (a) | 72 | 33 | 902 |
| 139 | syzx-168 | 2-fluoro-phenyl-amino | general preparation process (a) | 72 | 63 | 900 |
| 140 | syzx-169 | 3-morpholinyl-propyl-amino | general preparation process (b) | 72 | 55 | 933 |
| 141 | syzx-170 | 2-chloro-phenylmethyl-amino | general preparation process (b) | 72 | 38 | 947 |
| 142 | syzx-171 | 2-furyl-methyl-amino | general preparation process (a) | 72 | 39 | 902 |
| 143 | syzx-172 | 3-aminobenzyl-amino | general preparation process (a) | 72 | 50 | 930 |
| 144 | syzx-173 | phenylhydrazono | general preparation process (b) | 72 | 23 | 897 |
| 145 | syzx-174 | 2-(1H-indol-3-yl)-ethylamino | general preparation process (a) | 72 | 46 | 949 |
| 146 | syzx-175 | 3-chloro-propyl-amino | general preparation process (c) | 72 | 44 | 882 |
| 147 | syzx-176 | 3,5-dimethoxyphenyl-amino | general preparation process (a) | 72 | 43 | 942 |
| 148 | syzx-178 | 5-methyl-furan-2-yl-amino | general preparation process (a) | 72 | 50 | 886 |
| 149 | syzx-181 | 4-fluoro-phenylhydrazono | general preparation process (b) | 72 | 30 | 915 |
| 150 | syzx-182 | benzyloxy-amino | general preparation process (a) | 72 | 21 | 912 |
| 151 | syzx-183 | p-methoxyphenyl-amino | general preparation process (a) | 72 | 25 | 912 |
| 152 | syzx-184 | 3,4-dimethylphenyl-amino | general preparation process (a) | 72 | 20 | 910 |
| 153 | syzx-187 | diethyl-methyl-amino | general preparation process (a) | 72 | 28 | 876 |
| 154 | syzx-188 | 3-morpholinyl-propyl-amino | general preparation process (a) | 72 | 29 | 933 |

TABLE 2-continued

| Examples | Compound No. | R | Preparation process | Reaction time, h | Yield % | Mass spec M + H |
|---|---|---|---|---|---|---|
| 155 | syzx-190 | 2-pyrrolyl-ethyl-amino | general preparation process (b) | 72 | 32 | 903 |
| 156 | syzx-191 | 2-pyridin-4-yl-ethylamino | general preparation process (a) | 72 | 33 | 911 |
| 157 | syzx-192 | 2-fluorobenzyl-amino | general preparation process (a) | 72 | 36 | 914 |
| 158 | syzx-193 | 2-piperidin-4-yl-methyl-amino | general preparation process (a) | 72 | 11 | 903 |
| 159 | syzx-197 | 2-methyl-4-chloro-phenyl-amino | general preparation process (a) | 72 | 23 | 930 |
| 160 | syzx-198 | N-methyl-butyl-amino | general preparation process (a) | 72 | 12 | 876 |
| 161 | Syzx-202 | 4,6-dichloro-pyrimidin-2-yl-amino | general preparation process (a) | 72 | 42 | 952 |
| 162 | Syzx-203 | cycloheptylamino | general preparation process (a) | 72 | 59 | 902 |
| 163 | Syzx-204 | morpholinyl | general preparation process (a) | 72 | 58 | 876 |
| 164 | Syzx-205 | 4,4-dimethoxy-butylamino | general preparation process (a) | 72 | 32 | 922 |
| 165 | Syzx-206 | piperidinyl-1-amino | general preparation process (a) | 72 | 40 | 889 |
| 166 | Syzx-208 | 6-chloro-pyridin-3-yl-amino | general preparation process (a) | 72 | 35 | 917 |
| 167 | Syzx-209 | tetrahydropyrrolyl | general preparation process (a) | 72 | 56 | 860 |
| 168 | Syzx-210 | 5-hydrosulphonyl-1H-[1,2,4]triazol-3-yl-amino | general preparation process (a) | 72 | 51 | 905 |
| 169 | Syzx-211 | 5-chloropyridinyl-2-amino | general preparation process (a) | 72 | 55 | 917 |
| 170 | Syzx-213 | N-ethylmethylamino | general preparation process (a) | 72 | 70 | 848 |
| 171 | Syzx-214 | diallylamino | general preparation process (a) | 72 | 55 | 886 |
| 172 | Syzx-215 | 2,2,2-trifluoroacetamido | general preparation process (a) | 72 | 51 | 902 |
| 173 | Syzx-218 | 2-chloropyridinyl-3-amino | general preparation process (a) | 72 | 33 | 917 |
| 174 | Syzx-219 | benzamido | general preparation process (a) | 72 | 36 | 910 |
| 175 | Syzx-222 | 4,6-dimethoxypyrimidinyl-2-amino | general preparation process (a) | 72 | 45 | 944 |
| 176 | Syzx-223 | 3-bromophenylamino | general preparation process (a) | 72 | 50 | 960 |
| 177 | Syzx-226 | 5-fluoro-2-nitrophenylamino | general preparation process (a) | 72 | 12 | 945 |

TABLE 2-continued

| Examples | Compound No. | R | Preparation process | Reaction time, h | Yield % | Mass spec M + H |
|---|---|---|---|---|---|---|
| 178 | Syzx-227 | p-iodophenylamino | general preparation process (a) | 72 | 9 | 1008 |
| 179 | Syzx-228 | 2,4-dinitrophenylamino | general preparation process (a) | 72 | 5 | 972 |
| 180 | Syzx-229 | 2,4-dimethylphenylamino | general preparation process (a) | 72 | 6 | 910 |
| 181 | Syzx-230 | 3,5-di(trifluromethyl) phenylamino | general preparation process (a) | 72 | 8 | 1018 |
| 182 | Syzx-231 | 2,4-dichlorophenylamino | general preparation process (a) | 72 | 10 | 950 |
| 183 | Syzx-234 | 5-chloro o-methylphenylamino | general preparation process (a) | 72 | 6 | 930 |
| 184 | Syzx-235 | allopurinol | general preparation process (a) | 72 | 5 | 925 |
| 185 | Syzx-237 | 2,6-dichloropyrimidinyl-4-amino | general preparation process (a) | 72 | 10 | 953 |
| 186 | Syzx-238 | 2-methylimidazolyl | general preparation process (a) | 72 | 11 | 871 |
| 187 | Syzx-239 | N-methyl-2-hydroxyethylamino | general preparation process (c) | 72 | 26 | 864 |

Although the present disclosure is described based on specific examples, certain changes and equivalents are obviously understandable for a person skilled in the art, which fall within the scope of the present disclosure.

Table 3 shows structural formulas of some compounds in Table 1 and Table 2.

TABLE 3

| Example | Compound No. | Name of amine | Structural formula of the compound |
|---|---|---|---|
| 5 (general preparation process 3) | syzx-1 | n-propylamine | 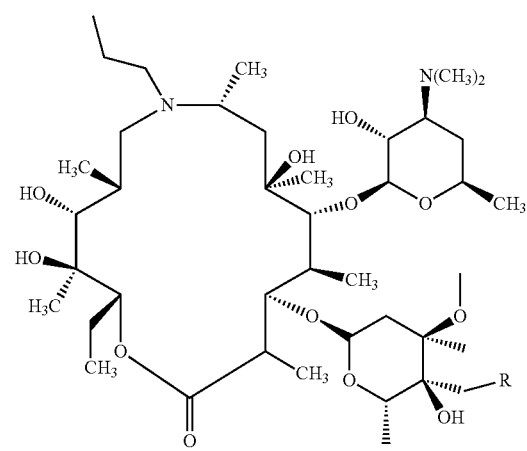 通式 1 |

TABLE 3-continued
| Example | Compound No. | Name of amine | Structural formula of the compound |
|---|---|---|---|
| 5 (general preparation process 2) | syzx-2 | n-butylamine | 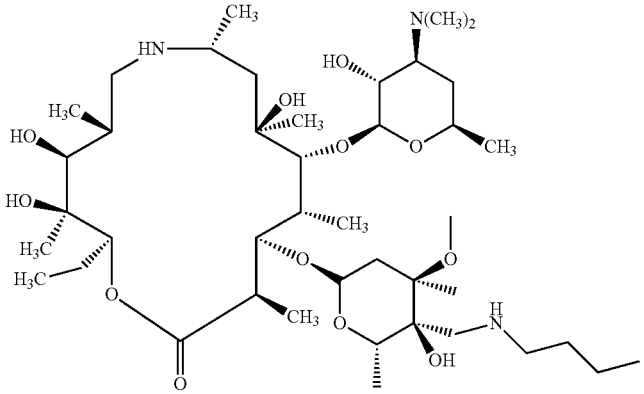 |
| 6 | syzx-3 | diethylamine | 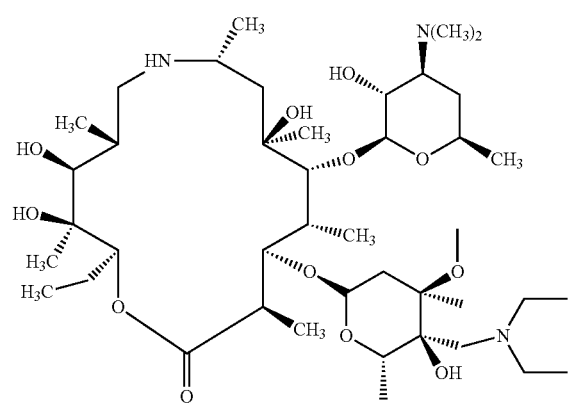 |
| 8 | syzx-5 | morpholine | 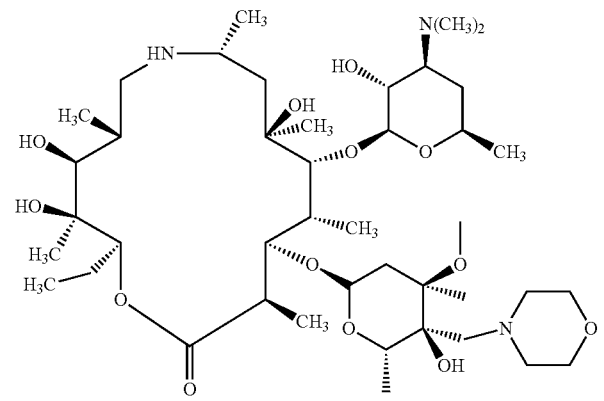 |
| 5 (general preparation process 1) | syzx-6 | cyclopropylamine | 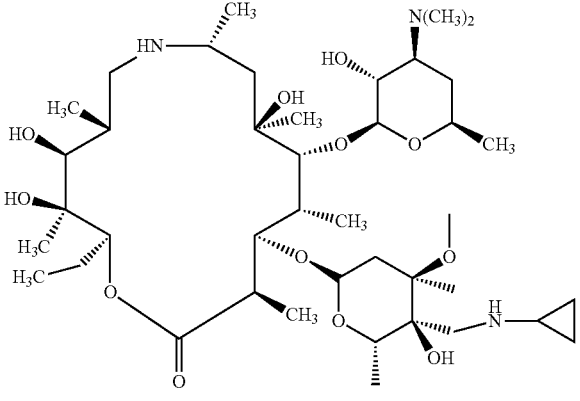 |

TABLE 3-continued
| Example | Compound No. | Name of amine | Structural formula of the compound |
|---|---|---|---|
| 12 | syzx-10 | ethylamine | 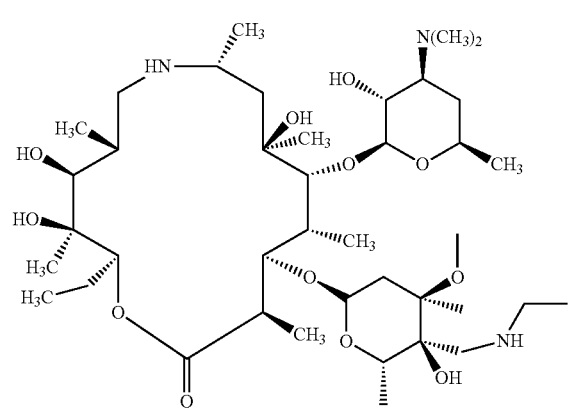 |
| 13 | syzx-11 | isopropylamine | 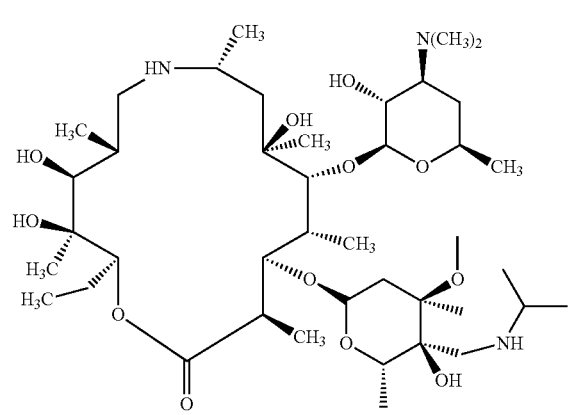 |
| 14 | syzx-12 | isobutylamine | 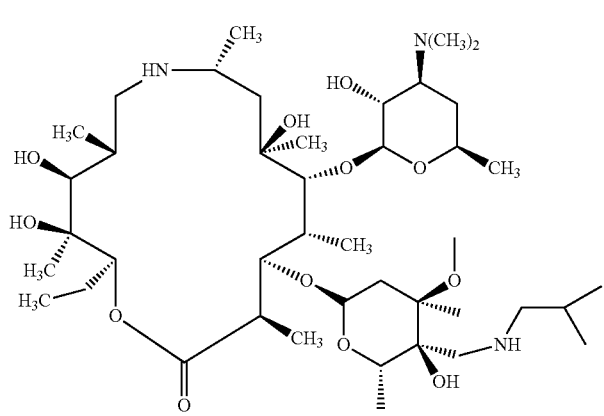 |

TABLE 3-continued

| Example | Compound No. | Name of amine | Structural formula of the compound |
|---|---|---|---|
| 15 | syzx-14 | tert-butylamine | |
| 16 | syzx-15 | piperidine | |
| 17 | syzx-17 | cyclopropylmethylamine | |
| 23 | SYZX-25 | 2-methoxyethylamine | |

TABLE 3-continued

| Example | Compound No. | Name of amine | Structural formula of the compound |
|---|---|---|---|
| 26 | SYZX-30 | cyclopentylamine | |
| 30 | SYZX-35 | 3-methoxybenzylamine | |
| 38 | syzx-47 | n-pentylamine | |

TABLE 3-continued

| Example | Compound No. | Name of amine | Structural formula of the compound |
|---|---|---|---|
| 45 | syzx-58 | 2-methoxyethylamine | |
| 52 | syzx-65 | 2-aminomethyl-5-methylpyrazine | |
| 53 | syzx-66 | 3-methoxypropylamie | |
| 54 | syzx-67 | cyclohexylmethylamine | |

TABLE 3-continued

| Example | Compound No. | Name of amine | Structural formula of the compound |
|---------|--------------|---------------|------------------------------------|
| 170 | Syzx-213 | N-ethylmethylamine | |

Example 188 in vitro tests of susceptibility of the compounds according to the present disclosure against bacterial strains commonly used in laboratories.

In accordance with the Performance Standards for Antimicrobial Disk Susceptibility Tests: Approved Standard published by the US National Committee for Clinical Laboratory Standards, the antibacterial activities of compounds prepared according to examples 5 to 187 were tested. The MICs (minimum inhibitory concentration) of the medicaments prepared according to the examples on the following bacterial strains were measured through mini broth dilution technique.

1. Bacterial Strains

*Staphylococcus aureus* CVCC26003, *Streptococcus equines* CVCC556. *Actinobacillus pleuropneumoniae* CVCC262, *Haemophilus parasuis*, and *Pasteurella multocida* CVCC399, which were purchased from the Control Institute of Veterinary Bioproducts and Pharmaceuticals, China.

2. Test Medicaments (as Controls)

Gamithromycin prepared by a process referring to that described in CN102239174A, the content thereof being 95.2%; and Tulathromycin prepared by a process referring to that described in CN1530370A, the content thereof being 96.4%.

3. Test Apparatus

An SW-CJ-2FD model clean bench manufactured by Suzhou Anti Airtech Co., Ltd, a DNP-9272BS-III model electro-thermal incubator manufactured by Shanghai Xinmiao Medical Instruments Manufacturing Co., Ltd, a 6132 model nucleic acid analyser manufactured by Eppendorf Germany, ABC-265 model double-range electronic scales manufactured by METTLER TOLEDO, MBA of batch No. 20120921 manufactured by Qingdao Hope Bio-Technology Co., Ltd, MHB of batch No. 20120229 manufactured by Qingdao Hope Bio-Technology Co., Ltd, new-born calf serum of batch No. 20120824 manufactured by Weikesheng Biotech Co., Ltd, plastic culture dishes manufactured by Yangzou Guanghua Medical Instrument Factory, a 96-channel pipetting workstation manufactured by METTLER TOLEDO, and a single-channel pipettor and a multi-channel pipettor manufactured by Eppendorf Germany.

4. Test Process 4.1 Preparation of Culture Medium 4.1.1 Culture Medium for *Staphylococcus aureus* CVCC26003

Liquid culture medium: CAMHB. To MHB (prepared according to the specification of the final product) were added $CaCl_2$ and $MgCl_2$, so that a final concentration of $Ca^{2+}$ in the culture medium was 20 mg/L and that of $Mg^{2+}$ therein was 10 mg/L.

Solid culture medium: NINA prepared according to the specification of the final product.

4.1.2 Culture Media for the Rest Four Bacterial Strains.

Liquid culture medium: CAMHB with 10% calf serum and 0.005% NAD+.

Solid culture medium: MHA with 10% calf serum and 0.005% NAD+.

4.2 Strain Revival

The strains were taken out of a refrigerator at −20° C. to be revived, and were spreaded by streaking on the solid culture medium with an inoculating loop. The inoculated culture medium was cultured at 35° C. in a constant temperature incubator for 20 h. Monoclonal antibodies were selected from a well-grown culture plate and streaked on the solid culture medium. The inoculated culture medium was cultured at 35° C. in the constant temperature incubator for 20 h.

4.3 Dilution of the Compounds

The compounds of examples 5 to 80 and the compounds of examples 84 to 187 each were prepared with 100% DMSO into a solution having a concentration of 8.8 mg/mL. A 96-well plate was used, and 100 μl of DMSO was added into each of wells 2 to 11, and 200 μl of ready-prepared medicament solution was added into the $1^{st}$ well, 100 μl of the medicament solution was extracted from the $1^{st}$ well and added into the 2$^{nd}$ well. Double dilution was performed until the 11$^{th}$ well, thereby forming 11 gradients. In this case, compound of parent plate was prepared. 3 μl of double diluted medicament solution was extracted with a 12-channel pipettor and added into wells 1-11 of a new disposable 96-well culture plate. The 12$^{th}$ well thereof is a control well. For each medicament, there are two adjacent rows which are parallel. The transferred compound plate was reserved for later use.

4.4 Preparation of Bacterial Liquid

Representative bacterial colony was selected from the plate prepared in the above section 4.2 and added into normal saline, an OD$_{600}$ value being adjusted to a range of 0.14-0.15. The dilution ratio was recorded, and the bacterial liquid for the tests was diluted according to the recorded dilution ratio. Subsequently, the bacterial suspension and the liquid culture medium were diluted in the proportion of 1:200. The diluted solution was reserved for later use.

4.5 Test Operations

The medicaments and bacterial liquid were added into the compound plates from section 4.3, two rows for each medicament, and one plate for one bacterium. The test results are as shown in Table 5. The MICs of partial compounds failed to be determined in one test, thus further tests were performed under new diluted concentration, so as to further determine the MICs of the compounds.

TABLE 4

Schematic diagram of additives in the 96-well plate

| cmd | 1 | 2 | 3 | 4 | 5 | 6 | 7 | 8 | 9 | 10 | 11 | 12 |
|---|---|---|---|---|---|---|---|---|---|---|---|---|
| A | ○ | ○ | ○ | ○ | ○ | ○ | ○ | ○ | ○ | ○ | ○ | ■ |
| B | ○ | ○ | ○ | ○ | ○ | ○ | ○ | ○ | ○ | ○ | ○ | ■ |
| C | ○ | ○ | ○ | ○ | ○ | ○ | ○ | ○ | ○ | ○ | ○ | ■ |
| D | ○ | ○ | ○ | ○ | ○ | ○ | ○ | ○ | ○ | ○ | ○ | ■ |
| E | ○ | ○ | ○ | ○ | ○ | ○ | ○ | ○ | ○ | ○ | ○ | ▲ |
| F | ○ | ○ | ○ | ○ | ○ | ○ | ○ | ○ | ○ | ○ | ○ | ▲ |
| G | ○ | ○ | ○ | ○ | ○ | ○ | ○ | ○ | ○ | ○ | ○ | ▲ |
| H | ○ | ○ | ○ | ○ | ○ | ○ | ○ | ○ | ○ | ○ | ○ | ▲ |

○ represents 3 μl compound + 100 μl bacterial liquid;
■ represents positive control, the well contains 100 μl bacterial liquid;
▲ represents negative control, the well contains 100 μl culture medium.

TABLE 5

| | | MIC values (ug/ml) of the compounds | | | | |
|---|---|---|---|---|---|---|
| Example | Compound No. | *Actinobacillus pleuropneumoniae* CVCC262 | *Staphylococcus aureus* CVCC26003 | *Pasteurella multocida* CVCC399 | *Streptococcus equines* CVCC556 | *Haemophilus parasuis* |
| Comparison example 1 | Gamithromycin | 0.25 / 0.25 | 0.25 / 0.25 | 0.25 / 0.25 | 0.5 / 0.5 | 0.25 / 0.25 |
| Comparison example 2 | Tulathromycin | 0.25 / 0.25 | 0.25 / 0.25 | 0.25 / 0.25 | 0.25 / 0.25 | 0.25 / 0.25 |
| 5 general preparation process 1 | syzx-6 | 0.125 | 0.125 | 0.125 | 0.125 | 0.125 |
| 5 general preparation process 3 | syzx-1 | 0.125 | 0.125 | 1 | 0.125 | 0.125 |
| 5 general preparation process 2 | syzx-2 | 1 | 4 | 2 | 2 | 2 |
| 6 | syzx-3 | 1 | 0.5 | 0.125 | 0.125 | 0.125 |
| 7 | syzx-4 | 32 | 1 | 1 | ≤0.25 | 0.5 |
| 8 | syzx-5 | 16 | 0.5 | 0.5 | ≤0.25 | 0.5 |
| 9 | syzx-7 | 2 | ≤0.25 | 0.25 | ≤0.25 | ≤0.25 |
| 10 | syzx-8 | 0.5 | ≤0.25 | 0.25 | ≤0.25 | ≤0.25 |
| 11 | syzx-9 | 0.5 | ≤0.25 | ≤0.25 | ≤0.25 | ≤0.25 |
| 12 | syzx-10 | 0.5 | 0.5 | ≤0.25 | 0.5 | 1 |
| 13 | syzx-11 | 0.5 | ≤0.25 | ≤0.25 | ≤0.25 | 0.5 |
| 14 | syzx-12 | ≤0.25 | ≤0.25 | ≤0.25 | ≤0.25 | ≤0.25 |
| 15 | syzx-14 | 0.5 | ≤0.25 | 0.25 | ≤0.25 | ≤0.25 |
| 16 | syzx-15 | 0.5 | ≤0.25 | ≤0.25 | ≤0.25 | ≤0.25 |
| 17 | syzx-17 | 2 | ≤0.25 | 0.25 | ≤0.25 | ≤0.25 |
| 18 | syzx-18 | 16 | 0.5 | 2 | — | 0.5 |
| 19 | syzx-20 | 2 | ≤0.25 | 0.25 | ≤0.25 | ≤0.25 |
| 20 | syzx-21 | 32 | 0.5 | ≤0.25 | ≤0.25 | ≤0.25 |
| 21 | syzx-22 | 8 | 1 | 0.5 | 0.5 | ≤0.25 |
| 22 | syzx-24 | 0.25 | 0.5 | 0.25 | 0.25 | 0.5 |
| 23 | syzx-25 | 16 | ≤0.25 | ≤0.25 | ≤0.25 | ≤0.25 |
| 24 | syzx-27 | 4 | 0.5 | 0.5 | ≤0.25 | ≤0.25 |
| 25 | syzx-29 | 16 | 1 | 2 | 0.5 | 0.5 |
| 26 | syzx-30 | 0.5 | ≤0.25 | ≤0.25 | ≤0.25 | 0.5 |
| 27 | syzx-31 | 1 | ≤0.25 | ≤0.25 | ≤0.25 | ≤0.25 |
| 28 | syzx-32 | 0.5 | 0.5 | 1 | 0.25 | 0.25 |
| 29 | syzx-34 | 8 | 8 | 16 | 0.5 | 4 |
| 30 | syzx-35 | 0.25 | 0.25 | 1 | 0.5 | 0.25 |
| 31 | syzx-37 | 32 | 0.5 | 1 | ≤0.25 | 0.5 |
| 32 | syzx-38 | 32 | 1 | 0.5 | 0.5 | 0.5 |
| 33 | syzx-39 | 0.25 | 0.25 | 0.5 | 0.5 | 0.5 |
| 34 | syzx-40 | 16 | 0.5 | 1 | 0.5 | 0.5 |
| 35 | syzx-41 | 1 | 2 | 4 | 0.5 | 1 |
| 36 | syzx-42 | 1 | 2 | 2 | 1 | 1 |
| 37 | syzx-46 | 32 | 1 | 4 | 2 | ≤0.25 |
| 38 | syzx-47 | 0.5 | 1 | ≤0.25 | ≤0.25 | 0.5 |

TABLE 5-continued

MIC values (ug/ml) of the compounds

| Example | Compound No. | Actinobacillus pleuropneumoniae CVCC262 | Staphylococcus aureus CVCC26003 | Pasteurella multocida CVCC399 | Streptococcus equines CVCC556 | Haemophilus parasuis |
|---|---|---|---|---|---|---|
| 39 | syzx-48 | 16 | 0.5 | 1 | 0.5 | ≤0.25 |
| 40 | syzx-50 | 0.5 | 1 | 1 | 1 | 0.5 |
| 41 | syzx-51 | 1 | 0.5 | 0.5 | 1 | 2 |
| 42 | syzx-52 | 32 | 0.5 | 0.5 | 0.5 | ≤0.25 |
| 43 | syzx-56 | 0.25 | 0.5 | 1 | 0.25 | 0.5 |
| 44 | syzx-57 | ≤0.25 | ≤0.25 | 32 | 4 | ≤0.25 |
| 45 | syzx-58 | 16 | ≤0.25 | ≤0.25 | ≤0.25 | ≤0.25 |
| 46 | syzx-59 | 32 | 1 | 2 | 2 | 0.5 |
| 47 | syzx-60 | 8 | 1 | 2 | 2 | 1 |
| 48 | syzx-61 | 32 | ≤0.25 | 1 | 0.5 | ≤0.25 |
| 49 | syzx-62 | 8 | 0.5 | 0.5 | ≤0.25 | ≤0.25 |
| 50 | syzx-63 | 0.5 | 0.5 | ≤0.25 | ≤0.25 | ≤0.25 |
| 51 | syzx-64 | 0.5 | ≤0.25 | 0.25 | 0.25 | ≤0.25 |
| 52 | syzx-65 | 32 | ≤0.25 | 1 | ≤0.25 | ≤0.25 |
| 53 | syzx-66 | 8 | 1 | ≤0.25 | 0.5 | ≤0.25 |
| 54 | syzx-67 | 0.5 | ≤0.25 | ≤0.25 | ≤0.25 | ≤0.25 |
| 55 | syzx-68 | 8 | ≤0.25 | 8 | ≤0.25 | ≤0.25 |
| 56 | syzx-69 | 1 | 1 | 0.5 | 0.5 | 1 |
| 57 | syzx-71 | 16 | 8 | ≤0.25 | ≤0.25 | 8 |
| 58 | syzx-72 | 16 | 1 | 1 | ≤0.25 | 0.25 |
| 59 | syzx-73 | 1 | 1 | 2 | 0.5 | 1 |
| 60 | syzx-74 | 1 | 1 | 1 | 0.5 | 2 |
| 61 | syzx-75 | 64 | 4 | 8 | 4 | 4 |
| 62 | syzx-76 | 64 | 2 | 4 | 2 | 1 |
| 63 | syzx-77 | 16 | 0.25 | 0.5 | 0.5 | 0.25 |
| 64 | syzx-78 | 2 | 0.25 | 0.5 | 0.25 | 0.25 |
| 65 | syzx-81 | 2 | ≤0.25 | 0.25 | ≤0.25 | ≤0.25 |
| 66 | syzx-82 | 16 | 0.5 | 1 | ≤0.25 | ≤0.25 |
| 67 | syzx-83 | 2 | 0.5 | 0.25 | 0.5 | 0.25 |
| 68 | syzx-84 | 2 | ≤0.25 | 0.25 | ≤0.25 | ≤0.25 |
| 69 | syzx-86 | 2 | ≤0.25 | 0.25 | ≤0.25 | ≤0.25 |
| 70 | syzx-90 | 0.5 | 2 | 2 | 0.5 | 2 |
| 71 | syzx-91 | 2 | 4 | 2 | 1 | 2 |
| 72 | syzx-92 | 0.5 | 1 | 2 | 0.25 | 0.5 |
| 73 | syzx-93 | 16 | 32 | 64 | 1 | 8 |
| 74 | syzx-94 | 0.5 | 1 | 2 | 0.25 | 0.5 |
| 75 | syzx-95 | 2 | 2 | 2 | 0.5 | 2 |
| 76 | syzx-96 | 0.5 | 1 | 2 | 0.25 | 0.5 |
| 77 | syzx-97 | 128 | 1 | 4 | 0.5 | 1 |
| 78 | syzx-98 | 0.5 | 1 | 2 | 0.25 | 0.5 |
| 79 | syzx-99 | 128 | 4 | 8 | 2 | 4 |
| 80 | syzx-100 | 1 | 1 | 0.5 | 2 | 2 |
| 84 general preparation process (a) | syzx-217 | 0.25 | 0.25 | 0.5 | 0.25 | 0.25 |
| 84 general preparation process (b) | syzx-102 | 0.25 | 0.25 | 0.5 | 0.25 | 0.25 |
| 84 general preparation process (c) | syzx-101 | 0.125 | 0.125 | 0.125 | 0.125 | 0.125 |
| 85 | syzx-103 | 0,25 | 0.25 | 1 | 0.25 | 0.25 |
| 86 | syzx-104 | 0.25 | 0.25 | 1 | 0.25 | 0.25 |
| 87 | sync-105 | 1 | 0.25 | 2 | 0.25 | 0.5 |
| 88 | syzx-106 | 0.5 | 2 | 2 | 0.25 | 0.5 |
| 89 | syzx-107 | 0.25 | 0.25 | 1 | 1 | 0.25 |
| 90 | syzx-108 | 0.25 | 0.25 | 1 | 0.25 | 0.25 |
| 91 | syzx-109 | 0.25 | 0.25 | 1 | 0.25 | 0.25 |
| 92 | syzx-110 | 0.25 | 0.25 | 0.5 | 0.25 | 0.25 |
| 93 | syzx-111 | 0.25 | 0.25 | 0.5 | 0.25 | 0.25 |
| 94 | syzx-112 | 0.25 | 0.25 | 0.5 | 0.25 | 0.25 |
| 95 | syzx-113 | 0.25 | 0.25 | 1 | 0.25 | 0.25 |
| 96 | syzx-1 14 | 0.25 | 0.25 | 0.25 | 0.25 | 0.25 |
| 97 | syzx-115 | 0.25 | 0.25 | 0.5 | 0.25 | 0.25 |
| 98 | syzx-116 | 0.25 | 0.25 | 1 | 0.25 | 0.25 |
| 99 | syzx-117 | 0.25 | 0.25 | 0.5 | 0.25 | 0.25 |
| 100 | syzx-118 | 0.25 | 0.25 | 0.25 | 0.25 | 0.25 |
| 101 | syzx-119 | 0.25 | 0.25 | 1 | 0.25 | 0.25 |
| 102 | syzx-120 | 0.25 | 0.25 | 0.5 | 0.25 | 0.25 |
| 103 | syzx-121 | 0.25 | 0.25 | 0.5 | 0.5 | 0.25 |
| 104 | syzx-122 | 1 | 1 | 1 | 0.25 | 0.5 |
| 105 | syzx-125 | 0.5 | 1 | 2 | 0.25 | 0.5 |
| 106 | syzx-126 | 4 | 4 | 2 | 0.5 | 4 |
| 107 | syzx-127 | 1 | 4 | 8 | 0.25 | 1 |

TABLE 5-continued

MIC values (ug/ml) of the compounds

| Example | Compound No. | Actinobacillus pleuropneumoniae CVCC262 | Staphylococcus aureus CVCC26003 | Pasteurella multocida CVCC399 | Streptococcus equines CVCC556 | Haemophilus parasuis |
|---|---|---|---|---|---|---|
| 108 | syzx-130 | 0.5 | 0.25 | 0.5 | 0.25 | 8 |
| 109 | syzx-131 | 0.25 | 0.25 | 0.5 | 0.25 | 0.25 |
| 110 | syzx-132 | 0.5 | 1 | 2 | 0.25 | 0.5 |
| 111 | syzx-133 | 1 | 1 | 2 | 0.5 | 0.5 |
| 112 | syzx-134 | 0.25 | 0.25 | 0.5 | 0.25 | 0.25 |
| 113 | syzx-135 | 1 | 1 | 2 | 0.5 | 0.5 |
| 114 | syzx-136 | 0.5 | 0.25 | 0.5 | 0.25 | 0.25 |
| 115 | syzx-137 | 0.5 | 0.5 | 2 | 1 | 0.5 |
| 116 | syzx-138 | 2 | 2 | 8 | 0.5 | 2 |
| 117 | syzx-139 | 0.25 | 0.25 | 0.5 | 0.25 | 0.25 |
| 118 | syzx-140 | 0.25 | 0.25 | 1 | 0.25 | 0.25 |
| 119 | syzx-141 | 0.25 | 0.25 | 1 | 0.25 | 0.25 |
| 120 | syzx-142 | 0.25 | 0.25 | 0.5 | 0.5 | 0.25 |
| 121 | syzx-143 | 0.25 | 0.25 | 1 | 0.25 | 0.25 |
| 122 | syzx-145 | 64 | 1 | 2 | 0.5 | 0.5 |
| 123 | syzx-146 | 0.25 | 0.25 | 0.5 | 0.25 | 0.25 |
| 124 | syzx-147 | 0.25 | 0.25 | 0.5 | 0.25 | 0.25 |
| 125 | syzx-148 | 0.5 | 0.25 | 1 | 0.25 | 0.5 |
| 126 | syzx-150 | 1 | 0.5 | 2 | 0.25 | 0.5 |
| 127 | syzx-151 | 0.25 | 0.25 | 0.5 | 0.25 | 0.25 |
| 128 | syzx-153 | 0.25 | 0.25 | 1 | 0.25 | 0.25 |
| 129 | syzx-154 | 0.25 | 0.25 | 0.5 | 0.5 | 0.25 |
| 130 | syzx-155 | 0.25 | 0.25 | 0.5 | 0.25 | 0.25 |
| 131 | syzx-158 | 4 | 2 | 2 | 0.25 | 4 |
| 132 | syzx-159 | 0.25 | 0.5 | 0.5 | 0.25 | 0.25 |
| 133 | syzx-161 | 0.25 | 0.25 | 0.5 | 0.25 | 0.25 |
| 134 | syzx-162 | 0.25 | 0.25 | 1 | 0.25 | 0.25 |
| 135 | syzx-163 | 0.25 | 0.25 | 1 | 0.25 | 0.25 |
| 136 | syzx-164 | 0.25 | 0.25 | 2 | 0.5 | 0.25 |
| 137 | syzx-165 | 0.25 | 0.25 | 1 | 0.25 | 0.25 |
| 138 | syzx-167 | 2 | 2 | 4 | 0.25 | 2 |
| 139 | syzx-168 | 0.25 | 0.25 | 1 | 0.25 | 0.25 |
| 140 | syzx-169 | 0.25 | 0.25 | 0.5 | 0.25 | 0.25 |
| 141 | syzx-170 | 0.25 | 0.25 | 0.5 | 0.25 | 0.25 |
| 142 | syzx-171 | 0.25 | 0.25 | 0.5 | 0.25 | 0.25 |
| 143 | syzx-172 | 0.25 | 0.25 | 0.25 | 0.25 | 0.25 |
| 144 | syzx-173 | 1 | 2 | 4 | 0.25 | 1 |
| 145 | syzx-174 | 4 | 4 | 8 | 0.25 | 2 |
| 146 | syzx-175 | 0.25 | 0.5 | 0.5 | 0.5 | 0.25 |
| 147 | syzx-176 | 0.25 | 0.5 | 2 | 0.25 | 0.5 |
| 148 | syzx-178 | 2 | 4 | 4 | 0.5 | 4 |
| 149 | syzx-181 | 0.5 | 0.25 | 1 | 0.25 | 0.25 |
| 150 | syzx-182 | 0.5 | 1 | 4 | 0.5 | 0.5 |
| 151 | syzx-183 | 0.5 | 0.25 | 2 | 0.25 | 0.25 |
| 152 | syzx-184 | 2 | 2 | 4 | 0.5 | 2 |
| 153 | syzx-187 | 0.5 | 1 | 2 | 0.25 | 0.25 |
| 154 | syzx-188 | 0.5 | 0.5 | 1 | 0.25 | 0.5 |
| 155 | syzx-190 | 0.5 | 0.25 | 1 | 0.25 | 0.25 |
| 156 | syzx-191 | 0.5 | 1 | 4 | 0.5 | 0.5 |
| 157 | syzx-192 | 4 | 4 | 4 | 0.5 | 4 |
| 158 | syzx-193 | 4 | 4 | 2 | 0.25 | 2 |
| 159 | syzx-197 | 0.5 | 0.25 | 1 | 0.25 | 0.25 |
| 160 | syzx-198 | 0.5 | 1 | 4 | 0.5 | 0.5 |
| 161 | syzx-202 | 2 | 2 | 2 | 0.25 | 4 |
| 162 | syzx-203 | 1 | 1 | 0.25 | 1 | 0.5 |
| 163 | syzx-204 | 4 | 4 | 4 | 0.5 | 4 |
| 164 | syzx-205 | 4 | 4 | 4 | 0.5 | 4 |
| 165 | syzx-206 | 0.25 | 0.5 | 0.5 | 0.25 | 0.25 |
| 166 | syzx-208 | 4 | 4 | 4 | 0.5 | 4 |
| 167 | syzx-209 | 0.25 | 0.25 | 0.25 | 0.25 | 0.25 |
| 168 | syzx-210 | 0.5 | 2 | 4 | 0.25 | 0.5 |
| 169 | syzx-211 | 4 | 2 | 8 | 0.5 | 4 |
| 170 | syzx-213 | 0.25 | 0.25 | 0.25 | 0.25 | 0.25 |
| 171 | syzx-214 | 2 | 4 | 8 | 0.25 | 2 |
| 172 | syzx-215 | 0.25 | 0.25 | 0.5 | 0.25 | 0.25 |
| 173 | syzx-218 | 4 | 2 | 8 | 0.25 | 4 |
| 174 | syzx-219 | 4 | 2 | 8 | 0.5 | 4 |
| 175 | syzx-222 | 2 | 4 | 8 | 0.25 | 2 |
| 176 | syzx-223 | 0.25 | 0.25 | 0.5 | 0.25 | 0.25 |
| 177 | syzx-226 | 4 | 2 | 8 | 0.25 | 4 |
| 178 | syzx-227 | 4 | 2 | 8 | 0.5 | 4 |
| 179 | syzx-228 | 1 | 2 | 2 | 0.25 | 1 |
| 180 | syzx-229 | 4 | 4 | 16 | 0.25 | 4 |
| 181 | syzx-230 | 2 | 4 | 8 | 0.25 | 2 |

TABLE 5-continued

MIC values (ug/ml) of the compounds

| Example | Compound No. | Actinobacillus pleuropneumoniae CVCC262 | Staphylococcus aureus CVCC26003 | Pasteurella multocida CVCC399 | Streptococcus equines CVCC556 | Haemophilus parasuis |
|---|---|---|---|---|---|---|
| 182 | syzx-231 | 0.25 | 0.25 | 0.5 | 0.25 | 0.25 |
| 183 | syzx-234 | 4 | 2 | 8 | 0.25 | 4 |
| 184 | syzx-235 | 4 | 2 | 8 | 0.5 | 4 |
| 185 | syzx-237 | 4 | 2 | 8 | 0.25 | 4 |
| 186 | syzx-238 | 1 | 1 | 4 | 0.25 | 1 |
| 187 | syzx-239 | 4 | 4 | 8 | 0.25 | 2 |

The in vivo antibacterial activity was measured by conventional animal experiment process well known to the person skilled in the art, and the test animals were BALB/c mice.

Test materials: standard strain of *Streptococcus pneumoniae*, under Accession Number CMCC 31203, purchased from the National Center for Medical Culture Collections; and Tulathromycin prepared by a process referring to that described in CN1530370A.

Test medicaments: compounds (syzx-1, syzx-2, syzx-6) prepared according to the three general preparation processes of example 5, and compounds prepared in example 6 (syzx-3), example 8 (syzx-5), example 12 (syzx-10), example 13 (syzx-11), example 14 (syzx-12), example 15 (syzx-14), example 16 (syzx-15), example 17 (syzx-17), example 18 (syzx-101 prepared according to the general preparation process (c)), example 26 (syzx-30), example 30 (syzx-35), example 38 (syzx-47), example 45 (syzx-58), example 52 (syzx-65), example 53 (syzx-66), example 54 (syzx-67), and example 170 (syzx-213). In the meantime, Tulathromycin was used for comparison. The compounds each were dissolved in absolute ethyl alcohol. The mixture was supplemented until the volume reached a required level, and sufficiently mixed to afford solution with a concentration of 1 mg/mL.

Test Process

Mice each weighed in a range of 18-20 g were selected from 350 mice of 5 to 6 weeks and divided into different cages, with 10 mice in each cage. The mice were breeded for 72 h, and entered into tests if observations turned out normal. Before the tests started, *Streptococcus pneumoniae* was cultured in a blood plate for 24 h, and then added into a sterility broth containing serum for shaking culture (120 r/min) at 37° C., for 20 h, so that an enriched culture can be conducted. Viable count was performed. The bacteria were diluted to $5 \times 10^8$ cfu/mL, with sterilized saline water. The mice each were infected with 0.5 ml of the bacterial liquid by intraperitoneal injection. The day after the infection, compounds prepared according to the above examples and the medicament for comparison were administered to the mice by subcutaneous injection via neck at a dose of 5 mg per kg of body weight for 3 consecutive days. In the meantime, control groups, such as blank control groups and medicament control groups, were arranged. The blank control groups were not administered with any medicament after being infected. The mice in the medicament control groups each were injected with Tulathromycin at a dose of 10 mg per kg of body weight after being infected. After infection and administration, the mice were observed every day, and the death count in each group was recorded until the seventh day, Table 6 shows the influence of the compounds shown in the general formula of the present disclosure on the survival rate of mice infected by *Streptococcus pneumoniae*.

1. Test Results

TABLE 6

Results of in vivo antibacterial tests of certain compounds

| Test medicament | Animal survival rate | Test medicament | Animal survival rate | Test medicament | Animal survival rate |
|---|---|---|---|---|---|
| Blank control group | 100% (10/10) | syzx-5 | 70% (7/10) | syzx-101 | 90% (9/10) |
| Tulathromycin control group | 70% (7/10) | syzx-10 | 90% (9/10) | syzx-30 | 80% (8/10) |
| Negative control group | 30% (3/10) | syzx-11 | 70% (8/10) | syzx-35 | 70% (7/10) |
| syzx-1 | 80% (8/10) | syzx-12 | 70% (8/10) | syzx-47 | 90% (9/10) |
| syzx-2 | 80% (8/10) | syzx-14 | 70% (8/10) | syzx-58 | 80% (8/10) |
| syzx-6 | 80% (8/10) | syzx-15 | 70% (8/10) | syzx-65 | 90% (9/10) |
| syzx-3 | 70% (8/10) | syzx-17 | 70% (8/10) | syzx-66 | 80% (8/10) |
| syzx-67 | 70% (8/10) | syzx-213 | 90% (9/10) | | |

2. Results

As shown in Table 6, administration of the compounds shown by the formula of the present disclosure at a dose of 5 mg per kg of body weight can reduce deaths of the mice due to infection by *Streptococcus pneumoniae*. As compared with the control groups, the compounds of the present disclosure can significantly improve the survival rate of the infected mice, and have manifested evident in vivo antibacterial activity.

Example 189: Acute Toxicity Test of Compound Syzx-24

1. Test Materials 1.1 Test Medicaments

Name of the medicaments: compound No. Syzx-24, and tulathromycin having a content of 96.4% prepared by the process referring to that described in Chinese patent CN1530370A.

1.2 Test Animals

Balb/c mice, each weighed 16.0-19.0 g, were selected. The mice were half male and half female. Before the tests started, the mice were fed in different cages and observed for 3 days. 12 (half male and half female) healthy and brisk mice were selected for tests. The mice were prohibited from feeding, but not water, for 14 h (from 6 pm to 8 am the next morning) before administration.

1.3 Test Articles

A mice gavage device, a 1 ml disposable syringe, a 50 mL beaker and a 100 mL beaker, individual ventilated cages (IVC), ophthalmologic operating scissors, tweezers, a medical tray, 0.5% basic fuchsin dye liquor, medical rubber gloves, an analytical balance, and electronic scales.

2. Test Process 2.1 Test Animals Grouping

Three groups were arranged for the tests, each having four mice (half male and half female). The three groups were respectively tulathromycin group, Syzx-24 group, and solvent control group. The mice were marked with 0.5% basic fuchsin dye liquor. The marked parts of mice in the tulathromycin group were respectively left upper shoulders (female), left ribs (female), right upper shoulders (male) and right ribs (male). The marked parts of mice in the Syzx-24 group were respectively left hinder limbs (female), necks (female), right hinder limbs (male), and necks (male). The mice in the solvent control group were not marked.

Mice in the administered group were administered at a dose of 2000 mg/kg·d-1 (it was reported that the minimum lethal dose of tulathromycin in orally intoxicated mice is higher than 2000 mg/kg·d-1).

2.2 Preparation of Medicament 0.2 g of sodium carboxymethylcellulose was added into 40 ml of purified water and dissolved therein under stirring at 80° C., thereby forming 0.5% sodium carboxymethylcellulose solution as solvent for preparing the medicament. The test medicament was added into the 0.5% sodium carboxymethylcellulose solution according to the dosage of administration, which gave 170 mg/ml suspension. 0.5% sodium carboxymethylcellulose solution of the same volume was added into the suspension and screened through a 100 mesh, whereby a suspension having a concentration of 85 mg/ml was prepared.

2.3 Administration Process

The medicaments were formulated into 85 mg/ml suspensions and administered by gastric perfusion once at a dose of 2000 Ing/kg·d-1. In other words, the medicament was administered to each mouse at a dose of 0.47 ml per 20 g of body weight. Specific grouping and administration are shown in Table 7.

TABLE 7

Grouping of test animals

| Group | Number of animals (n) | Dosage |
| --- | --- | --- |
| Tulathromycin group | 4 | 85 mg/ml tulathromycin suspension, at a dose of 0.47 ml/20 g by gastric perfusion |
| Syzx-24 group | 4 | 85 mg/ml Syzx-24 suspension, at a dose of 0.47 ml/20 g by gastric perfusion |
| Solvent control group | 4 | 0.5% sodium carboxymethylcellulose solution, at a dose of 0.47 ml/20 g by gastric perfusion |

After administration of the medicaments, toxic symptoms and deaths of the animals within 6 h after administration were observed and recorded. The animals were continuously observed for 30 min after administration, and observed once from 1 h to 4 h after administration. Subsequently, the animals were observed once a day until recovery. Toxic symptoms and deaths were recorded, and dead animals were dissected without delay, so that organs, such as heart, liver, spleen, lungs, kidneys, stomach and intestines, can be observed.

3. Test Results and Analysis 3.1 Death rates after 6 h upon infection were compared. Table 8 shows the death status and death rates of the groups.

TABLE 8

Results of deaths of animals

| Group | Number of dead animals/total number of animals | Death rate |
| --- | --- | --- |
| Tulathromycin group | 3/4 (2 female and 1 male) | 75% |
| Syzx-24 group | 0/4 | 0% |
| Solvent control group | 0/4 | 0% |

Acute toxicity tests indicate that toxicities of the compounds according to the present disclosure were obviously lower than that of tulathromycin.

Example 190: Acute Toxicity of Orally Administered Compounds of the Present Disclosure 1. Test Materials 1.1 Appliances and Materials 1 ml disposable plastic sterile syringe, small operating scissors, disposable rubber gloves, a WKZ-4 model pulverizer, a mortar, a measuring cylinder, a beaker, TIANYIJA2003 electronic scales, a medical tray, carbazotic acid dye, medical rubber gloves, a mice gavage device (No. 12), sodium carboxymethylcellulose (Tianjin Kemiou Chemical Reagent Co., Ltd), and the like.

1.2 Test Medicaments

Compounds (syzx-, syzx-2, syzx-6) prepared through the three general preparation processes according to example 5, compound of example 6 (syzx-3), compound of example 8 (syzx-5), compound of example 12 (syzx-10), compound of example 13 (syzx-11), compound of example 14 (syzx-12), compound of example 15 (syzx-14), compound of example 16 (syzx-15), compound of example 17 (syzx-17), compound of example 45 (syzx-58), compound (syzx-101) prepared in general preparation process (c) of example 84, and compound of example 170 (syzx-213).

Solvent for the medicaments: 0.2% sodium carboxymethylcellulose solution.

1.3 Test Animals

SPF level Konmin mice purchased from Henan Provicial Laboratory Animal Center, license number being SCXK (豫)2010-0002. The mice comprise half male and half female, each weighed 18-22 g. The female mice and the male mice are separated and fed in individual ventilated cages. Rearing condition of the mice include sterilized complete teed, free choice feeding and drinking, room temperature in a range of 10-24° C., and relative humidity in a range of 40-60%.

2. Test Process 2.1 Preparation of Medicaments 2.1.1 Preparation of a 0.2% Sodium Carboxymethylcellulose Solution 0.2 g of sodium carboxymethylcellulose was dissolved in 100 ml of purified water, placed overnight for swelling, and then stirred uniformly for later use.

2.1.2 The compounds of some examples were powdered using a mortar, and sifted through mesh (100-mesh) for later use.

2.2 Test Process

Trial tests were performed repeatedly, so that an interval range between $LD_0$ and $LD_{100}$ can be determined and divided into groups, thereby grouping and determining the difference between the groups.

In official tests, 60 mice each weighed in a range of 18-22 g were selected for each medicament. Male mice and female mice were separated and respectively weighed. Mice of the same weight range (for example a range of 18.0-18.9 g or a range of 19.0-19.9 g) were marked and fed in the same cage. The male mice and the female mice were respectively divided into 6 groups at random based on weight, so that mice of different gender and different weight can be evenly distributed in each group, and each group included 10 mice, in which half were male and half were female. Before the mice were infected, the medicament was prepared with 0.2% sodium carboxymethylcellulose solution based on a predetermined concentration. The mice each were gavaged once at a dose of 0.2 ml per 10 g of body weight. The mice were prohibited from feeding, but not from water, within 12-16 h before gavaging. The general health conditions, toxic symptoms, and the death process of the mice were minutely observed and recorded right after the gavaging. The dead mice were roughly dissected without delay, and continuously observed for 7 days.

Per os $LD_{50}$ and 95% fiducial limit (FL) were calculated according to improved karber method. The calculation equations are as follows:

$$LD_{50} = lg^{-1}\left[X_m - i\left(\sum p - 0.5\right)\right]$$

$$S_{x50} = i\sqrt{\sum \frac{pq}{n}}$$

The 95% fiducial limit: $FL = lg^{-1}(lgLD_{50} \pm 1.96 \times S_{x50})$

In the above equations, $X_m$—logarithmic value of the maximum dosage,
i—logarithm of ratio between two adjacent dosages,
p—death rate at each dosage (represented by decimals),
q—survival rate at each dosage, q=−p,
Σp—sum of death rates of the groups,
n—number of animals in each group,
$P_m$—maximum death rate,
$P_n$—minimum death rate,
$S_{x50}$—standard error of $lgLD_{50}$.

3. Test Results

According to the $LD_{50}$ dosage grading stardards for acute toxicity of chemicals in the Guidelines for Acute Toxicity of Veterinary Drugs, a drug, the $LD_{50}$, of which is in a range of 501-5000 mg/kg body weight, is assessed as low toxic. Obviously, the compounds prepared according to the present disclosure have lower toxicity. It is known to the person skilled in the art that the higher the value of $LD_{50}$, the lower the toxicity.

The above embodiments are described only for better understanding, rather than restricting, the present disclosure. Various modifications and variants to the present disclosure may be made by anyone skilled in the art, without departing from the scope and spirit of the present disclosure. The scope of the present disclosure should still be subjected to the scope defined in the claims.

The invention claimed is:

1. A macrolide compound having a structural general formula as shown by formula (I),

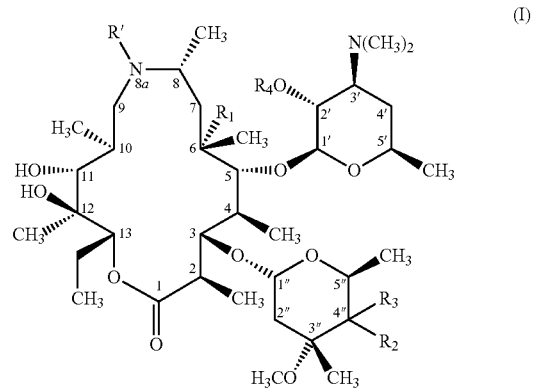

(I)

wherein R' is H or n-propyl,
$R_1$ is selected from a group consisting of H, hydroxyl, methoxyl, propargyl, aryl, and a nitrogen-containing heterocycle,
$R_2$ is hydroxyl,
$R_3$ is —$CH_2R$, wherein R is H or an organic group that contains or does not contain a heteroatom, the heteroatom being selected from a group consisting of O, N, S, and halogen, and
$R_4$ is selected from a group consisting of H, acetyl, and carbobenzoxy.

2. The compound according to claim 1, wherein $R_3$ is —$CH_2NR_{20}R_{30}$ or —$CH_2SR_{40}$, wherein each $R_{20}$, $R_{30}$, and $R_{40}$ is independently H or an organic group that contains or does not contain a heteroatom, the heteroatom being

TABLE 9

Results of acute oral toxicity test on partial compounds of the present disclosure

| Compound | $LD_{50}$ (mg/kg) | 95% fiducial limit (mg/kg) | Compound | $LD_{50}$ (mg/kg) | 95% fiducial limit (mg/kg) |
|---|---|---|---|---|---|
| syzx-1 | 2584.8 | 2156.3-3098.4 | syzx-11 | 4196.0 | 3535.6-4979.8 |
| syzx-2 | 2547.8 | 2231.2-2909.2 | syzx-12 | 4313.5 | 3753.3-4957.4 |
| syzx-6 | 2611.7 | 2229.0-3060.0 | syzx-14 | 2589.5 | 2099.5-3139.8 |
| syzx-3 | 2487.1 | 2162.2-2860.9 | syzx-15 | 2662.0 | 2243.0-3159.3 |
| syzx-5 | 2734.4 | 2219.4-3368.8 | syzx-17 | 2673.5 | 2322.3-3077.7 |
| syzx-10 | 2809.6 | 2291.0-3445.7 | syzx-58 | 3549.4 | 2990.7-4212.4 |
| syzx-213 | 2794.8 | 2375.7-3287.9 | syzx-101 | 3760.6 | 2334.8-3263.9 |
| Tulathromycin | 2379.2 | 1608.1-2818.7 | Gamithromycin | 2165.2 | 1793.8-2613.6 | selected from a group consisting of O, N, S, and halogen, and $R_{20}$ and $R_{30}$ being optionally bonded to each other to form a ring.

3. The compound according to claim 1, wherein $R_3$ is —$CH_2NHR_{50}$, and $R_{50}$ is an organic group that contains or does not contain heteroatom, the heteroatom being selected from a group consisting of O, N, S, and halogen.

4. The compound according to claim 3, wherein $R_{50}$ is selected from a group consisting of n-propyl, n-butyl, cyclopropyl, ethyl, isopropyl, isobutyl, tert-butyl, cyclopropylmethyl, 2-methoxyethyl, cyclopentyl, 2,4-difluorobenzyl, 3-methoxybenzyl, n-pentyl, 2-methyl-pyrazine-5-yl-methyl, 3-methoxypropyl, cyclohexylmethyl, and 4-methoxyphenethyl.

5. The compound according to claim 2, wherein $R_3$ is —$CH_2NR_{20}R_{30}$, and each $R_{20}$ and $R_{30}$ is independently selected from C1-C6 alkyl.

6. The compound according to claim 5, wherein each $R_{20}$ and $R_{30}$ is independently methyl or ethyl.

7. The compound according to claim 1, wherein R in $R_3$ is a nitrogen-containing heterocyclic compound, in which the nitrogen atom is directly attached to the carbon atom of methylene in $R_3$.

8. The compound according to claim 7, wherein R in $R_3$ is morpholinyl, piperidinyl, or piperazinyl.

9. The compound according to claim 2, wherein $R_{20}$ and $R_{30}$ together form a 4 to 10-membered monocyclic ring, or a 5 to 10-membered heteroaryl ring optionally substituted by one or two alkyls.

10. The compound according to claim 2, wherein one of $R_{20}$ and $R_{30}$ is H, and the other thereof is an organic group containing phenyl or benzyl.

11. The compound according to claim 1, wherein the compound is:

1) (2R,3S,4R,5S,8R,10R,11R,12S,13S,14R)-13-[(2,6-dideoxy-3-C-methyl-3-O-methyl-4-C-[(propylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

2) (2R,3S,4R,5S,8R,10R,11R,12S,13S,14R)-13-[(2,6-dideoxy-3-C-methyl-3-O-methyl-4-C-[(butylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

3) (2R,3S,4R,5S,8R,10R,11R,12S,13S,14R)-13-[(2,6-dideoxy-3-C-methyl-3-O-methyl-4-C-[(diethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

4) (2R,3S,4R,5S,8R,10R,11R,12S,13S,14R)-13-[(2,6-dideoxy-3-C-methyl-3-O-methyl-4-C-[(phenylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

5) (2R,3S,4R,5S,8R,10R,11R,12S,13S,14R)-13-[(2,6-dideoxy-3-C-methyl-3-O-methyl-4-C-[(morpholinyl)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

6) (2R,3S,4R,5S,8R,10R,11R,12S,13S,14R)-13-[(2,6-dideoxy-3-C-methyl-3-O-methyl-4-C-[(cyclopropylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

7) (2R,3S,4R,5S,8R,10R,11R,12S,13S,14R)-13-[(2,6-dideoxy-3-C-methyl-3-O-methyl-4-C-[(pyrryl)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

8) (2R,3S,4R,5S,8R,10R,11R,12S,13S,14R)-13-[(2,6-dideoxy-3-C-methyl-3-O-methyl-4-C-[(4-fluorobenzylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

9) (2R,3S,4R,5S,8R,10R,11R,12S,13S,14R)-13-[(2,6-dideoxy-3-C-methyl-3-O-methyl-4-C-[(imidazolyl)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

10) (2R,3S,4R,5S,8R,10R,11R,12S,13S,14R)-13-[(2,6-dideoxy-3-C-methyl-3-O-methyl-4-C-[(ethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

11) (2R,3S,4R,5S,8R,10R,11R,12S,13S,14R)-13-[(2,6-dideoxy-3-C-methyl-3-O-methyl-4-C-[(isopropylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

12) (2R,3S,4R,5S,8R,10R,11R,12S,13S,14R)-13-[(2,6-dideoxy-3-C-methyl-3-O-methyl-4-C-[(isobutylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

13) (2R,3S,4R,5S,8R,10R,11R,12S,13S,14R)-13-[(2,6-dideoxy-3-C-methyl-3-O-methyl-4-C-[tert-butylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

14) (2R,3S,4R,5S,8R,10R,11R,12S,13S,14R)-13-[(2,6-dideoxy-3-C-methyl-3-O-methyl-4-C-[piperidinylmethyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

15) (2R,3S,4R,5S,8R,10R,11R,12S,13S,14R)-13-[(2,6-dide-oxy-3-C-methyl-3-O-methyl-4-C-[(cyclopropylmethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

16) (2R,3S,4R,5S,8R,10R,11R,12S,13S,14R)-13-[(2,6-dide-oxy-3-C-methyl-3-O-methyl-4-C-[(4-methoxybenzylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

17) (2R,3S,4R,5S,8R,10R,11R,12S,13S,14R)-13-[(2,6-dide-oxy-3-C-methyl-3-O-methyl-4-C-[(4-chlorolbenzylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

18) (2R,3S,4R,5S,8R,10R,11R,12S,13S,14R)-13-[(2,6-dide-oxy-3-C-methyl-3-O-methyl-4-C-[(3-pyridinylmethylamino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

19) (2R,3S,4R,5S,8R,10R,11R,12S,13S,14R)-13-[(2,6-dide-oxy-3-C-methyl-3-O-methyl-4-C-[((3-ethoxypropyl)amino)methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

20) (2R,3S,4R,5S,8R,10R,11R,12S,13S,14R)-13-[(2,6-dide-oxy-3-C-methyl-3-O-methyl-4-C-[(2-methoxyethyl)amino-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

21) (2R,3S,4R,5S,8R,10R,11R,12S,13S,14R)-13-[(2,6-dide-oxy-3-C-methyl-3-O-methyl-4-C-[2-methoxybenzylamino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

22) (2R,3S,4R,5S,8R,10R,11R,12S,13S,14R)-13-[(2,6-dide-oxy-3-C-methyl-3-O-methyl-4-C-[[(2-[(N-methyl)amino]-ethyl)amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

23) (2R,3S,4R,5S,8R,10R,11R,12S,13S,14R)-13-[(2,6-dide-oxy-3-C-methyl-3-O-methyl-4-C-[(cyclopentylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

24) (2R,3S,4R,5S,8R,10R,11R,12S,13S,14R)-13-[(2,6-dide-oxy-3-C-methyl-3-O-methyl-4-C-[2,4-difluorobenzylamino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

25) (2R,3S,4R,5S,8R,10R,11R,12S,13S,14R)-13-[(2,6-dide-oxy-3-C-methyl-3-O-methyl-4-C-[(2,6-chloro-pyridazin-3-yl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

26) (2R,3S,4R,5S,8R,10R,11R,12S,13S,14R)-13-[(2,6-dide-oxy-3-C-methyl-3-O-methyl-4-C-[[(1-methyl-3-phenyl)propyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

27) (2R,3S,4R,5S,8R,10R,11R,12S,13S,14R)-13-[(2,6-dide-oxy-3-C-methyl-3-O-methyl-4-C-[[3-methoxybenzylamino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

28) (2R,3S,4R,5S,8R,10R,11R,12S,13S,14R)-13-[(2,6-dide-oxy-3-C-methyl-3-O-methyl-4-C-[[2,2,2-trifluoro-acetyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

29) (2R,3S,4R,5S,8R,10R,11R,12S,13S,14R)-13-[(2,6-dide-oxy-3-C-methyl-3-O-methyl-4-C-[[[(2-chloro-pyridin-4-yl-amino)-methyl]-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

30) (2R,3S,4R,5S,8R,10R,11R,12S,13S,14R)-13-[(2,6-dide-oxy-3-C-methyl-3-O-methyl-4-C-[[[(4-formyl-benzyl-amino)-methyl]-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

31) (2R,3S,4R,5S,8R,10R,11R,12S,13S,14R)-13-[(2,6-dide-oxy-3-C-methyl-3-O-methyl-4-C-[[propargyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

32) (2R,3S,4R,5S,8R,10R,11R,12S,13S,14R)-13-[(2,6-dide-oxy-3-C-methyl-3-O-methyl-4-C-[[butyrate-2-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

33)
(2R,3S,4R,5S,8R,10R,11R,12S,13S,14R)-13-[(2,6-dideoxy-3-C-methyl-3-O-methyl-4-C-[[butyrate-4-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosy]oxy]-1-oxa-7-azacyclopentadecan-15-one;

34)
(2R,3S,4R,5S,8R,10R,11R,12S,13S,14R)-13-[(2,6-dideoxy-3-C-methyl-3-O-methyl-4-C-[(3-hydroxy-propylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

35)
(2R,3S,4R,5S,8R,10R,11R,12S,13S,14R)-13-[(2,6-dideoxy-3-C-methyl-3-O-methyl-4-C-[[n-pentyl-amino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

36)
(2R,3S,4R,5S,8R,10R,11R,12S,13S,14R)-13-[(2,6-dideoxy-3-C-methyl-3-O-methyl-4-C-[(morpholin-4-yl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

37)
3-({(2R,3S,4R,5S,8R,10R,11R,12S,13S,14R)-6-[-11-[[3,4,6-trideoxy-3-(dimethylamino)-β-D-xylo-hexopyranosy]oxy]-2-ethyl-3,4,10-trihydroxy-3,5,8,10,12,14-hexamethyl-1-oxa-7-azacyclopentadecan-15-one-13-yl-oxy]-3-hydroxy-4-methoxy-2,4-dimethyl-tetrahydropyran-3-yl-methyl}-amino)-butyric acid;

38)
(2R,3S,4R,5S,8R,10R,11R,12S,13S,14R)-13-[(2,6-dideoxy-3-C-methyl-3-O-methyl-4-C-[(1-hydroxymethyl-propylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

39)
(2R,3S,4R,5S,8R,10R,11R,12S,13S,14R)-13-[(2,6-dideoxy-3-C-methyl-3-O-methyl-4-C-[(2-hydroxy-2-phenyl-ethylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

40)
(2R,3S,4R,5S,8R,10R,11R,12S,13S,14R)-13-[(2,6-dideoxy-3-C-methyl-3-O-methyl-4-C-[(4-dimethoxy-butylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

41)
(2R,3S,4R,5S,8R,10R,11R,12S,13S,14R)-13-[(2,6-dideoxy-3-C-methyl-3-O-methyl-4-C-[(3,4-dichloro-benzylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

42)
(2R,3S,4R,5S,8R,10R,11R,12S,13S,14R)-13-[(2,6-dideoxy-3-C-methyl-3-O-methyl-4-C-[(1-methyl-4-dimethylaminobutylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

43)
(2R,3S,4R,5S,8R,10R,11R,12S,13S,14R)-13-[(2,6-dideoxy-3-C-methyl-3-O-methyl-4-C-[[(3-cyclohexylamino)propylamino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

44)
(2R,3S,4R,5S,8R,10R,11R,12S,13S,14R)-13-[(2,6-dideoxy-3-C-methyl-3-O-methyl-4-C-[[(4-mesylphenyl-ethylamino)propylamino]-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

45)
(2R,3S,4R,5S,8R,10R,11R,12S,13S,14R)-13-[(2,6-dideoxy-3-C-methyl-3-O-methyl-4-C-[[(1-methyl-but-1-en-3-yne-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

46)
(2R,3S,4R,5S,8R,10R,11R,12S,13S,14R)-13-[(2,6-dideoxy-3-C-methyl-3-O-methyl-4-C-[[(1-methyl-butyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

47)
(2R,3S,4R,5S,8R,10R,11R,12S,13S,14R)-13-[(2,6-dideoxy-3-C-methyl-3-O-methyl-4-C-[[(2-pyridin-4-yl-ethylamine)-methyl]]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

48)
(2R,3S,4R,5S,8R,10R,11R,12S,13S,14R)-13-[(2,6-dideoxy-3-C-methyl-3-O-methyl-4-C-{[(5-methyl-pyrazin-2-yl-methyl)-amino]-methyl}-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

49)
(2R,3S,4R,5S,8R,10R,11R,12S,13S,14R)-13-[(2,6-dideoxy-3-C-methyl-3-O-methyl-4-C-[[(3-methoxy-propyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

50)
(2R,3S,4R,5S,8R,10R,11R,12S,13S,14R)-13-[(2,6-dideoxy-3-C-methyl-3-O-methyl-4-C-[[cyclohexyl-methyl-amino)-methyl]-α-L-ribopyranosyl)oxy]-2-ethyl-3,4,10-trihydroxy-3,5,8,10,12,14-hexamethyl- 11-[[3,4,6-trideoxy-3-(dimethylamino)-β-D-xylo-hexopyranosyl]oxy]-1-oxa-7-azacyclopentadecan-15-one;

51) (2R,3S,4R,5S,8R,10R,11R,12S,13S,14R)-13-[(2,6-dideoxy-3-C-methyl-3-O-methyl-4-C-[(2-fluoro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

52) (2R,3S,4R,5S,8R,10R,11R,12S,13S,14R)-13-[(2,6-dideoxy-3-C-methyl-3-O-methyl-4-C-[(3-morpholinyl-propyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

53) (2R,3S,4R,5S,8R,10R,11R,12S,13S,14R)-13-[(2,6-dideoxy-3-C-methyl-3-O-methyl-4-C-[(2-furfuryl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

54) (2R,3S,4R,5S,8R,10R,11R,12S,13S,14R)-13-[(2,6-dideoxy-3-C-methyl-3-O-methyl-4-C-[(3-aminobenzyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

55) (2R,3S,4R,5S,8R,10R,11R,12S,13S,14R)-13-[(2,6-dideoxy-3-C-methyl-3-O-methyl-4-C-[(phenylhydrazono)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

56) (2R,3S,4R,5S,8R,10R,11R,12S,13S,14R)-13-[(2,6-dideoxy-3-C-methyl-3-O-methyl-4-C-{[2-(1H-indol-3-yl)-ethylamino]-methyl}-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

57) (2R,3S,4R,5S,8R,10R,11R,12S,13S,14R)-13-[(2,6-dideoxy-3-C-methyl-3-O-methyl-4-C-[(3-chloropropyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

58) (2R,3S,4R,5S,8R,10R,11R,12S,13S,14R)-13-[(2,6-dideoxy-3-C-methyl-3-O-methyl-4-C-[(3,5-dimethoxyphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

59) (2R,3S,4R,5S,8R,10R,11R,12S,13S,14R)-13-[(2,6-dideoxy-3-C-methyl-3-O-methyl-4-C-[(thienylformyloxymethyl-2-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

60) (2R,3S,4R,5S,8R,10R,11R,12S,13S,14R)-13-[(2,6-dideoxy-3-C-methyl-3-O-methyl-4-C-[(5-methylfurfuryl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

61) (2R,3S,4R,5S,8R,10R,11R,12S,13S,14R)-13-[(2,6-dideoxy-3-C-methyl-3-O-methyl-4-C-[(4-fluoro-phenylhydrazono)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

62) (2R,3S,4R,5S,8R,10R,11R,12S,13S,14R)-13-[(2,6-dideoxy-3-C-methyl-3-O-methyl-4-C-[(benzyloxy-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

63) (2R,3S,4R,5S,8R,10R,11R,12S,13S,14R)-13-[(2,6-dideoxy-3-C-methyl-3-O-methyl-4-C-[(p-methoxyphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

64) (2R,3S,4R,5S,8R,10R,11R,12S,13S,14R)-13-[(2,6-dideoxy-3-C-methyl-3-O-methyl-4-C-[(3,4-dimethylphenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

65) (2R,3S,4R,5S,8R,10R,11R,12S,13S,14R)-13-[(2,6-dideoxy-3-C-methyl-3-O-methyl-4-C-[(5-fluoropyridin-2-yl-amino)-methyl]-α-L-ribopyranosyl)oxy]-2-ethyl-3,4,10-trihydroxy-3,5,8,10,12,14-hexamethyl-11-[[(3,4,6-trideoxy-3-(dimethylamino)-β-D-xylo-hexopyranosyl]oxy]-1-oxa-7-azacyclopentadecan-15-one;

66) (2R,3S,4R,5S,8R,10R,11R,12S,13S,14R)-13-[(2,6-dideoxy-3-C-methyl-3-O-methyl-4-C-[(2-pyrrolyl-ethyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

67) (2R,3S,4R,5S,8R,10R,11R,12S,13S,14R)-13-[(2,6-dideoxy-3-C-methyl-3-O-methyl-4-C-[(2-pyridin-4-yl-ethylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

68) (2R,3S,4R,5S,8R,10R,11R,12S,13S,14R)-13-[(2,6-dideoxy-3-C-methyl-3-O-methyl-4-C-[(2-fluorobenzyl-amino)-methyl]-α-L-ribopyranosyl)oxy]-2-ethyl-3,4,10-trihydroxy-3,5,8,10,12,14-hexamethyl-11-[[3,4,6-

69) (2R,3S,4R,5S,8R,10R,11R,12S,13S,14R)-13-[(2,6-dideoxy-3-C-methyl-3-O-methyl-4-C-[(2-piperidin-4-yl-methyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

70) (2R,3S,4R,5S,8R,10R,11R,12S,13S,14R)-13-[(2,6-dideoxy-3-C-methyl-3-O-methyl-4-C-[(5-chloro-o-methyl-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

71) (2R,3S,4R,5S,8R,10R,11R,12S,13S,14R)-13-[(2,6-dideoxy-3-C-methyl-3-O-methyl-4-C-[(2-fluoro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(methylamino)-β-D-xylo-hexopyranosyl]oxy]-1-oxa-7-azacyclopentadecan-15-one;

72) (2R,3S,4R,5S,8R,10R,11R,12S,13S,14R)-13-[(2,6-dideoxy-3-C-methyl-3-O-methyl-4-C-[(2-fluoro-5-methyl-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

73) (2R,3S,4R,5S,8R,10R,11R,12S,13S,14R)-13-[(2,6-dideoxy-3-C-methyl-3-O-methyl-4-C-[(2-methyl-4-chloro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

74) (2R,3S,4R,5S,8R,10R,11R,12S,13S,14R)-13-[(2,6-dideoxy-3-C-methyl-3-O-methyl-4-C-[(N-methyl-butyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

75) (2R,3S,4R,5S,8R,10R,11R,12S,13S,14R)-13-[(2,6-dideoxy-3-C-methyl-3-O-methyl-4-C-[(quinolin-6-yl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

76) (2R,3S,4R,5S,8R,10R,11R,12S,13S,14R)-13-[(2,6-dideoxy-3-C-methyl-3-O-methyl-4-C-[(1,2,2-trimethyl-propylamino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

77) (2R,3S,4R,5S,8R,10R,11R,12S,13S,14R)-13-[(2,6-dideoxy-3-C-methyl-3-O-methyl-4-C-[(n-propyl-amino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

78) (2R,3S,4R,5S,8R,10R,11R,12S,13S,14R)-13-[(2,6-dideoxy-3-C-methyl-3-O-methyl-4-C-[(n-butyl-amino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

79) (2R,3S,4R,5S,8R,10R,11R,12S,13S,14R)-13-[2,6-dideoxy-3-C-methyl-3-O-methyl-4-C-[(pentylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

80) (2R,3S,4R,5S,8R,10R,11R,12S,13S,14R)-13-[(2,6-dideoxy-3-C-methyl-3-O-methyl-4-C-[(diethylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

81) (2R,3S,4R,5S,8R,10R,11R,12S,13S,14R)-13-[(2,6-dideoxy-3-C-methyl-3-O-methyl-4-C-[(phenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

82) (2R,3S,4R,5S,8R,10R,11R,12S,13S,14R)-13-[(2,6-dideoxy-3-C-methyl-3-O-methyl-4-C-[(morpholinyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

83) (2R,3S,4R,5S,8R,10R,11R,12S,13S,14R)-13-[(2,6-dideoxy-3-C-methyl-3-O-methyl-4-C-{[(5-amino-1,3,3-trimethyl-cyclohexylmethyl)-amino]-methyl}-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

84) 13-[(2,6-dideoxy-3-C-methyl-3-O-methyl-4-C-[piperonylamino-methyl)]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

85) (2R,3S,4R,5S,8R,10R,11R,12S,13S,14R)-13-[(2,6-dideoxy-3-C-methyl-3-O-methyl-4-C-[(4-fluorobenzylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

86) (2R,3S,4R,5S,8R,10R,11R,12S,13S,14R)-13-[(2,6-dideoxy-3-C-methyl-3-O-methyl-4-C-[(1,2,3-triazolyl)methyl]-α-L-ribopyranosyl)oxy]-2-ethyl-3,4,10-trihydroxy-3,5,8,10,12,14-hexamethyl-7-propyl-11-[[3,4,6- trideoxy-3-(dimethylamino)-β-D-xylo-hexopyranosyl] oxy]-1-oxa-7-azacyclopentadecan-15-one;

87) (2R,3S,4R,5S,8R,10R,11R,12S,13S,14R)-13-[(2,6-dideoxy-3-C-methyl-3-O-methyl-4-C-[(ethylamino) methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl] oxy]-1-oxa-7-azacyclopentadecan-15-one;

88) (2R,3S,4R,5S,8R,10R,11R,12S,13S,14R)-13-[(2,6-dideoxy-3-C-methyl-3-O-methyl-4-C-[(isopropylamino) methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl] oxy]-1-oxa-7-azacyclopentadecan-15-one;

89) (2R,3S,4R,5S,8R,10R,11R,12S,13S,14R)-13-[(2,6-dideoxy-3-C-methyl-3-O-methyl-4-C-[(isobutylamino) methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl] oxy]-1-oxa-7-azacyclopentadecan-15-one;

90) (2R,3S,4R,5S,8R,10R,11R,12S,13S,14R)-13-[(2,6-dideoxy-3-C-methyl-3-O-methyl-4-C-[(3-chlorophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

91) (2R,3S,4R,5S,8R,10R,11R,12S,13S,14R)-13-[(2,6-dideoxy-3-C-methyl-3-O-methyl-4-C-[(tert-butylamino) methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl] oxy]-1-oxa-7-azacyclopentadecan-15-one;

92) (2R,3S,4R,5S,8R,10R,11R,12S,13S,14R)-13-[(2,6-dideoxy-3-C-methyl-3-O-methyl-4-C-[(n-hexylamino) methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl] oxy]-1-oxa-7-azacyclopentadecan-15-one;

93) (2R,3S,4R,5S,8R,10R,11R,12S,13S,14R)-13-[(2,6-dideoxy-3-C-methyl-3-O-methyl-4-C-[(4-trifluoromethyl-benzylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

94) (2R,3S,4R,5S,8R,10R,11R,12S,13S,14R)-13-[(2,6-dideoxy-3-C-methyl-3-O-methyl-4-C-[(cyclopropyl-methylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

95) (2R,3S,4R,5S,8R,10R,11R,12S,13S,14R)-13-[(2,6-dideoxy-3-C-methyl-3-O-methyl-4-C-[(4-methoxy-benzylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

96) (2R,3S,4R,5S,8R,10R,11R,12S,13S,14R)-13-[(2,6-dideoxy-3-C-methyl-3-O-methyl-4-C-[[(4-nitro-benzyl) amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

97) (2R,3S,4R,5S,8R,10R,11R,12S,13S,14R)-13-[(2,6-dideoxy-3-C-methyl-3-O-methyl-4-C-[4-chloro-benzyl-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

98) (2R,3S,4R,5S,8R,10R,11R,12S,13S,14R)-13-[(2,6-dideoxy-3-C-methyl-3-O-methyl-4-C-[(3-pyridinyl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

99) (2R,3S,4R,5S,8R,10R,11R,12S,13S,14R)-13-[(2,6-dideoxy-3-C-methyl-3-O-methyl-4-C-[[(3-ethyoxyl-propyl)-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

100) (2R,3S,4R,5S,8R,10R,11R,12S,13S,14R)-13-[(2,6-dideoxy-3-C-methyl-3-O-methyl-4-C-[(2-methoxyethyl)-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

101) (2R,3S,4R,5S,8R,10R,11R,12S,13S,14R)-13-[(2,6-dideoxy-3-C-methyl-3-O-methyl-4-C-[(3-methyl-2-hydroxy-ethyl)amino-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

102) (2R,3S,4R,5S,8R,10R,11R,12S,13S,14R)-13-[(2,6-dideoxy-3-C-methyl-3-O-methyl-4-C-[(3-methoxy-benzyl)-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

103) (2R,3S,4R,5S,8R,10R,11R,12S,13S,14R)-13-[(2,6-dideoxy-3-C-methyl-3-O-methyl-4-C-[(cyclopentyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

104)
(2R,3S,4R,5S,8R,10R,11R,12S,13S,14R)-13-[(2,6-dideoxy-3-C-methyl-3-O-methyl-4-C-[(2,4-difluorobenzyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

105)
(2R,3S,4R,5S,8R,10R,11R,12S,13S,14R)-13-[(2,6-dideoxy-3-C-methyl-3-O-methyl-4-C-[(2,6-chloro-pyridazin-3-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

106)
(2R,3S,4R,5S,8R,10R,11R,12S,13S,14R)-13-[(2,6-dideoxy-3-C-methyl-3-O-methyl-4-C-[(4-hydroxy-butyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

107)
(2R,3S,4R,5S,8R,10R,11R,12S,13S,14R)-13-[(2,6-dideoxy-3-C-methyl-3-O-methyl-4-C-[(1-methyl-3-phenyl-propylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

108)
(2R,3S,4R,5S,8R,10R,11R,12S,13S,14R)-13-[(2,6-dideoxy-3-C-methyl-3-O-methyl-4-C-[(3-methoxy-benzylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

109)
(2R,3S,4R,5S,8R,10R,11R,12S,13S,14R)-13-[(2,6-dideoxy-3-C-methyl-3-O-methyl-4-C-[piperazinyl-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

110)
(2R,3S,4R,5S,8R,10R,11R,12S,13S,14R)-13-[(2,6-dideoxy-3-C-methyl-3-O-methyl-4-C-[[trifluoroacetylamino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

111)
(2R,3S,4R,5S,8R,10R,11R,12S,13S,14R)-13-[(2,6-dideoxy-3-C-methyl-3-O-methyl-4-C-[[[(2-chloro-pyridin-4-yl-amino)-methyl]-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

112)
(2R,3S,4R,5S,8R,10R,11R,12S,13S,14R)-13-[(2,6-dideoxy-3-C-methyl-3-O-methyl-4-C-[[4-formylbenzylamino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

113)
(2R,3S,4R,5S,8R,10R,11R,12S,13S,14R)-13-[(2,6-dideoxy-3-C-methyl-3-O-methyl-4-C-[[propargyl-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

114)
(2R,3S,4R,5S,8R,10R,11R,12S,13S,14R)-13-[(2,6-dideoxy-3-C-methyl-3-O-methyl-4-C-[[1-butyrate2-amino]-methyl]-α-L-ribopyranosyl)oxy]-2-ethyl-3,4,10-trihydroxy-3,5,8,10,12,14-hexamethyl-7-propyl-1H[3,4,6-trideoxy-3-(dimethylamino)-β-D-xylo-hexopyranosyl]oxy]-1-oxa-7-azacyclopentadecan-15-one;

115)
(2R,3S,4R,5S,8R,10R,11R,12S,13S,14R)-13-[(2,6-dideoxy-3-C-methyl-3-O-methyl-4-C-[[1-butyrate4-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)+D-xylo-hexopyranosyl]oxy]-1-oxa-7-azacyclopentadecan-15-one;

116)
(2R,3S,4R,5S,8R,10R,11R,12S,13S,14R)-13-[(2,6-dideoxy-3-C-methyl-3-O-methyl-4-C-[[diglycol-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

117)
(2R,3S,4R,5S,8R,10R,11R,12S,13S,14R)-13-[(2,6-dideoxy-3-C-methyl-3-O-methyl-4-C-[(2-hydroxy-1-hydroxyethyl-ethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

118)
(2R,3S,4R,5S,8R,10R,11R,12S,13S,14R)-13-[(2,6-dideoxy-3-C-methyl-3-O-methyl-4-C-[(3-hydroxy-propylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

119)
(2R,3S,4R,5S,8R,10R,11R,12S,13S,14R)-13-[(2,6-dideoxy-3-C-methyl-3-O-methyl-4-C-[[n-pentyl-amino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

120)
(2R,3S,4R,5S,8R,10R,11R,12S,13S,14R)-13-[(2,6-dideoxy-3-C-methyl-3-O-methyl-4-C-[(morpholin-4-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

121)
(2R,3S,4R,5S,8R,10R,11R,12S,13S,14R)-13-[(2,6-dideoxy-3-C-methyl-3-O-methyl-4-C-[(3-amino-butyrate)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

122)
(2R,3S,4R,5S,8R,10R,11R,12S,13S,14R)-13-[(2,6-dideoxy-3-C-methyl-3-O-methyl-4-C-[(1-hydroxymethyl-propylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

123)
(2R,3S,4R,5S,8R,10R,11R,12S,13S,14R)-13-[(2,6-dideoxy-3-C-methyl-3-O-methyl-4-C-[(2-hydroxy-2-phenyl-ethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

124)
(2R,3S,4R,5S,8R,10R,11R,12S,13S,14R)-13-[(2,6-dideoxy-3-C-methyl-3-O-methyl-4-C-[(3,4-difluorophenylmethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

125)
(2R,3S,4R,5S,8R,10R,11R,12S,13S,14R)-13-[(2,6-dideoxy-3-C-methyl-3-O-methyl-4-C-[(3,5-difluorophenylmethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

126)
(2R,3S,4R,5S,8R,10R,11R,12S,13S,14R)-13-[(2,6-dideoxy-3-C-methyl-3-O-methyl-4-C-[(2-methoxyethyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

127)
(2R,3S,4R,5S,8R,10R,11R,12S,13S,14R)-13-[(2,6-dideoxy-3-C-methyl-3-O-methyl-4-C-[(1-methyl-4-diethylaminobutylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

128)
(2R,3S,4R,5S,8R,10R,11R,12S,13S,14R)-13-[(2,6-dideoxy-3-C-methyl-3-O-methyl-4-C-[[4-sulphonylamino-phenylethylamino]-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

129)
(2R,3S,4R,5S,8R,10R,11R,12S,13S,14R)-13-[(2,6-dideoxy-3-C-methyl-3-O-methyl-4-C-[[(1-methyl-but-1-ene-3-yne-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

130)
(2R,3S,4R,5S,8R,10R,11R,12S,13S,14R)-13-[(2,6-dideoxy-3-C-methyl-3-O-methyl-4-C-[[(1-methyl-butyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

131)
(2R,3S,4R,5S,8R,10R,11R,12S,13S,14R)-13-[(2,6-dideoxy-3-C-methyl-3-O-methyl-4-C-[[(2-pyridin-4-yl-ethylamino)-methyl]α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

132)
(2R,3S,4R,5S,8R,10R,11R,12S,13S,14R)-13-[(2,6-dideoxy-3-C-methyl-3-O-methyl-4-C-{[(5-methyl-pyrazin-2-yl-methyl)-amino]-methyl}-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

133)
(2R,3S,4R,5S,8R,10R,11R,12S,13S,14R)-13-[(2,6-dideoxy-3-C-methyl-3-O-methyl-4-C-[[(cyclohexyl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

134)
(2R,3S,4R,5S,8R,10R,11R,12S,13S,14R)-13-[(2,6-dideoxy-3-C-methyl-3-O-methyl-4-C-[(2-fluoro-phenyl-amino)-methyl]-α-L-ribopyranosyl)oxy]-2-ethyl-3,4,10-trihydroxy-3,5,8,10,12,14-hexamethyl-11-[[3,4,6-trideoxy-3-(dimethylamino)-β-D-xylo-hexopyranosyl]oxy]-1-oxa-7-azacyclopentadecan-15-one;

135)
(2R,3S,4R,5S,8R,10R,11R,12S,13S,14R)-13-[(2,6-dideoxy-3-C-methyl-3-O-methyl-4-C-[(3-morpholinyl-propyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

136)
(2R,3S,4R,5S,8R,10R,11R,12S,13S,14R)-13-[(2,6-dideoxy-3-C-methyl-3-O-methyl-4-C-[(2-chloro-phenylmethyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

137)
(2R,3S,4R,5S,8R,10R,11R,12S,13S,14R)-13-[(2,6-dideoxy-3-C-methyl-3-O-methyl-4-C-[(2-furyl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

138) (2R,3S,4R,5S,8R,10R,11R,12S,13S,14R)-13-[(2,6-dideoxy-3-C-methyl-3-O-methyl-4-C-[(3-aminobenzyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

139) (2R,3S,4R,5S,8R,10R,11R,12S,13S,14R)-13-[(2,6-dideoxy-3-C-methyl-3-O-methyl-4-C-[(phenylhydrazono)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

140) (2R,3S,4R,5S,8R,10R,11R,12S,13S,14R)-13-[(2,6-dideoxy-3-C-methyl-3-O-methyl-4-C-{[2-(1H-indol-3-yl)-ethylamino]-methyl}-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

141) (2R,3S,4R,5S,8R,10R,11R,12S,13S,14R)-13-[(2,6-dideoxy-3-C-methyl-3-O-methyl-4-C-[(3-chloro-propyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

142) (2R,3S,4R,5S,8R,10R,11R,12S,13S,14R)-13-[(2,6-dideoxy-3-C-methyl-3-O-methyl-4-C-[(3,5-dimethoxyphenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

143) (2R,3S,4R,5S,8R,10R,11R,12S,13S,14R)-13-[(2,6-dideoxy-3-C-methyl-3-O-methyl-4-C-[(5-methyl-furan-2-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

144) (2R,3S,4R,5S,8R,10R,11R,12S,13S,14R)-13-[(2,6-dideoxy-3-C-methyl-3-O-methyl-4-C-[(4-fluoro-phenylhydrazono)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

145) (2R,3S,4R,5S,8R,10R,11R,12S,13S,14R)-13-[(2,6-dideoxy-3-C-methyl-3-O-methyl-4-C-[(benzyloxy-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

146) (2R,3S,4R,5S,8R,10R,11R,12S,13S,14R)-13-[(2,6-dideoxy-3-C-methyl-3-O-methyl-4-C-[(p-methoxyphenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

147) (2R,3S,4R,5S,8R,10R,11R,12S,13S,14R)-13-[(2,6-dideoxy-3-C-methyl-3-O-methyl-4-C-[(3,4-dimethylphenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

148) (2R,3S,4R,5S,8R,10R,11R,12S,13S,14R)-13-[(2,6-dideoxy-3-C-methyl-3-O-methyl-4-C-[(4-fluorothiophenol)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

149) (2R,3S,4R,5S,8R,10R,11R,12S,13S,14R)-13-[(2,6-dideoxy-3-C-methyl-3-O-methyl-4-C-[(5-fluoropyridinyl-2-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

150) (2R,3S,4R,5S,8R,10R,11R,12S,13S,14R)-13-[(2,6-dideoxy-3-C-methyl-3-O-methyl-4-C-[(diethyl-methyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

151) (2R,3S,4R,5S,8R,10R,11R,12S,13S,14R)-13-[(2,6-dideoxy-3-C-methyl-3-O-methyl-4-C-[(3-morpholinyl-propyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

152) (2R,3S,4R,5S,8R,10R,11R,12S,13S,14R)-13-[(2,6-dideoxy-3-C-methyl-3-O-methyl-4-C-[(2-pyrrolyl-ethyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

153) (2R,3S,4R,5S,8R,10R,11R,12S,13S,14R)-13-[(2,6-dideoxy-3-C-methyl-3-O-methyl-4-C-[(2-pyridin-4-yl-ethylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

154) (2R,3S,4R,5S,8R,10R,11R,12S,13S,14R)-13-[(2,6-dideoxy-3-C-methyl-3-O-methyl-4-C-[(2-fluorobenzyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

155) (2R,3S,4R,5S,8R,10R,11R,12S,13S,14R)-13-[(2,6-dideoxy-3-C-methyl-3-O-methyl-4-C-[(2-piperidin-4-yl-methyl]-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

156) (2R,3S,4R,5S,8R,10R,11R,12S,13S,14R)-13-[(2,6-dideoxy-3-C-methyl-3-O-methyl-4-C-[(2-methyl-4-chloro-phenyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

157) (2R,3S,4R,5S,8R,10R,11R,12S,13S,14R)-13-[(2,6-dideoxy-3-C-methyl-3-O-methyl-4-C-[(N-methyl-butyl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

158) (2R,3S,4R,5S,8R,10R,11R,12S,13S,14R)-13-[(2,6-dideoxy-3-C-methyl-3-O-methyl-4-C-[(4,6-dichloro-pyrimidin-2-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

159) (2R,3S,4R,5S,8R,10R,11R,12S,13S,14R)-13-[(2,6-dideoxy-3-C-methyl-3-O-methyl-4-C-[(cyclohepty-lamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

160) (2R,3S,4R,5S,8R,10R,11R,12S,13S,14R)-13-[(2,6-dideoxy-3-C-methyl-3-O-methyl-4-C-(morpholinyl-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

161) (2R,3S,4R,5S,8R,10R,11R,12S,13S,14R)-13-[(2,6-dideoxy-3-C-methyl-3-O-methyl-4-C-[(4,4-dimethoxy-butylamino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

162) (2R,3S,4R,5S,8R,10R,11R,12S,13S,14R)-13-[(2,6-dideoxy-3-C-methyl-3-O-methyl-4-C-(piperidin-4-yl-amino-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

163) (2R,3S,4R,5S,8R,10R,11R,12S,13S,14R)-13-[(2,6-dideoxy-3-C-methyl-3-O-methyl-4-C-[(2,6-chloro-pyridin-3-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

164) (2R,3S,4R,5S,8R,10R,11R,12S,13S,14R)-13-[(2,6-dideoxy-3-C-methyl-3-O-methyl-4-C-(tetrahydropyrrolyl-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

165) (2R,3S,4R,5S,8R,10R,11R,12S,13S,14R)-13-[(2,6-dideoxy-3-C-methyl-3-O-methyl-4-C-[(5-hydrosulphonyl-1H-[1,2,4]triazol-3-yl-amino)-methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-1-oxa-7-azacyclopentadecan-15-one;

166) 13-[(2,6-dideoxy-3-C-methyl-3-O-methyl-4-C-[(2-amino-5-chloropyridinyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

167) 13-[(2,6-dideoxy-3-C-methyl-3-O-methyl-4-C-[(N-ethyl-methylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

168) 13-[(2,6-dideoxy-3-C-methyl-3-O-methyl-4-C-[(diallylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

169) 13-[(2,6-dideoxy-3-C-methyl-3-O-methyl-4-C-[(2,2,2-trifluoroacetamido)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

170) 13-[(2,6-dideoxy-3-C-methyl-3-O-methyl-4-C-[(3-amino-2 chloropyridinyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

171) 13-[(2,6-dideoxy-3-C-methyl-3-O-methyl-4-C-[(benzamido)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

172) 13-[(2,6-dideoxy-3-C-methyl-3-O-methyl-4-C-[(3-trifluoromethylbenzylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

173) 13-[(2,6-dideoxy-3-C-methyl-3-O-methyl-4-C-[(3-bromophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

174) 13-[(2,6-dideoxy-3-C-methyl-3-O-methyl-4-C-[(3-methoxyphenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

175) 13-[(2,6-dideoxy-3-C-methyl-3-O-methyl-4-C-[(p-iodophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

176) 13-[(2,6-dideoxy-3-C-methyl-3-O-methyl-4-C-[(2,4-dinitrophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

177) 13-[(2,6-dideoxy-3-C-methyl-3-O-methyl-4-C-[(2,4-dimethylphenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

178) 13-[(2,6-dideoxy-3-C-methyl-3-O-methyl-4-C-[(3,5-di(trifluoromethyl)phenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

179) 13-[(2,6-dideoxy-3-C-methyl-3-O-methyl-4-C-[(2,4-dichlorophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

180) 13-[(2,6-dideoxy-3-C-methyl-3-O-methyl-4-C-[(2-chlorophenylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

181) 13-[(2,6-dideoxy-3-C-methyl-3-O-methyl-4-C-[(allopurinol)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

182) 13-[(2,6-dideoxy-3-C-methyl-3-O-methyl-4-C-[(1,2,4-triazolyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one;

183) 13-[(2,6-dideoxy-3-C-methyl-3-O-methyl-4-C-[(2-methylimidazolyl)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one; or 184) 13-[(2,6-dideoxy-3-C-methyl-3-O-methyl-4-C-[(N-methyl-2-hydroxyethylamino)methyl]-α-L-ribopyranosyl)oxy]-2-ethyl-3,4,10-trihydroxy-3,5,8,10,12,14-hexamethyl-7-propyl-11-[[3,4,6-trideoxy-3-(dimethylamino)-β-D-xylo-hexopyranosyl]oxy]-(2R,3S,4R,5S,8R,10R,11R,12S,13S,14R)-1-oxa-7-azacyclopentadecan-15-one.

12. A pharmaceutically acceptable salt of the compound according to claim 1.

13. The pharmaceutically acceptable salt according to claim 12, wherein the salt is prepared from the compound and an acid, and the acid is selected from one or more of a group consisting of hydrochloric acid, oxalic acid, maleic acid, fumaric acid, citric acid, malic acid, isethionic acid, tartaric acid, methanesulfonic acid, ethanesulfonic acid, hydrobromic acid, sulfuric acid, phosphoric acid, acetic acid, propionic acid, lactic acid, trifluoroacetic acid, benzoic acid, and p-toluenesulfonic acid.

14. A pharmaceutical composition for use in treatment of bacterial infections or protozoal infections in mammals, birds, or fish, comprising a therapeutically effective amount of the compound according to claim 1 or a pharmaceutically acceptable salt thereof, and a pharmaceutically acceptable carrier thereof.

15. A method of using the compound according to claim 1 or a pharmaceutically acceptable salt thereof, the method comprising:
    treating bacterial infections or protozoal infections in mammals, birds, or fish with the compound or pharmaceutically acceptable salt thereof.

* * * * *